United States Patent
Inaba et al.

(10) Patent No.: US 6,902,879 B2
(45) Date of Patent: Jun. 7, 2005

(54) SILVER HALIDE PHOTOGRAPHIC EMULSION, SILVER HALIDE PHOTOSENSITIVE MATERIAL, AND NOVEL IRIDIUM COMPLEX AND PREPARATION PROCESS THEREOF

(75) Inventors: Tadashi Inaba, Kanagawa (JP); Takahiro Matsuno, Kanagawa (JP); Tadanobu Sato, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/228,216

(22) Filed: Aug. 27, 2002

(65) Prior Publication Data

US 2004/0002025 A1 Jan. 1, 2004

(30) Foreign Application Priority Data

Aug. 30, 2001 (JP) .................................. P.2001-261364
Sep. 26, 2001 (JP) .................................. P.2001-294199

(51) Int. Cl.$^7$ .............................................. G03C 1/06
(52) U.S. Cl. ...................... 430/604; 430/567; 430/599; 430/600; 430/605
(58) Field of Search ................ 430/567, 600, 430/599, 604, 605

(56) References Cited

U.S. PATENT DOCUMENTS

| | | | |
|---|---|---|---|
| 5,360,712 A | 11/1994 | Olm et al. | |
| 5,372,926 A | 12/1994 | Beavers et al. | |
| 5,382,503 A | 1/1995 | Murakami et al. | |
| 5,462,849 A | * 10/1995 | Kuromoto et al. | .......... 430/605 |
| 6,107,018 A | 8/2000 | Mydlarz et al. | |
| 6,162,599 A | 12/2000 | Vandenbroucke et al. | |
| 6,352,823 B1 | * 3/2002 | Sato | ............................ 430/605 |
| 6,372,419 B1 | * 4/2002 | Inaba et al. | .................. 430/604 |
| 6,403,294 B2 | * 6/2002 | Sato | ............................ 430/600 |
| 6,555,308 B1 | * 4/2003 | Asami et al. | ................ 430/567 |

FOREIGN PATENT DOCUMENTS

EP          0 945 755 A1       9/1999

* cited by examiner

Primary Examiner—Geraldine Letscher
(74) Attorney, Agent, or Firm—Sughrue Mion, PLLC

(57) ABSTRACT

Provided are a silver halide photographic emulsion containing a metal complex represented by the following formula (I):

$$M_m[IrCl_n(L_1)_k(L_2)_{6-n-k}] \quad (I)$$

wherein, M represents a cation or anion, m represents an integer of 0 to 4, n represents an integer of 3 to 5, k represents an integer of 0 to 3, $L_1$ represents a ligand selected from the group consisting of pyrroles, thiophenes, pyrazoles, isoxazoles, isothiazoles, imidazole, oxazoles, furazanes, heterocycles having at least 3 hetero atoms and ureas, $L_2$ represents an inorganic ligand other than Cl with the proviso that when k represents 0, $L_2$ represents none of F, Br, I, NO, $H_2O$, CO and $C_2O_4$; and a metal complex represented by the following formula (IV):

$$N_{k'}[IrX_{6-n'}Q_{n'}] \quad (IV)$$

wherein, N represents a counter cation; X represents a halogen ion; Q represents a compound which contains at least three atoms selected from nitrogen and sulfur atoms, and 5 or less carbon atoms, may contain another atom, and exhibits a ratio of (the number of carbon atoms)/(the total number of nitrogen atoms+oxygen atoms+sulfur atoms) of less than 0.5; n' represents an integer of 1 or 2 and k' represents the number of counter cations necessary for neutralizing the charge of a complex salt.

11 Claims, No Drawings

SILVER HALIDE PHOTOGRAPHIC EMULSION, SILVER HALIDE PHOTOSENSITIVE MATERIAL, AND NOVEL IRIDIUM COMPLEX AND PREPARATION PROCESS THEREOF

FIELD OF THE INVENTION

The present invention relates to a silver halide photographic emulsion and a silver halide photosensitive material containing the emulsion. More specifically, the present invention relates to a silver halide photographic emulsion and a photosensitive material with high contrast and free from the failure of the reciprocity law, which has been prepared using a metal complex doping technique.

Further, the present invention relates to a novel iridium metal complex and preparation process thereof. The metal complex provided by the present invention is useful as an additive in the medical field, cosmetic preparations, soaps, detergents, cleaning compositions, analysis of materials, coating of a metal material, plating, catalyst, colloid chemistry, photography (ex. developer, bleaching solution), and liquid crystals, particularly as an additive to a silver halide photosensitive material. More specifically, it is useful as an additive for a silver halide photosensitive material with high contrast and free of the failure of the reciprocity law, which has been prepared using doping technique.

BACKGROUND OF THE INVENTION

Silver halide photosensitive materials are required to have, as basic performances, high sensitivity, fine granularity and low fog. Metal doping technique is one of the means capable of satisfying these needs. Metal doping is carried out in order to modify the physical properties of silver halide grain, thereby heightening the efficiency (quantum sensitivity) of changing photoelectrons to developable latent image. More specifically, metal doping technique is to introduce (dope) a simple metal ion or a metal complex containing a ligand into silver halide grain. By this metal doping, characteristics of silver halide grain are modified and the performance of the whole emulsion can be improved as is expected. Furthermore, the general and practical surface latent image type silver halide photographic emulsion is desired to have high contrast. The term "high contrast" as used herein means that the slope of the gradation part (linear part) of a characteristic curve drawn with an exposure amount on the abscissa and an optical density on the ordinate is steep. With regards to the gradation, it is important that the characteristic curve shows a steep rise at its toe (a region of an exposure amount in which optical density starts increasing). Even in a silver halide photosensitive material such as color printing paper, high contrast at a portion corresponding to the low density portion of the characteristic curve, in other words, a steep rise at its toe is desired in order to obtain a sharp and clear image.

In Research Disclosure No. 17643, item IA, described is metal ions or metal complexes which can be introduced into silver halide grains during formation by metal doping technique. Typical examples of a metal complex used at an initial stage of metal doping technique are metal complexes of platinum, palladium, iridium, rhodium and ruthenium as described in U.S. Pat. No. 2,448,060. These water soluble metal complexes, when used as a dopant, function as an antifoggant or stabilizer. In particular, hexa-coordinated metal complexes of palladium (IV) further exhibit sensitizing action. The complexes described in the patent have, as a ligand, a halide such as chloride or bromide. In U.S. Pat. No. 3,690,888, disclosed is a preparation process of a silver halide containing a polyvalent metal ion. This process comprises forming silver halide grain in the presence of a protective colloid composed mainly of an acrylic polymer. Examples of the polyvalent metal ion used here include bismuth, iridium, lead and osmium ions. The complex described in this patent has, in addition to the metal ion, a halide such as chloride or bromide as a ligand. The above-described documents disclose the effects available when a metal ion is incorporated in silver halide grain. With regards to dopants including cyanide ion, effects of them when incorporated in silver halide emulsion are described in Japanese Patent Publication No. 35373/1973, U.S. Pat. Nos. 3,790,390, 4,847,191, 4937180, and 4945035, and Japanese Patent (Application) Laid-Open Nos. 225445/1995, 20853/1990, 20854/1990, 20852/1990, 20855/1990, 118535/1991 and 118536/1991.

On the other hand, an iridium complex is used for reducing reciprocity (law) failure, particularly the high intensity reciprocity (law) failure. Doping of an iridium complex in silver halide grain is disclosed in Japanese Patent (Application) Laid-Open No. 285941/1989, 118583/1991, 213449/1992, 278940/1992, 66511/1993, 313277/1993, 82947/1994, 235995/1994, 72569/1995, 72576/1995, 202440/1999, 295841/1999, 227640/1999 and 267215/2000 and U.S. Pat. Nos. 4,933,272, 49337180 and 5037732. Fluoride ion, chloride ion, bromide ion, $H_2O$, cyano, nitrosyl, thionitrosyl and oxalic acid ion are used as the ligand of the iridium complex.

It is known that use of a dopant for the purpose of attaining hard gradation (i.e., increasing contrast) or reducing the high intensity reciprocity (law) failure causes any one or combination of adverse effects such as sensitivity loss, latent image sensitization and reduction in maximum density. Iridium hexachloride ($IrCl_6^{-2}$, $IrCl_6^{-3}$) is mainly used at present for increasing contrast and reducing high intensity reciprocity (law) failure. This complex has high improving effects, but is accompanied with the problem that it causes all of the above-described adverse effects. It is a dopant limited in using amount and using method and thus, difficult to make full use of. A complex having a nitrosyl ligand is disclosed in European Patent Nos. 606893 and 606894, while a complex having a carbonyl ligand is disclosed in European Patent No. 415481. These complexes have effects as a dopant for increasing contrast. They however act as a deep electron trap so that even by the use of the compounds in specific examples in these documents, any of the above-described adverse effects cannot be decreased. In U.S. Pat. No. 5,360,712, a complex having a C—C, C—H or C—N—H bond is disclosed. Some of the specific examples of the compound described in it have high improving effects and adverse effects are reduced to some extent, but not a sufficient level. There is accordingly a demand for the development of a dopant further reduced in adverse effects.

SUMMARY OF THE INVENTION

A first object of the present invention is therefore to provide a photographic emulsion improved in the high intensity reciprocity (law) failure and fluctuations in sensitivity depending on illumination intensity. A second object is to provide a photographic emulsion having harder gradation without causing desensitization and latent image sensitization. A third object is to provide a photosensitive material having a higher maximum density (Dmax).

A fourth object of the present invention is to provide a metal complex capable of providing an emulsion improved in the high intensity reciprocity (law) failure and fluctuations in sensitivity depending on illumination intensity. A fifth object is to provide a metal complex capable of providing a photographic emulsion having harder gradation without causing desensitization and latent image sensitization. A six object is to provide a metal complex capable of providing a photosensitive material having a higher maximum density (Dmax). A seventh object is to stably obtain an iridium complex capable of attaining the above-described objects in a high purity and a high yield.

(1) A silver halide photographic emulsion comprising a metal complex represented by the following formula (I):

$$M_m[IrCl_n(L_1)_k(L_2)_{6-n-k}] \quad (I)$$

wherein, M represents a cation or anion, m represents an integer of 0 to 4, n represents an integer of 3 to 5, k represents an integer of 0 to 3, $L_1$ represents a ligand selected from the group consisting of pyrroles, thiophenes, pyrazoles, isoxazoles, isothiazoles, imidazoles, oxazoles, furazanes, heterocycles having at least 3 hetero atoms and ureas, $L_2$ represents an inorganic ligand other than Cl, with the proviso that when k represents 0, $L_2$ represents none of F, Br, I, NO, $H_2O$, CO and $C_2O_4$.

(2) The silver halide photographic emulsion as described above in (1), wherein $L_1$ represents a ligand selected from heterocycles having at least 3 hetero atoms and ureas, n is 5 and k is 1.

(3) The silver halide photographic emulsion as described above in (1) or (2), wherein n is 5 and k is 0.

(4) The silver halide photographic emulsion as described above in (1), further comprising a complex represented by the following formula (II):

$$[Ma(CN)_{6-x}(La)_x]^p \quad (II)$$

wherein, Ma represents a transition metal of the group VII to IX in the Periodic Table, La represents a ligand, La may be the same or different when x represents 2 or more, x is 0, 1, 2 or 3 and p is 1-, 2-, 3- or 4-.

(5) The silver halide photographic emulsion as described above in any one of (1) or (4), further comprising a complex represented by the following formula (III):

$$[Mb(NO)(Lb)_5]^q \quad (III)$$

wherein, Mb represents a transition metal of the group VII to IX in the Periodic Table, 5 pieces of Lbs may be the same or different and each represents a ligand, and q represents 1-, 2- or 3-.

(6) The silver halide photographic emulsion as described above in any one of (1) to (5), wherein the silver halide grain contained therein is silver chloroiodide, silver chlorobromide or silver chlorobromoiodide having a silver chloride content of 95 mol % or more and is a tabular grain having an average aspect ratio of 3 or more.

(7) A silver halide photosensitive material comprising a silver halide photographic emulsion as described above in any one of (1) to (6).

(8) A metal complex represented by the following formula (IV):

$$N_{k'}[IrX_{6-n'}Q_{n'}] \quad (IV)$$

wherein, N represents a counter cation; X represents a halogen ion; Q represents a compound which contains at least three atoms selected from nitrogen and sulfur atoms, and 5 or less carbon atoms, may contain another atom, and exhibits a ratio of (the number of carbon atoms)/(the total number of nitrogen atoms+oxygen atoms+sulfur atoms) of less than 0.5; n' represents an integer of 1 or 2; and k' represents the number of counter cations necessary for neutralizing the charge of a complex salt.

(9) A process for preparing a metal complex as described above in (6), which comprises using a metal complex represented by the following formula (B):

$$N_{k'}[IrX_{6-m'}(H_2O)_{m'}] \quad (B)$$

wherein, N, X and k' have the same meanings as defined in the formula (IV), and m' represents an integer of 1 or 2.

DETAILED DESCRIPTION OF THE INVENTION

The present invention will hereinafter be described specifically. The present invention features an Ir complex containing at least 3 Cl ions as a ligand and at the same time, having a specific ligand in combination therewith.

The high intensity reciprocity (law) failure of a silver halide photographic emulsion occurs owing to latent-image dispersion resulted from appearance of a large amount of photoelectrons in silver halide grain upon high intensity exposure. It is therefore possible to improve the high intensity reciprocity (law) failure by imparting the silver halide grain with a function of causing a large amount of photoelectrons resulting from high intensity exposure to escape temporarily from a conduction zone and, after a certain time, release them to the conduction zone. This means that the state in the silver halide grain upon high intensity exposure is changed to that upon low intensity exposure. This function of causing temporary escape of photoelectrons, that is, a function of temporarily capturing photoelectrons can be attained by doping of a transition metal complex (a dopant having such a function is called "electron-releasing dopant" or "intensity changing dopant"). Iridium hexachloride has so far been employed as a transition metal complex for improving the high intensity reciprocity (law) failure. When iridium hexachloride is employed, photoelectrons, which have appeared by exposure, are captured by the lowest unoccupied orbital of iridium which is the central metal (ion) of iridium hexachloride, and after their stay for a certain time in this orbital, released to the conduction zone. An average time from exposure to release of electrons thus captured is defined as an electron-releasing time.

If it takes a long time to complete the release of electrons, the failure of the reciprocity law is improved, but sensitivity depending on the time from exposure to development increases (latent-image sensitization occurs) and photographic performance becomes unstable. Accordingly, the failure of the reciprocity law must be improved without causing latent-image sensitization. It is however impossible for iridium hexachloride to sufficiently improve the high intensity reciprocity (law) failure within an extent not causing latent-image sensitization.

When a light source for exposure is fixed, electron-releasing time must be set so as to correspond to a certain exposure intensity. It is however necessary, for the purpose of preparing an emulsion always exhibiting same photographic properties even under different exposure light sources, to introduce, into silver halide grain, a dopant having a proper electron-releasing time corresponding to the intensity of respective exposure light sources.

One of the factors controlling the electron-releasing time is "depth" of electron capturing level from the bottom of the conduction zone in the silver halide grain. The deeper the level, the longer the releasing time and vice versa. By changing the ligand of iridium ion, the electron capturing level can be made deeper, whereby doping with a complex having an ideal releasing time can be expected.

The preferred examples of iridium metal complexes capable of being incorporated inside and/or on the surface of silver halide grain during formation and/or growth of the silver halide grain in the present invention will next be described.

Ir complexes represented by the formula (I) will be described specifically.

Pyrroles, thiophenes, pyrazoles, isoxazoles, isothiazoles, imidazoles, oxazoles, and furazanes represented by $L_1$ in the formula (I) may have a substituent. Examples of the substituent include halogen atoms (fluorine, chlorine, bromine and iodine), alkyl groups (linear, branched or cyclic, substituted or unsubstituted alkyl groups, preferably $C_{1-10}$ alkyl groups such as methyl, ethyl, n-propyl, isopropyl and t-butyl), heterocyclic groups (preferably a monovalent group resulting from eliminating one hydrogen atom from a 5- or 6-membered, substituted or unsubstituted, aromatic or non-aromatic heterocyclic compound, more preferably a 5- or 6-membered aromatic heterocyclic group having from 3 to 20 carbon atoms such as 2-furyl, 2-thienyl, 2-pyrimidinyl and 2-benzothiazolyl), a cyano group, a hydroxyl group, a nitro group, a carboxyl group, alkoxy groups (preferably, substituted or unsubstituted $C_{1-10}$ alkoxy groups such as methoxy, ethoxy, isopropoxy, t-butoxy, n-octyloxy and 2-methoxyethoxy), acyloxy groups (preferably a formyloxy group and a substituted or unsubstituted $C_{2-10}$ alkylcarbonyloxy group), carbamoyloxy groups (preferably substituted or unsubstituted $C_{1-10}$ carbamoyloxy groups such as N,N-dimethylcarbamoyloxy, N,N-diethylcarbamoyloxy, morpholinocarbonyloxy, N,N-di-n-octylaminocarbonyloxy and N-n-octylcarbamoyloxy), alkoxycarbonyloxy groups (preferably, substituted or unsustituted $C_{2-10}$ alkoxycarbonyloxy groups such as methoxycarbonyloxy, ethoxycarbonyloxy, t-butoxycarbonyloxy and n-octylcarbonyloxy), amino groups (preferably amino group and substituted or unsubstituted $C_{1-10}$ alkylamino groups), acylamino groups (preferably formylamino group and substituted or unsubstituted $C_{1-10}$ alkylcarbonylamino groups), aminocarbonylamino groups (preferably, substituted or unsubstituted $C_{1-10}$ aminocarbonylamino groups such as carbamoylamino, N,N-dimethylaminocarbonylamino, N,N-diethylaminocarbonylamino and morpholinocarbonylamino), alkoxycarbonylamino groups (preferably, substituted or unsubstituted $C_{2-10}$ alkoxycarbonylamino groups such as methoxycarbonylamino, ethoxycarbonylamino, t-butoxycarbonylamino, n-octadecyloxycarbonylamino and N-methyl-methoxycarbonylamino), sulfamoylamino groups (preferably, substituted or unsubstituted $C_{0-10}$ sulfamoylamino groups such as sulfamoylamino, N,N-dimethylaminosulfonylamino and N-n-octylaminosulfonylamino), alkyl- and aryl-sulfonylamino groups (preferably, substituted or unsubstituted $C_{1-10}$ alkylsulfonylamino), a mercapto group, alkylthio groups (preferably, substituted or unsubstituted $C_{1-10}$ alkylthio groups such as methylthio, ethylthio and n-hexadecylthio), sulfamoyl groups (preferably, substituted or unsubstituted $C_{0-10}$ sulfamoyl groups such as N-ethylsulfamoyl, N-(3-dodecyloxypropyl)sulfamoyl, N,N-dimethylsulfamoyl and N-acetylsulfamoyl), a sulfo group, alkyl- and aryl-sulfinyl groups (preferably substituted or unsubstituted $C_{1-10}$ alkylsulfinyl groups), alkyl- and aryl-sulfonyl groups (preferably, substituted or unsubstituted $C_{1-10}$ alkylsulfonyl groups), acyl groups (preferably, formyl group and substituted or unsubstituted $C_{2-10}$ alkylcarbonyl groups), alkoxycarbonyl groups (preferably, substituted or unsubstituted $C_{2-10}$ alkoxycarbonyl groups such as methoxycarbonyl, ethoxycarbonyl, t-butoxycarbonyl and n-octadecyloxycarbonyl), carbamoyl groups (preferably, substituted or unsubstituted $C_{1-10}$ carbamoyl groups such as carbamoyl, N-methylcarbamoyl, N,N-dimethylcarbamoyl, N,N-di-n-octylcarbamoyl, and N-(methylsulfonyl)carbamoyl), imide groups (preferably, N-succinimide and N-phthalimide), phosphino groups (preferably, substituted or unsubstituted $C_{2-10}$ phosphino groups such as dimethylphosphino, diphenylphosphino and methylphenoxyphosphino), phosphinyl groups (preferably, substituted or unsubstituted $C_{2-10}$ phosphinyl groups such as phosphinyl, dioctyloxyphosphinyl and diethoxyphosphinyl), phosphinyloxy groups (preferably, substituted or unsubstituted $C_{2-10}$ phosphinyloxy groups such as diphenoxyphosphinyloxy and dioctyloxyphosphinyloxy), phosphinylamino groups (preferably, substituted or unsubstituted $C_{2-10}$ phosphinylamino groups such as dimethoxyphosphinylamino and dimethylaminophosphinylamino) and silyl groups (preferably, substituted or unsubstituted $C_{3-10}$ silyl groups such as trimethylsilyl, t-butyldimethylsilyl and phenyldimethylsilyl). Each of these substituents is designated as Substituent V. The Substituents V having a hydrogen atom may be substituted with the above-exemplified group after removal of the hydrogen atom.

In the formula (1), the heterocycles represented by $L_1$ and containing at least 3 hetero atoms may be monocyclic or condensed, or saturated or unsaturated. Examples include thiadiazoles (e.g., 1,2,4-thiadiazole, 1,3,4-thiadiazole, 2,5-dichloro-[1,3,4]-thiadiazole, 2,5-difluoro-[1,3,4]-thiadiazole, 2-chloro-5-fluoro-[1,3,4]-thiadiazole, 3,5-difluoro-[1,2,4]-thiadiazole, 1,2,3-thiadiazole), triazoles (e.g., 1,2,4-triazole, 3,5-dichloro-4H-[1,2,4]-triazole), thiatriazoles (e.g., 5-chloro-[1,2,3,4]-thiatriazole), triazines (e.g., [1,3,5]triazine-2,4,6-trithiol), tetrazoles (e.g., 1H-tetrazole and 1H-tetrazole-5-thiol), purines, pteridines, imidathiazoles (e.g., 4H-imidazo[4,5-d]thiazole, imidazo[2,1-b]thiazole), pyrazinopyridazines (e.g., pyrazino[2,3-d]pyridazine), and pyrazolo-oxazoles (e.g., 1H-pyrazolo[3,4-d]oxazole). These heterocycles may have a substituent and those described as Substituent V are usable as the substituent.

Examples of the ureas represented by $L_1$ in the formula (I) include ureas, thioureas, selenoureas and telluroureas. They may have a substituent. Those described as Substituent V are usable as the substituent. Preferred are alkyl groups and hydroxyl group. These substituents may have a further substituent. Specific examples include thiourea, N-methylthiourea, N,N,N',N'-tetramethylthiourea, S-methylthiourea and selenourea.

Preferred examples of the ligand represented by $L_1$ in the formula (I) include heterocycles having at least 3 hetero atoms and ureas, more preferably, heterocycles having at least 3 hetero atoms (particularly, thiadiazoles).

As the inorganic ligand represented by $L_2$ in the formula (I), any inorganic ligand other than Cl is usable. When k represents 0, however, $L_2$ represents none of F, Br, I, NO, $H_2O$, CO and $C_2O_4$. Specific examples of $L_2$ include $AlO_2^-$, $B_2^{3-}$, $B_2O_3$, $B^{3-}$, $B_4O_7^{2-}$, $B_5O_8-$, $B_6^{2-}$, $BBr_3$, $BCl_3$, BF, BN, $BN(SiH_3)_2$, $BNH_2$, BO, $BO_2^-$, $BO_3^-$, $BO_3^{3-}$, $Br^-$, $Br_3^-$, $BrCl_2^-$, $BrO_3^-$, $C^-$, $CF_3SO_2NH_2$, $ClO^-$, $ClO_2^-$, $ClO_3^-$, $ClO_4^-$, $CN^-$, $CNO^-$, CO, $CO_2$, $CO_3^{2-}$, $CS_2$, $CS_3^{2-}$, $F^-$, $H^-$, $H_2O$, $I^-$, $I_3^-$, $IBr_2^-$, $ICl_2^-$, $IO_3^-$, $IO_4^-$, $N_2$, $N_3^-$, $N_3^-$, NCCl, $NCO^-$, $NCS^-$, $NCSe^-$, $NCTe^-$, $NCS_3CN$, $NH_2-$, $NH_2NH_2$, $NH_2OH$, $NH_2OSO_3H$, $NH_2SO_2NH_2$, $NH_2SO_3H$, $NH_3$, $NO^+$, $NO_2^-$, $NO_3^-$, NS, NSF, $NSF_2$, $NSF_3$, NSO, $O^{2-}$, $O_2^-$, $O_2^{2-}$, $O_3^{2-}$, $OH_2$, $OCN^-$, $P_2O_7^{4-}$, $P^{3-}$, $PBr_3$, $PCl_3$, $PF_3$, $PH_3^-$, $PO(NCO)_3$, $PO_2H_2^-$, $PO_3^-$, $PO_3^{3-}$, $PO_4^{3-}$, $POF_3$, $S(NSO)_2$, $S^{2-}$, $S_2O$, $S_2O_2$, $S_2O_3^{2-}$, $S_2O_4^{2-}$, $S_2O_5^{2-}$, $S_2O_6^{2-}$, $S_2O_7^{2-}$, $S_2O_8^{2-}$, $S_3O_7^{2-}$, $S_4O_6^{2-}$, $S_5O_6^{2-}$, $Sb^{3-}$, $SCN^-$, $Se^{2-}$, $SeCN^-$, $SeO_3^{2-}$, $SeO_4^{2-}$, $SH^-$, $Si^-$, $Si_4O_9^{2-}$, $SiCl_3^-$, $SiCl_4$, $SiH_4$, SiO, $SiO_2$, $SiO_3^{2-}$, $SiO_4^{2-}$, $SnCl_2$, $SnCl_3^-$, $SnS_3^{2-}$, SO, $SO_2$, $SO_3$, $SO_3^{2-}$, $SO_3F^-$, $SO_4^{2-}$, $Te^{2-}$, $TeCN^-$, $TeO_3^{2-}$, $TeO_4^{2-}$, $PS(NH_2)_3$, $PS(NH_2)(OH)_2$, $PO(NH_2)_3$, $P(O)(NH_2)(OH)_2$, $PS(OH)_3$, $(CN)_2N^-$, $^{(CN)}{_2}S$, $(CN)_3P$, $P(S)(CN)_3$, $(CF_3SO_2)_2N^{-(CF)}{_3}SO_2)(CN)N^-$, $TiO_3^{2-}$, $MgO_4^{6-}$, $VO_3^-$, $VO_4^{3-}$, $V_2O_7^{4-}$, $CrO_4^{2-}$, $CrO_8^{3-}$, $Cr_2O_7^{2-}$, $MnO_4^{2-}$, $MnO_4^-$, $FeO_3^-$, $FeO_4^{2-/3-}$, $NiO_4^{6-}$, $ZnO_4^{6-}$, $MoO_4^{2-}$, $WO_4^{2-}$ and $ReO_4^-$. Of which, preferred are $CNO^-$, $CO_2$, $CO_3^{2-}$, $CS_2$, $CS_3^{2-}$, $N_2$, $N_3^-$, $NCO^-$, $NCS^-$, $NCSe^-$, $NCTe^-$, $NCS_3CN$, $NH_2^-$, $NH_2NH_2$, $NH_2OH$, $NH_2OSO_3H$, $NH_2SO_2NH_2$, $NH_2SO_3H$, $NH_3$, NSO, $OCN^-$, $P_2O_7^{4-}$, $PO(NCO)_3$, $PO_2H_2^-$, $PO_3^{3-}$, $S(NSO)_2$, $S_2O$, $S_2O_2$, $S_2O_3^{2-}$, $S_2O_4^{2-}$, $S_2O_5^{2-}$, $S_2O_6^{2-}$, $S_2O_7^{2-}$, $S_2O_8^{2-}$, $S_3O_7^{2-}$, $S_4O_6^{2-}$, $S_5O_6^{2-}$, $SCN^-$, $SeCN^-$, $SeO_3^{2-}$, $SH^-$, $SO_2$, $SO_3$, $SO_3^{2-}$, $TeCN^-$, $TeO_3^{2-}$, $TeO_4^{2-}$, $PS(NH_2)_3$, $P(S)(NH_2)(OH)_2$, $PO(NH_2)_3$, $P(O)(NH_2)(OH)_2$, $P(S)(OH)_3$, $(CN)_2N^-$, $(CN)_2S$, $(CN)_3P$, $P(S)(CN)_3$, $(CF_3SO_2)_2N$ and $(CF_3SO_2)(CN)N^-$, with $CNO^-$, $NCO^-$, $NCS^-$, $NH_2NH_2$, $NH_2OH$, $NH_2OSO_3H$, $NH_2SO_2NH_2$, $NH_2SO_3H$, $NH_3$, NSO, $OCN^-$, $SCN^-$, $(CN)_2N^-$, $(CN)_2S$, $(CN)_3P$, $P(S)(CN)_3$, $(CF_3SO_2)_2N^-$ and $(CF_3SO_2)(CN)N^-$ being more preferred. Especially preferred are $NH_2OH$, $NH_2OSO_3H$, $NH_3$, $(CN)_2N^-$ and $(CN)_2S$.

Examples of the cation represented by M include alkali metal ions (such as sodium ion, potassium ion, rubidium ion and cesium ion), alkaline earth metal ions (such as magnesium ion and calcium ion), transition metal ions (such as iron ion and ruthenium ion), and ammonium ions (ammonium ion and tetraethylammonium ion). Of these, preferred are alkali metal ions, more preferably sodium ion, and potassium ion, especially potassium ion.

Examples of the anion represented by M include halogen ions (such as chlorine ion, bromine ion and iodine ion), nitric acid ions, sulfuric acid ions, sulfonatos (such a p-toluenesulfonato and trifluoromethanesulfonato), hexafluorophosphate, tetrafluoroborate, perhydrochloric acid ions and carboxylates (such as oxalate and acetate).

The letter m represents an integer of 0 to 4 and is the numerical value necessary for neutralizing the charge of the complex. When m represents 2 or greater, Ms may be the same or different.

The letter n represents an integer of 3 to 5. When n represents 3 or 4, a plurality of $L_1$ or $L_2$ may be the same or different, preferably they are the same. As n, preferred is 4 or 5, most preferably 5.

The letter k represents an integer of 0 to 3, preferably 0 or 1, especially 0.

Ir ion is usually monovalent to tetravalent in the form of a complex, but preferably it is trivalent or tetravalent, more preferably trivalent ($3^+$). Iridium hexachloride which has so far been used for photography is preferably tetravalent from the viewpoint of stability of its aqueous solution. The complex of the present invention is however stable when dissolved in an aqueous solution so that it is preferably trivalent as a state to be doped.

Specific examples of the present invention will next be described, but not limited thereto. The charge of Ir may be either 3+ or 4+. When the charge changes from 3+ to 4+by oxidation, one of the counter cations of the complex is removed.

The following are specific examples of the compound represented by the formula (I), but the scope of the present invention is not limited to them.

$K_2[IrCl_5(SH)]$, $K_4[IrCl_5(S_2O_5)]$, $K_3[IrCl_5(CN)]$, $K_3[IrCl_4(CN)_2]$, $Cs_5[IrCl_5(PO_3)]$, $Rb_5[IrCl_5(OBO_2)]$, $Cs_3[IrCl_5(OBO_2)]$, $K_3[IrCl_5(NH_2SO_3)]$, $Cs_4[IrCl_5(B_4O_7)]$, $Cs_4[IrCl_5(S_2O_3)]$, $[IrCl_3(H_2NNH_2)_3]$, $Cs_2[IrCl_5(H_2NSO_2NH_2)]$, $K_5[IrCl_5(NH_3)]$, $K[IrCl_4(NH_3)_2]$, $[IrCl_3(NH_3)_3]$, $K_2[IrCl_5(NH_2OH)]$, $K[IrCl_4(NH_2OH)_2]$, $K_3[IrCl_5(NO_2)]$, $Cs_5[IrCl_5(PO_2H_2)]$, $K_3[IrCl_5(NCO)]$, $K_3[IrCl_4(NCO)_2]$, $K_2[IrCl_5(H_2NNH_2)]$, $K_4[IrCl_5(SiO_3)]$, $K_2[IrCl_5(CS_2)]$, $K_4[IrCl_5(CO_3)]$, $K_3[IrCl_4(CO_3)]$, $K_3[IrCl_5(CNO)]$, $K_2[IrCl_5(N_2)]$, $K_3[IrCl_5(N_3)]$, $K_3[IrCl_5(NCS)]$, $K_3[IrCl_5(NCSe)]$, $K_3[IrCl_5(NCTe)]$, $K_3[IrCl_5(OCN)]$, $K_4[IrCl_5(SO_3)]$, $K_3[IrCl_5(SCN)]$, $K_3[IrCl_5(SeCN)]$, $K_3[IrCl_5(TeCN)]$, $K_2[IrCl_5(S=P(NH_3)_3)]$, $K_2[IrCl_5(S=P(NH_3)_2(OH))]$, $K_2[IrCl_5(S=P(NH_3)(OH)_2)]$, $K_2[IrCl_5(S=P(OH)_3)]$, $K_2[IrCl_5(O=P(NH_3)_3)]$, $K_2[IrCl_5(O=P(NH_3)_2(OH))]$, $K_2[IrCl_5(O=P(NH_3)(OH)_2)]$, $K_2[IrCl_5(O=P(OH)_3)]$, $K_2[IrCl_5(S=P(CN)_3)]$, $KNa[IrCl_4(NH_2C(=S)NH_2)(NH_2SO_3)]$, $NH_3[IrCl_4(NH_2C(=S)NH_2)NH_3)]$, $Na_2[IrCl_4(NH_2C(=S)NH_2)(NO_2)]$, $K_2[IrCl_4(NH_2C(=S)NH_2)(SCN)]$, $K_2[IrCl_4(NH_2C(=S)NH_2(OH)]$, $K_2[IrCl_4(NH_2C(=S)NH_2)(OH_2)]$, $K_2[IrCl_5(NH_2C(=NH)SCH_3)]$, $K_2[IrCl_4(NH_2C(-NH)SCH_3)(NCO)]$, $K[IrCl_4(NH_2C(=NH)SCH_3)(NH_2OH)]$, $K[IrCl_4(NH_2C(=NH)SCH_3)(OH_2)]$, $K_2[IrCl_5(NH_2C(=S)NH_2)]$, $K_2[IrCl_5(NH_2C(=S)NHCH_3)]$, $K_2[IrCl_5(CH_3NHC(=S)NHCH_3)]$, $K_2[IrCl_5((CH_3)_2NC(=S)N(CH_3)_2)$, $K_2[IrCl_5(NH_2C(=Se)NH_2)]$, $K_2[IrCl_5((CH_3)_2NC(=Se)N(CH_3)_2)]$, $K_2[IrCl_5((CH_3)_2NC(=Se)N(CH_3)(CH_2CO_2K))]$, $K_3[IrCl_5(N(NC)_2)]$, $Cs_3[IrCl_5(N(NC)_2)]$, $KNa_2[IrCl_5(N(NC)_2)]$, $Na_3[IrCl_5(N(NC)_2)]$, $K_2[IrCl_4(N(NC)_2)(OH_2)]$, $K_3[IrCl_4(N(NC)_2)(OH)]$, $K_3[IrCl_4(N(NC)_2)(NO_2)]$, $K_3[IrCl_4(N(NC)_2)(NH_3)]$, $K_2[IrCl_5(S(NC)_2)]$, $K_3[IrCl_5(N(SO_2CF_3)_2)]$, $K_3[IrCl_5(N(CN)(SO_2CF_3))$, $K_2[IrCl_5([1,3,4]$-thiadiazole)$]$, $K[IrCl_4([1,3,4]$-thiadiazole$)(H_2O)]$, $K_2[IrCl_5(2,5$-dichloro-$[1,3,4]$-thiadiazole$)]$, $K_2[IrCl_5(2,5$-difluoro-$[1,3,4]$-thiadiazole$)]$, $K_2[IrCl_5(2$-chloro-$5$-fluoro-$[1,3,4]$-thiadiazole$)]$, $K[IrCl_4(2,5$-difluoro-$[1,3,4]$-thiadiazole$)(NH_3)]$, $K_3[IrCl_5(2,5$-dimercapto-$[1,3,4]$-thiadiazole$)]$, $K_3[IrCl_5(2,5$-disulfamoyl-$[1,3,4]$-thiadiazole$)]$, $K_3[IrCl_5(2$-amino-$5$-sulfamoyl-$[1,3,4]$-thiadiazole$)]$, $K_3[IrCl_5(2$-fluoro-$5$-sulfamoyl-$[1,3,4]$-thiadiazole$)]$, $K_2[IrCl_5([1,2,4]$-thiadiazole$)]$, $K_2[IrCl_5(3,5$-dichloro-$[1,2,4]$-thiadiazole$)]$, $K_2[IrCl_5(1,2,4$-thiadiazole$)]$, $K_3[IrCl_5(1,3,5$-triazine-$2,4,6$-trithiole$)]$, and $K_3[IrCl_5(1H$-tetrazole-$5$-thiole$)]$.

The complex of the present invention can be synthesized by some processes. For example, it can be synthesized with reference to Gmelin Handbuch der Anorganischen Chemie, Iridium, Erganzungsband 2.

The above-described complex of the formula (I) is preferably used in an amount of from $1\times10^{-10}$ mol to $1\times10^{-4}$ mol, preferably from $1\times10^{-9}$ mol to $1\times10^{-5}$ mol per mol of silver of the silver halide emulsion.

In the formula (II), Ma represents a transition metal belonging to the group VII to IX in the Periodic Table, preferably rhenium, iron, ruthenium, osmium, cobalt, rhodium or iridium, more preferably, iron or ruthenium. The ligand as La in the formula (II) may be either an organic ligand or an inorganic ligand, but preferably an inorganic ligand, more preferably a monovalent anionic ligand. The letter x represents an integer of 0 to 3, preferably 0 to 1, more preferably 0. The letter p represents 1-, 2-, 3- or 4-, preferably 3- or 4-, more preferably 4-. As the formula (II), most preferred is $[Fe(CN)_6]^{4-}$ and $[Ru(CN)_6]^{4-}$.

Since the counter cation of the complex represented by the formula (II) is dissolved in water upon preparation of an emulsion and it has therefore almost no influence on the photographic performance, any cation may be employed. Examples include ammonium ion, alkali metal ions and alkaline earth metal ions. When solubility and deliquescence are taken into consideration, ammonium ion and alkali metal ions are preferred from the viewpoint of handling ease, of which alkali metal ions are more preferred, with potassium ion being especially preferred.

The complex represented by the formula (II) is added preferably in an amount of from $1\times10^{-8}$ mol to $1\times10^{-2}$ mol, preferably from $1\times10^{-6}$ mol to $5\times10^{-4}$ mol, more preferably from $2\times10^{-6}$ mol to $1\times10^{-5}$ mol per mol of silver of the silver halide emulsion.

The followings are specific examples of the compound represented by the formula (II), but the scope of the present invention is not limited thereto.

$[Fe(CN)_6]^{4-}$, $[Fe(CN)_6]^{3-}$, $[Ru(CN)_6]^{4-}$, $[RU(CN)_6]^{3-}$, $[Os(CN)_6]^{4-}$, $[Co(CN)_6]^{3-}$, $[Rh(CN)_6]^{3-}$, $[Ir(CN)_6]^{3-}$, $[Ir(CN)_6]^{2-}$, $[Re(CN)_6]^{4-}$, $[RuCl(CN)_5]^{4-}$, $[OsCl(CN)_5]^{4-}$, $[OsBr(CN)_5]^{4-}$, $[Fe(CO)(CN)_5]^{3-}$, $[Ru(CN)_5(OCN)]^{4-}$, and $[Ru(CN)_5(N_3)]^{4-}$.

In the formula (III), Mb represents a transition metal belonging to the group VII to IX in the Periodic Table, preferably rhenium, iron, ruthenium, osmium, cobalt, rhodium or iridium, more preferably, rhodium or osmium. The ligand as Lb in the formula (III) may be either an organic ligand or an inorganic ligand, but preferably an inorganic ligand, more preferably a monovalent anionic ligand, especially a halogen ion. The letter q represents an integer of 1-, 2- or 3-, preferably 2-. As (III), most preferred is $[Rh(NO)Cl_5]^-$ and $[Os(NO)Cl_5]^{2-}$. Since the counter cation of the complex represented by the formula (III) is dissolved in water upon preparation of an emulsion and it has therefore almost no influence on the photographic performance, any cation may be employed. Examples thereof include ammonium ion, alkali metal ions and alkaline earth metal ions. When solubility and deliquescence are taken into consideration, ammonium ion and alkali metal ions are preferred from the viewpoint of handling ease, of which alkali metal ions are more preferred, with potassium ion being especially preferred.

The complex represented by the formula (III) is added preferably in an amount of from $1\times10^{-10}$ mol to $1\times10^{-7}$ mol, preferably from $1\times10^{-9}$ mol to $5\times10^{-8}$ mol, especially from $1\times10^{-6}$ mol to $1\times10^{-8}$ mol per mol of silver of the silver halide emulsion.

The followings are specific examples of the compound represented by the formula (III), but the scope of the present invention is not limited thereto.

$[Ru(NO)Cl_5]^-$, $[Ru(NO)Br_5]^{2-}$, $[Ru(NO)I_5]^{2-}$, $[Ru(NO)Cl_4(CN)]^{2-}$, $[Ru(NO)Cl_4(OH_2)]^-$, $[Ru(NO)Cl_4(N_3)]^{2-}$, $[Ru(NO)Cl_4(SCN)]^{2-}$, $[Os(NO)Cl_5]^{2-}$, $[Os(NO)Br_5]^{2-}$, $[Os(NO)I_5]^{2-}$, $[Os(NO)Cl_4(CN)]^{2-}$, $[Os(NO)Cl_4(OH_2)]^-$, $[Os(NO)Cl_4(N_3)]^{2-}$, $[Os(NO)Cl_4(SCN)]^{2-}$, $[Ir(NO)Cl_5]^-$, $[Ir(NO)Br_5]^-$, $[Ir(NO)I_5]^-$, and $[Re(NO)Cl_5]^{2-}$.

Novel iridium complexes useful for silver halide photosensitive materials, other than metal complexes represented by the formulas (I), (II) and (III); and preparation process thereof will next be described.

These novel iridium complexes are characterized by that they have both a ligand containing at least 3 nitrogen atoms and/or sulfur atoms and a halogen ligand.

Novel metal complexes represented by the formula (IV) will next be described specifically.

Examples of the counter cation represented by N in the formula (IV) include alkali metal ions (such as lithium ion, sodium ion, potassium ion, rubidium ion and cesium ion), alkaline earth metals (such as magnesium ion, calcium ion, strontium ion and barium ion), and onium salts (such as ammonium salt and pyridinium salt). Of these, preferred are alkali metal ions and alkaline earth metal ions, more preferably alkali metal ions. As alkali metal ions, sodium ion, potassium ion, rubidium ion and cesium ion are preferred, with potassium ion and cesium ion being more preferred.

The iridium ion in the formula (IV) may usually be monovalent to tetravalent in the state of a complex, preferably trivalent or tetravalent, more preferably trivalent. Iridium hexachloride which has so far been used for photography was thought to be preferably tetravalent (such as $K_2[IrCl_6]$ or $Na_2[IrCl_6]$) from the viewpoint of stability of its aqueous solution. The complex of the present invention is stable even in the form of an aqueous solution, so that it is rather preferred to be trivalent, the state to be doped.

Specific examples of the halide ion represented by X in the formula (IV) include fluoride ions, chloride ions, bromide ions, and iodide ions. Of these, chloride ions and bromide ions are preferred, with chloride ions being more preferred.

The letter k' in the formula (IV) represents an integer of 0 to 4, which is necessary for neutralizing the charge of the complex. When k' is 2 or greater, N and N' may be the same or different. The letter n' in the formula (IV) represents an integer of 1 or 2, preferably 1.

The ligand represented by Q in the formula (IV) is a compound which contains at least three atoms selected from nitrogen atoms and/or sulfur atoms, and 5 or less carbon atoms and may contain another atom, and has a ratio of (the number of carbon atoms) to (the total number of nitrogen atoms+oxygen atoms+sulfur atoms) of less than 0.5. Of these ligands represented by Q in the formula (IV), preferred are ligands represented by the below-described formula (A) or ligands which are 5- or 6-membered heterocycles, contain at least 3 atoms selected from nitrogen atoms, oxygen atoms and/or sulfur atoms and contain 3 or less carbon atoms.

Formula (A):

wherein, L represents $N^-$, NH, C=O, C=S, C=Se, C=Te, C=NH, S, S=O, P, P=O, P=S, P=Se, P=Te or P—S—, R represents a group which contains two or less carbon atoms and has a ratio of (the number of carbon atoms) to (the total number of nitrogen atoms+oxygen atoms+sulfur atoms) of less than 0.5, q represents an integer of 2 or 3 and Rs may be the same or different).

More preferred examples of the ligands represented by Q in the formula (IV) include respective ligands represented by the formula (A-1-a), (A-1-b), (A-1-c), (A-1-d) and (A-1-e) and ligands which are 5-membered heterocycles and containing therein at least 3 atoms selected from nitrogen atoms and/or sulfur atoms. Especially preferred are ligands which are 5-membered heterocycles and contain therein at least 3 atoms selected from nitrogen atoms and/or sulfur atoms.

Formula (A-1-a)

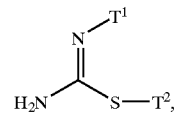

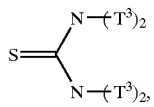 Formula (A-1-b)

 Formula (A-1-c)

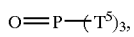 Formula (A-1-d)

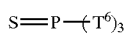 Formula (A-1-e)

wherein, $T^1$ to $T^5$ each represents a hydrogen atom, an alkyl group, a hydroxyl group, an amino group, a cyano group or a sulfonyl group and they may have one or more substituents which are the same or different.

The letter L in the formula (A) represents $N^-$, NH, C=O, C=S, C=Se, C=Te, C=NH, S, S=O, P, P=O, P=S, P=Se, P=Te or P=$S^-$, preferably $N^-$, NH, C=O, C=S, C=NH, P=O or P=S, more preferably $N^-$, C=S, C=NH or P=S, especially $N^-$.

The group represented by R in the formula (A) is a group which contains two or less carbon atoms and has a ratio of (the number of carbon atoms) to (the total number of nitrogen atoms+oxygen atoms+sulfur atoms) of less than 0.5. Examples of the group include hydrogen atom, alkyl groups, hydroxyl group, amino group, cyano group, sulfonyl group, nitro group, formyl group, carboxyl group, sulfinyl group, sulfamoyl group, alkyloxycarbonyl groups and acylmercapto group. Preferred are $CF_3$, $CCl_3$, CN, CHO, $CO_2H$, $CO_2CH_3$, $NO_2$, $S(O)CH_3$, $S(O)_2CH_3$, $SO_2NH_2$ and $SCOCH_3$, with $CF_3$, $CCl_3$, CN, CHO, $CO_2H$, $CO_2CH_3$, $S(O)CH_3$, $SO_2NH_2$ and $SCOCH_3$ being more preferred. Of these, CN being especially preferred.

The letter q in the formula (A) represents an integer of 2 or 3, preferably 2.

$T^1$ to $T^6$ in the formulas (A-1-a) to (A-1-e) each represents hydrogen atom, alkyl group, hydroxyl group, amino group, cyano group and sulfonyl group. The alkyl groups include $C_{1-2}$ alkyl groups such as methyl, ethyl and trifluoromethyl. These substituents may have a further substituent.

The letter m' in the formula (B) represents an integer of 1 or 2, preferably 1.

Of the complexes represented by the formula (IV), preferred are those represented by the formula (V) or (VI). Of the complexes represented by the formulas (V) and (VI), more preferred are those of the formula (V-1) and (VI-1), respectively.

$N^1{}_{k'}[IrX^1{}_5Q^1]$ (V)

wherein k' has the same meaning as described in the formula (IV), $N^1$ represents an alkali metal ion, $X^1$ represents a chloride or bromide ion and $Q^1$ represents a ligand represented by the following formula (A):

L-(R)$_q$ (A)

wherein, L represents $N^-$, NH, C=O, C=S, C=Se, C=Te, C=NH, S, S=O, P, P=O, P=S, P=Se, P=Te or P—$S^-$, R represents a group which contains two or less carbon atoms and has a ratio of (the number of carbon atoms) to (the total number of nitrogen atoms+oxygen atoms+sulfur atoms) of less than 0.5, q represents an integer of 2 or 3 and Rs may be the same or different).

$N^1{}_{k'}[IrCl_5Q^2]$ (V-1)

wherein, $N^1$ and K' have the same meanings as described above in the formula (V), $Q^2$ represents a ligand represented by the below-described formula (A-1-a), (A-1-b), (A-1-c), (A-1-d) or (A-1-e).

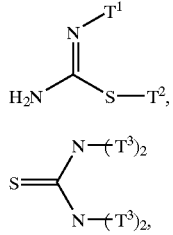 Formula (A-1-a)

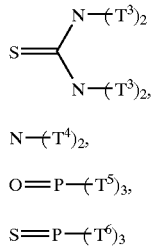 Formula (A-1-b)

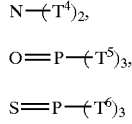 Formula (A-1-c)

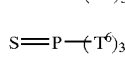 Formula (A-1-d)

$S=P\!-\!(T^6)_3$ Formula (A-1-e)

wherein, $T^1$ to $T^6$ each represents a hydrogen atom, an alkyl group, a hydroxyl group, an amino group, a cyano group or a sulfonyl group and they may have one or more substituents which are the same or different.

$N^1{}_{k'}[IrX^1{}_5Q^3]$ (VI)

wherein, k' has the same meaning as described in the formula (I), $N^1$ represents an alkali metal ion, $X^1$ represents a chloride or bromide ion and $Q^3$ represents a compound which is a 5- or 6-membered heterocycle and contains therein at least 3 atoms selected from nitrogen atoms, oxygen atoms and/or sulfur atoms, and 3 or less carbon atoms, and has a ratio of (the number of carbon atoms) to (the total number of nitrogen atoms+oxygen atoms+sulfur atoms) of less than 0.5

$N^1{}_{k'}[IrCl_5Q^4]$ (VI-1)

wherein, $N^1$ and k have the same meanings as described in the formula (V), and $Q^4$ represents a compound which is a 5-membered heterocycle and contains therein at least 3 atoms selected from nitrogen atoms and/or sulfur atoms and has a ratio of (the number of carbon atoms) to (the total number of nitrogen atoms+oxygen atoms+sulfur atoms) of less than 0.5.

In the formula (VI), the 5- or 6-membered heterocycle represented by Q3 is a compound which contains therein at least any three atoms of nitrogen atoms, oxygen atoms and sulfur atoms and has a ratio of (the number of carbon atoms) to (the total number of nitrogen atoms+oxygen atoms+sulfur atoms) of less than 0.5. More preferred are 5-membered heterocyclic compounds containing at least 3 atoms selected from nitrogen and/or sulfur atoms. Specific examples include thiadiazoles (e.g., 1,2,4-thiadiazole, 1,3,4-thiadiazole, 2,5-dichloro-[1,3,4]-thiadiazole, 2,5-difluoro-[1,3,4]-thiadiazole, 2-chloro-5-fluoro-[1,3,4]-thiadiazole, 3,5-difluoro-[1,2,4]thiadiazole, 1,2,3-thiadiazole), triazoles (e.g., 1,2,4-triazole, 3,5-dichloro-4H-[1,2,4]-triazole), and tetrazoles (e.g., 1H-tetrazole and 1H-tetrazole-5-thiol). Of which preferred are thiadiazoles and triazoles, with thiadiazoles being more preferred.

Ir has either a trivalent charge or tetravalent charge so that when trivalent Ir is oxidized into tetravalent Ir, the complex loses one counter cation.

Preferred specific examples of the compound represented by he formula (IV) are shown below, but the scope of the present invention is not limited thereto.

$K_2[IrCl_5(S=P(NH_2)_3)]$ $K_2[IrCl_5(S=P(NH_2)_2(OH))]$
$K_2[IrCl_5(S=P(NH_2)(OH)_2)]$
$K_2[IrCl_5(S=P(OH)_3)]$
$K_2[IrCl_5(S=P(CN)_3)]$
$K_2[IrCl_5(NH_2C(=S)NH_2)]$
$K_2[IrCl_5(NH_2C(=NH)SCH_3)]$
$K_2[IrCl_5(CH_3NHC(=S)NHCH_3)]$
$K_3[IrCl_5(N(NC)_2)]$
$Cs_3[IrCl_5(N(NC)_2)]$
$K_2[IrCl_5(S(NC)_2)]$
$K_3[IrCl_5(N(SO_2CH_3)_2)]$
$K_3[IrCl_5(N(CN)(SO_2CF_3))]$
$K_2(IrCl_5([1,3,4]\text{-thiadiazole}))$
$K_2[IrCl_5(2,5\text{-dichloro-}[1,3,4]\text{-thiadiazole})]$
$K_2[IrCl_5(2\text{-chloro-5-fluoro-}[1,3,4]\text{-thiadiazole})]$
$K_2[IrCl_5(2,5\text{-difluoro-}[1,3,4]\text{-thiadiazole})]$
$K_2[IrCl_5(2,5\text{-dimercapto-}[1,3,4]\text{-thiadiazole})]$
$K_2[IrCl_5(2,5\text{-disulfamoyl-}[1,3,4]\text{-thiadiazole})]$
$K_2[IrCl_5(2\text{-amino-5-sulfamoyl-}[1,3,4]\text{-thiadiazole})]$
$K_2[IrCl_5(2\text{-fluoro-5-sulfamoyl-}[1,3,4]\text{-thiadiazole})]$
$K_2[IrCl_5([1,2,4]\text{-thiadiazole})]$
$K_2[IrCl_5(3,5\text{-dichloro-}[1,2,4]\text{-thiadiazole})]$ Compounds represented by the formula (B) will next be described specifically.

In the formula (B), N, X and k have the same meanings and fall within the same range as described above in the formula (IV) and m' represents an integer of 1 or 2, preferably 1.

Examples of the compound represented by the formula (B) include, but not limited to, $Na_2[IrCl_5(H_2O)]$, $K_2[IrCl_5(H_2O)]$, $Rb_2[IrCl_5(H_2O)]$, $Cs_2[IrCl_5(H_2O)]$, $Na[IrCl_4(H_2O)_2]$, $K[IrCl_4(H_2O)_2]$, $Rb[IrCl_4(H_2O)_2]$, $Cs[IrCl_4(H_2O)_2]$, $Na_2[IrBr_5(H_2O)]$, $K_2[IrBr_5(H_2O)]$, $Rb_2[IrBr_5(H_2O)]$, $Cs_2[IrBr_5(H_2O)]$, $Na[IrBr_4(H_2O)_2]$, $K[IrBr_4(H_2O)_2]$, $Rb[IrBr_4(H_2O)_2]$, and $Cs[IrBr_4(H_2O)_2]$. Of these, preferred are $K_2[IrCl_5(H_2O)]$ and $Cs[IrCl_4(H_2O)_2]$, with $K_2[IrCl_5(H_2O)]$ being more preferred.

The synthesis processes of the compounds represented by the formula (B) have already been described, for example, in Journal of the American Society (which will hereinafter be abbreviated as J. Am. Chem. Soc.), 84, 2032–2037(1962), Journal of Inorganic and Nuclear Chemistry, 31, 2563–2573 (1969), Journal of Chemical Physics, 22, 2064–2066(1954), and Bulletin de la Societe Chimique de France (which will hereinafter be abbreviated as Bull. soc. chim. France), 6, 1471–1479(1939)). These compounds can be synthesized and isolated. The crystals obtained by these synthesis processes, however are usually complexes having a purity of 70 to 90%. It is reported that purity can be heightened up to 96% even by repeating purification. It is possible to synthesize using such a not highly pure complex as a raw material, but in this case, it is difficult to obtain the product having a purity of 97% by mass (i.e., by weight) or greater. In particular, trace components which adversely affect the photographic performance cannot be removed easily. It has therefore been understood that a raw material of high purity must be used to obtain a high-purity product. It is therefore preferred to use, as a raw material, a high-purity complex of the formula (B) synthesized by the below-described process.

As the raw material for the compound represented by the formula (B), usable are tetravalent iridium hexachloride, tetravalent iridium hexabromide, trivalent iridium hexachloride and trivalent iridium hexabromide.

As the tetravalent iridium to be used as a raw material for the compound of the formula (B), commercially available products can be used. Specific examples include $(NH_4)_2[IrCl_6]$, $Na_2[IrCl_6]$, $K_2[IrCl_6]$, $Rb_2[IrCl_6]$, $Cs_2[IrCl_6]$, $(NH_4)_2[IrBr_6]$, $Na_2[IrBr_6]$, $K_2[IrBr_6]$, $Rb_2[IrBr_6]$, $Cs_2[IrBr_6]$, and $Mg[IrCl_6]$, of which preferred are $(NH_4)_2[IrCl_6]$, $Na_2[IrCl_6]$, $K_2[IrCl_6]$, $(NH_4)_2[IrBr_6]$, $Na_2[IrBr_6]$, and $K_2[IrBr_6]$ and more preferred are $Na_2[IrCl_6]$, $K_2[IrCl_6]$, $Na_2[IrBr_6]$ and $K_2[IrBr_6]$, with $K_2[IrCl_6]$ being especially preferred.

As the trivalent iridium to be used as a raw material for the compound of the formula (B), commercially available products can be used. Specific examples include $(NH_4)_3[IrCl_6]$, $Na_3[IrCl_6]$, $K_3[IrCl_6]$, $Rb_3[IrCl_6]$, $Cs_3[IrCl_6]$, $(NH_4)_3[IrBr_6]$, $Na_3[IrBr_6]$, $K_3[IrBr_6]$, $Rb_3[IrBr_6]$, $Cs_3[IrBr_6]$, and $Mg_{3/2}[IrCl_6]$. Of these, $(NH_4)_3[IrCl_6]$, $Na_3[IrCl_6]$, $K_3[IrCl_6]$, $(NH_4)_3[IrBr_6]$, $Na_3[IrBr_6]$ and $K_3[IrBr_6]$ are preferred and $Na_3[IrCl_6]$, $K_3[IrCl_6]$, $Na_3[IrBr_6]$ and $K_3[IrBr_6]$ are more preferred, with $K_3[IrCl_6]$ being especially preferred.

Conditions for the synthesis of the compound represented by the formula (B) will next be described. The reaction conditions of a tetravalent iridium complex and oxalic acid or salt thereof are as follows.

As oxalic acid or salt thereof to be reacted, a commercially available one can be used. As the salt, alkali metal salt (such as lithium salt, sodium salt, potassium salt, rubidium salt or cesium salt), alkaline earth metal salt (such as magnesium salt or calcium salt) or ammonium (such as ammonium salt or tetraethylammonium salt) is usable. Of these, preferred is an alkali metal salt, more preferably sodium salt, potassium salt or rubidium salt, with potassium salt being most preferred.

Two electrons can be reduced by one oxalic acid molecule so that the reaction can essentially be completed at a molar ratio of oxalic acid or salt thereof to a tetravalent iridium complex of 1:2. It is however preferred to increase the proportion of oxalic acid or salt thereof in order to heighten the purity of the target product. For example, a molar ratio of oxalic acid (or salt thereof): tetravalent iridium preferably falls within a range of 1.1 to 3.0:2, more preferably 1.5 to 2.5:2, especially 1.7 to 2.3:2.

Although any reaction solvent is usable insofar as raw materials are soluble therein, water and alcohols (such as methanol and ethanol) are preferred. At least two of them may be used as a mixture. A water-containing solvent is preferred, with single use of water is most preferred.

According to the literature about the concentration of the tetravalent iridium complex upon reaction, it is the common practice to effect the reaction while adjusting a raw materials/solvent ratio as high as 1 g/20 ml or greater. When the raw materials are dissolved in the solvent, the reaction proceeds at any concentration. The present inventors have found, however, that in order to obtain a high purity product, the concentration of the raw material in the solvent is preferably lower than 1 g/20 ml, more preferably lower than 1 g/25 ml, especially lower than 1 g/30 ml, most preferably lower than 1 g/40 ml. The concentration can be reduced to 1 g/100 ml.

The reaction proceeds at any temperature of 50° C. or higher. When yield, purity and photographic performance are taken in consideration, however, reaction within a range of 50 to 80° C. is preferred. Temperatures lower than 50° C. are not preferred, because at such temperatures, the reaction proceeds very slowly and raw materials adversely affecting the photographic performance tend to remain. At temperatures higher than 80° C., on the contrary, the reaction is completed in a short time, which does not bring about any problem in a small-scale test such as a laboratory level test, but makes it difficult to control the reaction upon large scale production and reduces a yield. At the same time, some components are proved to adversely affect the photographic properties. The sample synthesized at the reaction temperature of more than 80° C. is not preferred. The reaction temperature is more preferably from 55° C. to 75° C., still more preferably from 55° C. to 70° C.

The reaction time can be set at from 1 minute to 3 hours. For the purpose of suppressing the generation of impurities, the reaction time of from 5 minutes to 2 hours is preferred, more preferably from 10 minutes to 1 hour, especially from 15 minutes to 45 minutes.

Then, the reaction conditions when a trivalent iridium complex is used as a raw material will be described specifically.

The reaction solvent is preferably water or a water-containing alcohol (methanol or ethanol), with single use of water is more preferred.

The trivalent iridium complex is used at any concentration upon reaction insofar as it is dissolved in a solvent. In order to obtain the target product in a high purity, a raw material/solvent ratio is preferred to be lower than 1 g/20 ml, more preferably lower than 1 g/30 ml to 1 g/70 ml, especially 1 g/40 ml to 1 g/60 ml.

The reaction temperature is preferably from 40 to 70° C. Temperatures of lower than 40° C. are not preferred from the viewpoint of productivity, because the reaction proceeds slowly and it takes time to complete the reaction. Temperatures exceeding 70° C. are not preferred, because a component adversely affecting the photographic performance increases. The reaction temperature is more preferably from 50° C. to 60° C., still more preferably from 51° C. to 55° C., especially from 52 to 54° C.

The reaction time can be set at from 10 minute to 6 hours. For the purpose of suppressing the generation of impurities, the reaction time from 30 minutes to 120 minutes is preferred, more preferably from 60 minutes to 110 minutes, especially from 80 minutes to 100 minutes.

The target product can be isolated by various methods. Preferred are a crystallization method in which concentration under reduced pressure is followed by cooling; a crystallization method in which addition of a poor solvent is followed by cooling; and combination of these crystallization methods. Of these, more preferred is the crystallization method in which addition of a poor solvent is followed by cooling. As the poor solvent upon crystallization, an alcohol (such as methanol, ethanol or isopropanol), acetonitrile, acetone, ether or tetrahydrofuran is usable, with an alcohol, more preferably methanol or isopropanol, especially isopropanol being preferred. When a purification step is added to such a crystallization method, a target product with higher purity is available.

The addition temperature of the poor solvent upon crystallization is preferably from 0 to 50° C., more preferably from 20 to 45° C., still more preferably from 25 to 35° C. Addition of a poor solvent at temperatures exceeding 50° C. is not preferred, because desensitization occurs upon doping into a silver halide.

The reaction conditions for synthesizing a complex of the formula (IV) by using a compound of the formula (B) as a raw material will next be described specifically.

It is possible to synthesize an iridium complex of the formula (IV) by using a complex of the formula (B) which is not highly pure. Use of a low-purity iridium complex of the formula (B) prepared by the conventional process however made it difficult to obtain a target product having purity of 97% by mass or greater. In particular, trace components adversely affecting the photographic performance cannot be removed easily. The present inventors have found that it is necessary to use, as a raw material, a compound (B) having a high purity. It is therefore most preferred to use, as a raw material, a high-purity complex represented by the formula (B) synthesized by the preparation process as described in the present invention.

Any reaction solvent is usable insofar as the raw material is soluble therein. Preferred examples include water, alcohols (such as methanol and ethanol), and amides (such as dimethylformamide and dimethylacetamide), of which water and dimethylacetamide are more preferred. At least two of these reaction solvents may be used in combination.

The compound of the formula (B) is used at any concentration upon reaction insofar as the raw material is dissolved in a solvent. In order to obtain the target product in a high purity, a raw material/solvent ratio is preferred to be lower than 1 g/10 ml, more preferably 1 g/10 ml to 1 g/70 ml, especially 1 g/15 ml to 1 g/60 ml.

The greater the amount of the ligand represented by Q in the formula (IV) per mol of the compound of the formula (B), the better. The amount is preferably 1 to 100 times the mol, more preferably 1 to 20 times the mol.

The reaction can be conducted at from 10 to 100° C., preferably from 15 to 70° C., more preferably from 20° C. to 50° C., especially from 20 to 35° C.

The reaction time is usually from 30 minute to 7 days, preferably from 1 hour to 3 days, more preferably from 2 hours to 2 days.

The target product can be isolated by a crystallization method by concentration, a crystallization method by the addition of a poor solvent, or combination of these crystallization methods. Of these, preferred are a crystallization method in which concentration under reduced pressure is followed by cooling, a crystallization method in which addition of a poor solvent is followed by cooling, and a combination thereof. The crystallization method in which addition of a poor solvent is followed by cooling is more preferred. Addition of a purification step to the crystallization method makes it possible to obtain the target product with a higher purity.

In the process for preparing a compound of the formula (IV) by using a compound of the formula (B) as a raw material, the below-described synthesizing conditions are preferred in the order of mention.

(1) A preparation process by adding an iridium complex of the formula (B) at a concentration lower than 1 g/10 mol and a ligand in an amount of 1 to 100 moles per mol of an iridium complex and then, heating the resulting mixture to 15 to 70° C. in water or a mixed solution of water and dimethylacetamide.

(2) A preparation process by adding an iridium complex of the formula (B) at a concentration of from 1 g/10 mol to 1 g/70 mol and a ligand in an amount of 1 to 20 moles per mol of the iridium complex and then heating the resulting mixture to 20 to 50° C. in water or a mixed solution of water and dimethylacetamide.

(3) A process for adding an iridium complex of the formula (B) at a concentration of from 1 g/15 mol to 1 g/60 mol and a ligand in an amount of 1 to 20 moles per mol of the iridium complex, heating the resulting mixture to 20 to 35° C. in water or a mixed solution of water and dimethylacetamide, and without concentrating the reaction mixture, adding a poor solvent to precipitate crystals.

When a complex of the formula (IV) is added to a photographic silver halide emulsion, it is preferably added in an amount of from $1\times10^{-10}$ mols to $1\times10^{-4}$ mols, more preferably from $1\times10^{-9}$ mols to $1\times10^{-5}$ mols, each per mol of silver.

When the above-described complex is incorporated in silver halide grain, it is preferred to uniformly incorporate it inside of the grain. It is also preferred to allow it to exist only on the surface layer of the grain or alternatively, to allow it exist only inside of the grain and add a complex-free layer to the surface of the grain as disclosed in Japanese Patent (Application) Laid-Open No. 208936/1992, 125245/1990 or 188437/1991. As disclosed in U.S. Pat. No. 5,252,451 or 5,256,530, it is also preferred to carry out physical ripening of a complex with fine grain incorporated in the grain, thereby modifying the surface phase of the grain. The above-described methods may be used in combination, or a plurality of complexes may be incorporated in silver halide grain. There is no particular limitation imposed on the halogen composition at the position in which the complex is incorporated and the complex can be added to any one of silver chloride layer, silver chlorobromide layer, silver bromide layer, silver chloroiodide layer and silver bromoiodide layer.

It is preferred to add the complex directly to the reaction mixture upon formation of silver halide grain; or to add it to an aqueous halide solution for the formation of silver halide grain or to another solution, then adding to the reaction mixture for the grain formation, thereby incorporating it in silver halide grain. Combined use of these methods is also preferred. As iridium ion which is a central metal (ion), either a trivalent one or tetravalent one is usable, but the former one is preferred. The iridium trivalent complex is easily subjected to oxidation so that a reducing agent is added in advance to the solution to be added to an emulsion. Preferred examples of the reducing agent include reductones, hydrazines, hydroxylamines, hydroxysemicarbazides, hydroxyurethanes, hydroxyureas, hydroxamic acids, compounds having a vitamin-E-analogous skeleton, phenylenediamines, phenidones, hydrazides and phenols. Of these, reductones are most preferred.

The silver halide grain in the silver halide photographic emulsion for use in the present invention is preferably a cubic or tetradecahedral crystal grain (the grain may have a rounded peak or may have (hk1) planes faces) having substantially {100} faces, an octahedral crystal grain, or a tabular grain having, as at least 50% of the whole projected area, {100} faces or {111} faces and having an aspect ratio of 2 or more. The term "aspect ratio" as used herein means a value obtained by dividing the diameter of a circle having an area equivalent to the projected area by the thickness of the grain. In the present invention, cubic grains or tabular grains having {100} faces or {111} faces as main planes are preferably used.

As the silver halide emulsion for use in the present invention, silver chloride, silver bromide, silver bromoiodide or silver chlorobromoiodide emulsions are used. For rapid processing, silver chloride, silver chlorobromide, silver chloroiodide or silver chlorobromoiodide emulsion having a silver chloride content of 95 mol % or greater, more preferably 98 mol % or greater, are preferably used. Of these silver halide emulsions, emulsions having, at the shell portion of the silver halide grains, 0.01 to 0.50 mol %, more preferably 0.05 to 0.40 mol % per mol of the total silver, of a silver chloride iodide phase are preferred because high sensitivity and excellent high intensity exposure suitability can be attained. Further, silver halide grains having a silver bromide localized phase of from 0.2 to 5 mol %, more preferably from 0.5 to 3 mol %, per mol of the total silver, on the surfaces of the silver halide grains are particularly preferred because both high sensitivity and stabilization of photographic performances can be attained.

When the emulsion of the present invention contains silver iodide, the iodide ion may be introduced by adding a solution of an iodide salt alone, or a solution of an iodide salt together with a silver salt solution and a high chloride salt solution. In the latter case, the iodide salt solution and the high chloride salt solution may be added separately or as a mixed solution thereof. An iodide salt is added in the form of a soluble salt such as an alkali or alkaline earth iodide salt. Further, an iodide can be introduced by causing cleavage of an iodide ion from an organic molecule as disclosed in U.S. Pat. No. 5,389,508. Or, as another iodide ion source, silver iodide fine grains may be used.

The iodide salt solution may be added intensively at one time of grain formation or may be added over a certain period of time. For obtaining an emulsion having high sensitivity and low fog, the introduction position of an iodide ion to a high chloride emulsion is restricted. The deeper the iodide ion is introduced into the emulsion grain, the smaller is the increment of sensitivity. Accordingly, the addition of an iodide salt solution is preferably started at 50% or outer side of the grain volume, more preferably 70% or outer side, and most preferably 80% or outer side. Moreover, the addition of an iodide salt solution is preferably finished at 98% or inner side of the grain volume, and most preferably 96% or inner side. When the addition of an iodide salt solution is finished at a little inner side of the grain surface, an emulsion having higher sensitivity and lower fog can be obtained.

Electron-releasing time can be determined either by using a reciprocity failure curve or by the double flash photoconduction method. In the present invention, the former one is employed. The reciprocity failure curve can be drawn as shown in "Shashin Kogaku no Kiso, Ginen Shashin-hen", edited by Nihon Shashin Gakkai (The Society of Photographic Science and Technology of Japan), page 297. In the ordinary silver halide emulsion, particularly silver chloride emulsion, desensitization occurs on the low illumination and high illumination sides, with the maximum sensitivity in the vicinity of the medium illumination side, thus forming a curve convex downward. The reciprocity law failure curve of an emulsion doped with an electron-releasing dopant and thereby improved in the failure of the reciprocity law has a desensitization-free flat region on the side of illumination higher than a certain exposure illumination. This curve is different from that of a non-doped emulsion. The exposure time at the exposure illumination from which a flat region starts to appear, that is, the exposure time at the exposure illumination from which a difference from the characteristic curve of non-doped emulsion appears is designated as electron-releasing time. Electron-releasing (photoelectron-releasing) effect appears for the first time when exposure is finished so that the time when electron-releasing effect appears photographically can be defined as the photoelectron-release starting time, that is, electron-releasing time.

The distribution of an iodide ion content in the depth direction of a grain can be measured by an etching/TOF-SIMS (Time of Flight∩Secondary Ion Mass Spectrometry) method by using, for example, Model TRIFT TOF-SIMS apparatus (manufactured by Phi Evans Co.). A TOF-SIMS method is specifically described in Nippon Hyomen Kagakukai (ed.), "Hyomen Bunseki Gijutsu Sensho Niji Ion Shitsuryo Bunsekiho (Surface Analysis Technique Selection-Secondary Ion Mass Analytical Method)", published by Maruzen Co., Ltd. (in 1999). Analysis of emulsion grain by the etching/TOF-SIMS method reveals that even if the addition of an iodide salt solution is finished inside of the grain, an iodide ion oozes toward the surface of the grain. When the emulsion of the present invention contains silver iodide, it is preferred that as a result of analysis by the etching/TOF-SIMS method, the iodide ion exhibits concentration maximum on the grain surface and the iodide ion concentration decreases toward the inside.

When the emulsion according to the present invention contains a silver bromide localized phase, it is preferred to form the silver bromide localized phase having a silver bromide content of 10 mol % or greater by epitaxial growth on the grain surface. The silver bromide content of the silver bromide localized phase is preferably from 10 to 60 mol %, and most preferably from 20 to 50 mol %. The silver bromide localized phase preferably has 0.1 to 5 mol %, more preferably 0.3 to 4 mol %, of silver based on the total silver amount constituting the silver halide grain of the present invention. In the silver bromide localized phase, metal complex ions belonging to the group VIII of the Periodic Table such as iridium (III) chloride, iridium (III) bromide, iridium (IV) chloride, sodium hexachloroiridate (III), potassium hexachloroiridate (IV), hexammineiridium (IV) salt, trioxalatoiridium (III) salt and trioxalatoiridium (IV) salt are preferably incorporated. Although the amount of these compounds falls within a wide range according to their purpose, it is preferably from $10^{-9}$ to $10^{-2}$ mol per mol of silver halide.

In the present invention, a transition metal ion can be added during formation and/or growth of a silver halide grain and incorporated inside and/or surface of the silver halide grain. As the metal ion, preferred are transition metal ions, of which iron, ruthenium, iridium, osmium, lead, cadmium and zinc are preferred. Use of these metal ions as six-coordinated octahedral complexes having a ligand is more preferred. When inorganic compounds are used as the ligand, a cyanide ion, a halide ion, thiocyan, a hydroxide ion, a peroxide ion, an azide ion, a nitrous acid ion, water, ammonia, a nitrosyl ion, and a thionitrosyl ion are preferably used. They can be coordinated with any one of the above-described metal ions such as iron, ruthenium, iridium, osmium, lead, cadmium and zinc. It is also preferred to use a plurality of ligands in one complex molecule. Organic compounds can also be used as the ligand. Preferred examples of the organic compounds include chain compounds having, in the main chain thereof, 5 or less carbon atoms and/or 5- or 6-membered heterocyclic compounds.

In the present invention, the complex of the present invention or a complex usable therewith in combination can be incorporated into a silver halide grain by directly adding it to a reaction solution upon formation of the silver halide grain, or adding to an aqueous halide solution for forming silver halide grains or another solution in advance and then adding the resulting mixture to a reaction solution for forming silver halide grains. The complex can also be incorporated into a silver halide grain by using these methods in combination.

When these complexes are incorporated into a silver halide grain, they are preferably incorporated into the inside of a grain uniformly. As disclosed in Japanese Patent Laid-Open Nos. 208936/1992, 125245/1990 or 188437/1991, it is also preferred to allowed them to exist only in the grain surface layer, or to add a complex-free layer to the grain surface while allowing the complex to exist only inside of the grain. Further, as disclosed in U.S. Pat. No. 5,252,451 or 5,256,530, it is preferred to carry out physical ripening with fine grains having a complex incorporated therein, thereby modifying the grain surface phase. These methods can be used in combination. A plurality of complexes may be incorporated into one silver halide grain. The halogen composition at the position into which the above complexes are incorporated is not particularly limited, and the complexes may be incorporated into any of a silver chloride layer, a silver chlorobromide layer, a silver bromide layer, a silver chloroiodide layer and a silver bromoiodide layer.

The silver halide grains contained in the silver halide emulsion for use in the present invention preferably have an average grain size (the diameter of a circle having an area equivalent to the projected area of the grain is designated as a grain size and number average of the diameters is taken as an average grain size) of from 0.1 $\mu$m to 2 $\mu$m.

The grain size distribution of these grains is preferably so-called monodispersed one having a variation coefficient (the value obtained by dividing the standard deviation of grain size distribution by an average grain size) of 20% or less, preferably 15% or less, and more preferably 10% or less. It is also preferred to use the above-described monodispersed emulsion by blending it in the same layer or multi-layer coating in order to achieve a broad latitude.

To the silve rhalide emulsion used in the present invention, various compounds or precursors thereof can be added for the purpose of preventing fogging or stabilizing the photographic performances during production, storage or processing of the photosensitive material. For this purpose, the compounds described in the above-described Japanese Patent Laid-Open No. 215272/1987, pp. 39 to 72 are preferably used. A 5-arylamino-1,2,3,4-thiatriazole compound (the aryl residue of this compound has at least one electron attracting group) described in EP 0447647 is also preferred.

In order to heighten the storage stability of the silver halide emulsion, the following are also preferably used in the present invention. They are hydroxamic acid derivatives described in Japanese Patent Laid-Open No. 109576/1999; cyclic ketones described in Japanese Patent Laid-Open No. 327094/1999 and having a double bond substituted, at both terminals thereof, with an amino group or a hydroxyl group adjacent to the carbonyl group (particularly those represented by the formula (S1) and the paragraphs of from 0036 to 0071 therein may be incorporated into the specification of the present application); sulfo-substituted catechols and hydroquinones described in Japanese Patent Laid-Open No. 143011/1999 (such as 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof); and water-soluble reducing agents represented by formulae (I) to (III) of Japanese Patent Laid-Open No. 102045/1999.

Spectral sensitization is performed in order to give spectral sensitivity to a desired optical wavelength region for the emulsion in each layer of the photosensitive material of the present invention.

Examples of the spectral sensitizing dye usable for spectral sensitization of blue, green and red regions in the photosensitive material of the present invention include compounds described in "Heterocyclic compounds—Cyanine dyes and related compounds" by F. M. Harmer (published by John Wiley & Sons [New York, London] in 1964).

As specific examples of the compounds and the spectral sensitization method, those described in the above-mentioned Japanese Patent Laid-Open No. 215272/1987, from the upper right column, page 22 to page 38 are preferred. As red-sensitive spectral sensitizing dyes of silver halide emulsion grains having a particularly high silver chloride content, spectral sensitizing dyes described in Japanese Patent Laid-Open No. 123340/1991 are much preferred from the viewpoints of stability, intensity of adsorption, and temperature-dependency of exposure.

The amount of these spectral sensitizing dyes falls within a wide range according to purposes, and is used in an amount of from $1\times10^{-8}$ mol to $8\times10^{-1}$ mol, preferably from $0.5\times10^{-6}$ mol to $1.0\times10^{-2}$ mol, more preferably from $1.0\times10^{-6}$ mol to $5.0\times10^{-3}$, per mol of the silver halide.

The silver halide emulsion for use in the present invention is usually chemically sensitized. For chemical sensitization, sulfur sensitization typified by the addition of a labile sulfur compound, noble metal sensitization typified by gold sensitization, and reduction sensitization can be used singly or in combination. As the compound used for chemical sensitization, the compounds as described in Japanese Patent Laid-Open No. 215272/1987, right lower column, p. 18 to right upper column, p. 22 are preferably used. A silver halide emulsion subjected to gold sensitization is particularly preferred in the present invention, because fluctuations in photographic performances upon scanning exposure to a laser light can be lessened further by gold sensitization.

For gold sensitization of the silver halide emulsion used in the present invention, various inorganic gold compounds, gold (I) complexes having an inorganic ligand and gold (I) compounds having an organic ligand can be preferably employed. As the inorganic gold compounds, chloroauric acid and salts thereof, and as the gold (I) complexes having an inorganic ligand, dithiocyanic acid gold compounds such as potassium dithiocyanatoaurate (I), and trisodium dithiosulfatoaurate (I) are preferably used.

Preferred examples of the gold (I) compounds having an organic ligand include bisgold (I) mesoionic heterocycles such as gold (I) tetrafluoroborate bis (1,4,5-trimethyl-1,2,4-triazolium-3-thiolato) described in Japanese Patent Laid-Open No. 267249/1992, organic mercapto gold (I) complexes such as potassium bis(1-[3-(2-sulfonatobenzamido)-phenyl]-5-mercaptotetrazole potassium salt)aurate (I) pentahydrate described in Japanese Patent Laid-Open No. 218870/1999, and gold (I) compounds coordinated with a nitrogen compound anion such as bis(1-methylhydantoinato) gold (I) sodium salt tetrahydrate described in Japanese Patent Laid-Open No. 268550/1992. Also preferred are gold (I) thiolate compounds described in U.S. Pat. No. 3,503,749, gold compounds described in Japanese Patent Laid-Open No. 69074/1996, Japanese Patent Laid-Open No. 69075/1996 and Japanese Patent Laid-Open No. 269554/1998, and compounds described in U.S. Pat. Nos. 5,620,841, 5,912,112, 5,620,841, 5,939,245 and 5,192,111.

Although the amount of these compounds falls within a wide range depending on the case, it is from $5\times10^{-7}$ to $5\times10^{-3}$ mol, preferably from $5\times10^{-6}$ to $5\times10^{-4}$ mol, per mol of silver halide.

Use of colloidal gold sulfide is also preferred. Its preparation process is described in Research Disclosure, 37154; Solid State Ionics, 79, 60–66(1995); and Compt. Rend. Hebt. Seances, Acad. Sci. Sect. B, 263, 1328(1966). Colloidal gold sulfides with various sizes are usable, but those having a grain size of 50 nm or less are preferred. Although the amount of colloidal gold sulfide falls within a wide range depending on the case, it is preferably from $5\times10^{-7}$ mol to $5\times10^{-3}$ mol, more preferably from $5\times10^{-6}$ mol to $5\times10^{-4}$ mol, per mol of silver halide.

In the present invention, gold sensitization may be combined with other sensitization methods, for example, sulfur sensitization, selenium sensitization, tellurium sensitization, reduction sensitization, or noble metal sensitization using a compound other than gold compounds.

Conventionally known photographic materials and additives can be used for the silver halide photosensitive material of the present invention. As a photographic support, for example, a support of a transmission type and a support of a reflection type may be used. Preferred examples of the transmission type support include transparent films such as cellulose nitrate film and polyethylene terephthalate film, and polyester of 2,6-naphthalenedicarboxylic acid (NDCA) with ethylene glycol (EG) and polyester of NDCA with terephthalic acid and EG, each having, formed thereon, an information recording layer such as a magnetic layer. As the reflection type support, preferred are those laminated with a plurality of water resistant resin layers such as polyethylene or polyester layers at least one of which contains a white pigment such as titanium oxide.

A more preferred reflective support in the present invention is a paper substrate having, on the side on which a silver halide emulsion layer is disposed, a polyolefin layer with minute pores. The polyolefin layer may be composed of a plurality of layers, and in this case, more preferred is a paper substrate in which a polyolefin (such as polypropylene or polyethylene) layer on the side nearer to the paper substrate has minute pores while another polyolefin (such as polypropylene or polyethylene) layer adjacent to the gelatin layer on the silver halide emulsion layer side has no minute pores. The density of the above-described polyolefin layer(s) provided between the paper substrate and photographic constituent layers is preferably from 0.40 to 1.0 g/ml, more preferably from 0.50 to 0.70 g/ml. The thickness of the polyolefin layer(s) provided between the paper substrate and photographic constituent layers is preferably from 10 to 100 $\mu$m, more preferably from 15 to 70 $\mu$m. The thickness ratio of the polyolefin layer to the paper substrate is preferably from 0.05 to 0.5, more preferably from 0.1 to 0.2.

In order to heighten the rigidity of the reflective support, it is also preferred to dispose a polyolefin layer on the side of the paper substrate opposite to the side on which photographic constituent layers are provided (the back side). In this case, the backing polyolefin layer is preferably polyethylene or polypropylene having a mat surface, more preferably the polypropylene. The thickness of the backing polyolefin layer is preferably from 5 to 50 $\mu$m, more preferably from 10 to 30 $\mu$m, and its density is preferably from 0.7 to 1.1 g/ml. The preferred embodiments of the polyolefin layer disposed on the paper substrate in the reflective support in the present invention are described in Japanese Patent Laid-Open Nos. 333277/1998, 333278/1998, 52513/1999, and 65024/1999, and EP 0880065 and EP 0880066.

To the above-described water resistant resin layer, a fluorescent brightener is preferably added. The fluorescent brightener may be dispersed in a hydrophilic colloid layer of a photosensitive material. Preferred examples of the fluorescent brightener include benzoxazole-based, coumarin-based and pyrazoline-based ones. Benzoxazolylnaphthalene-based and benzoxazolylstilbene-based ones are more preferred. Although no limitation is imposed on its using amount, that from 1 to 100 mg/m$^2$ is preferred. When it is mixed in a water resistant resin, it is preferably added in an amount of from 0.0005 to 3% by mass, more preferably from 0.001 to 0.5% by mass, based on the resin.

The reflective support may be a transmission type support or a reflective support as described above having, formed thereon, a hydrophilic colloid layer containing a white pigment. The reflective support may also be a support having a metal surface of a mirror plane reflectivity or a diffuse reflectivity of type 2.

As the support employed for the photosensitive material of the present invention, a white polyester-based support or a support having a white-pigment-containing layer provided on the side thereof on which a silver halide emulsion layer is provided may be used for display. It is preferred to apply an antihalation layer on the silver-halide-emulsion-layer coated side of the support or the backside of the support in order to improve sharpness. In particular, it is preferred to set the transmission density through the support within a range of from 0.35 to 0.8 to permit viewing of a display both with a reflected light or a transmitted light.

In the photosensitive material according to the present invention, for the purpose of increasing the sharpness of an image, it is preferred to add, to the hydrophilic colloid layer, the dye decolorable by processing (particularly, an oxonol dye) as described in EP-A-0337490, pp. 27 to 76 so as to make the optical reflection density of the photosensitive material at 680 nm 0.70 or greater, or to incorporate at least 12% by mass (preferably at least 14% by mass) of titanium oxide surface-treated with dihydric to tetrahydric alcohols (e.g., trimethylolethane) in the water resistant resin layer of the support.

In the photosensitive material according to the present invention, for the purpose of preventing irradiation or halation, or improving safety of a safe light, it is preferred to add the dye decolorable by processing (particularly, an oxonol dye or a cyanine dye) as described in EP-A-0337490, pp. 27 to 76 to the hydrophilic colloid layer. The dyes described in EP 0819977 are also preferably used in the present invention.

Some of these water soluble dyes deteriorate color separation or safety of a safe light when used in an increased amount. As the dye usable without deteriorating color separation, the water-soluble dyes described in Japanese Patent Laid-Open Nos. 127324/1993, 127325/1993 and 216185/1993 are preferred.

In the present invention, a coloring layer decolorable by processing can be used in stead of a water soluble dye or in combination therewith. The coloring layer decolorable by processing may be in direct contact with the emulsion layer or may be arranged so as to be in contact with the emulsion layer via an intermediate layer containing gelatin or a color mixing preventive such as hydroquinone. The coloring layer is preferably disposed below the emulsion layer (on the support side of the emulsion layer) which colors in the same type of elementary color as the colored layer. It is possible to provide every coloring layer corresponding to each elementary color or only a part selected as needed. It is also possible to provide a coloring layer colored in colors corresponding to a plurality of elementary color regions. The optical reflection density of a coloring layer is preferably such that the optical density value at the wavelength permitting the highest optical density in the wavelength region used in exposure (a visible light region of from 400 nm to 700 nm in general printer exposure, and the wavelength of the scanning exposure light source when used for scanning exposure) is preferably from 0.2 to 3.0, more preferably from 0.5 to 2.5, and particularly preferably from 0.8 to 2.0.

The coloring layer can be formed by the conventionally known process. Examples of the process include the process of incorporating a dye in the form of a solid fine particle dispersion to a hydrophilic colloid layer as that employed for preparing the dyes described in Japanese Patent Laid-Open No. 282244/1990, from upper right column, p. 3 to p. 8, or the dyes described in Japanese Patent Laid-Open No. 7931/1991, right upper column, p. 3 to lower left column, p. 11; a process of mordanting a cationic polymer with an anionic dye; a process of causing a dye to adsorb to fine grains of silver halide or the like and fixing into a layer; and a process of using colloid silver as described in Japanese Patent Laid-Open No. 239544/1989. As the process of dispersing the fine particles of a dye in a solid state, that of adding a fine-grain dye which is substantially water insoluble at pH 6 or less but is substantially water soluble at pH 8 or more is described in Japanese Patent Laid-Open No. 308244/1990, pp. 4 to 13. The process of mordanting a cationic polymer with an anionic dye is described isclosed in Japanese Patent Laid-Open No. 84637/1990, pp. 18 to 26. The preparation process of colloid silver as a light absorber is shown in U.S. Pat. Nos. 2,688,601 and 3,459,563. Of these processes, the process of incorporating a fine-grain dye and that of using colloid silver are preferred.

The silver halide photosensitive material according to the present invention can be used for a color negative film, a color positive film, a color reversal film, a color reversal printing paper and a color printing paper. Of these, use as a color printing paper is preferred.

The color printing paper preferably has a yellow-coloring silver halide emulsion layer, a magenta-coloring silver halide emulsion layer, and a cyan-coloring silver halide emulsion layer, each at least one. These silver halide emulsion layers are usually arranged in the order of a yellow-coloring silver halide emulsion layer, a magenta-coloring silver halide emulsion layer, and a cyan-coloring silver halide emulsion layer from the side nearer to the support.

However, the layer constitution may be different from the above. Although the silver halide emulsion layer containing a yellow coupler may be arranged anywhere on a support, when the yellow-coupler-containing layer contains silver halide tabular grains, the yellow coupler-containing layer is preferably disposed farther, from the support, than at least one of the magenta coupler-containing silver halide emulsion layer and the cyan coupler-containing silver halide emulsion layer. From the viewpoints of acceleration of chromogenic development, acceleration of desilvering and a reduction in residual color by sensitizing dyes, the yellow coupler-containing silver halide emulsion layer is preferably formed at the position farthest from the support relative to the other silver halide emulsion layers. Moreover, for reducing Blix discoloration, the cyan coupler-containing silver halide emulsion layer is preferably a middle layer of the other silver halide emulsion layers, and for reducing discoloration due to light, the cyan coupler-containing silver halide emulsion layer is preferably a lowermost layer. Each of yellow, magenta and cyan color-forming layers may comprise two or three layers. For example, it is also preferred to dispose a silver-halide-emulsion-free coupler layer contiguously to a silver halide emulsion layer to form a coloring layer, as disclosed in Japanese Patent Laid-Open Nos. 75055/1992, 114035/1997, and 246940/1998 and U.S. Pat. No. 5,576,159.

As the silver halide emulsions, other materials (such as additives), and photographic constituent layers (including layer arrangement) used in the present invention; and processes and additives employed for processing of these photosensitive materials, preferred are those described in Japanese Patent Laid-Open No. 215272/1987, Japanese Patent Laid-Open No. 33144/1990 and EP-A-0355660, with those disclosed in EP-A-0355660 being especially preferred. Also preferred are the silver halide color photosensitive materials and the processing methods thereof as described in Japanese Patent Laid-Open Nos. 34889/1993, 359249/1992, 313753/1992, 270344/1992, 66527/1993, 34548/1992, 145433/1992, 854/1990, 158431/1989, 90145/1990, 194539/1991, and 93641/1990, and EP-A-0520457.

In the present invention, as the above-described reflective supports and silver halide emulsions as well as the kind of foreign metal ions to be doped in silver halide grains, storage stabilizers and antifoggants for silver halide emulsions, chemical sensitization methods (sensitizers), spectral sensitization methods (spectral sensitizers), cyan-, magenta- and yellow-couplers and emulsifying/dispersing methods therefor, color image storage improvers (antistaining agents and fading inhibitors), dyes (coloring layers), kinds of gelatins, the layer constitution of the photosensitive material and pH of the coated films of photosensitive materials, those described in the patents listed in the following Tables 1 and 2 are particularly preferably used.

In addition to those described in Tables 1 and 2, cyan, useful are magenta and yellow couplers described in Japanese Patent Laid-Open No. 215272/1987, page 91, upper right column, line 4 to page 121, upper left column, line 6; Japanese Patent Laid-Open No. 33144/1990, page 3, upper right column, line 14 to page 18, left upper column, the last line, and page 30, upper right column, line 6 to page 35, lower right column, line 11; and EP-A-355660, page 4, lines 15 to 27, page 55, line 30 to page 28, the last line, page 45, lines 29 to 31, and page 47, line 23 to page 63, line 50.

Also, in the present invention, the compound represented by formula (II) or (III) in WO-98/33760 and the compound represented by formula (D) in Japanese Patent Laid-Open No. 221825/1998 may be preferably added.

TABLE 1

| Element | Japanese Patent Laid-Open No. 104448/1995 | Japanese Patent Laid-Open No. 77775/1995 | Japanese Patent Laid-Open No. 301895/1995 |
| --- | --- | --- | --- |
| Reflective support | column 7, line 12 to column 12, line 19 | column 35, line 43 to column 44, line 1 | column 5, line 40 to column 9, line 26 |
| Silver halide emulsion | Column 72, line 29 to Column 74, line 18 | Column 44, line 36 to Column 46, line 29 | Column 77, line 48 to Column 80, line 28 |
| Kind of foreign metal ion | Column 74, line 19 to line 44 | Column 46, line 30 to Column 47, line 5 | Column 80, line 29 to Column 81, line 6 |
| Storage stabilizer or antifoggant | Column 75, line 9 to line 18 | Column 47, line 20 to Line 29 | Column 18, line 11 to Column 31, line 37 (particularly, a mercaptoheterocyclic compound) |
| Chemical sensitizing method (chemical sensitizer) | Column 74, line 45 to Column 75, line 6 | Column 47, line 7 to Line 17 | Column 81, line 9 to line 17 |
| Spectral sensitizing method (spectral sensitizer) | Column 75, line 19 to Column 76, line 45 | Column 47, line 30 to Column 49, line 6 | Column 81, line 21 to Column 82, line 48 |
| Cyan coupler | Column 12, line 20 to Column 39, line 49 | Column 62, line 50 to line 16 | Column 88, line 49 to Column 89, line 16 |
| Yellow coupler | Column 87, line 40 to Column 88, line 3 | Column 63, line 17 to line 30 | Column 89, line 17 to line 30 |
| Magenta coupler | Column 88, line 4 to line 18 | Column 63, line 3 to Column 64, line 11 | Column 31, line 34 to Column 77, line 44 & Column 88, line 32 to line 46 |

TABLE 2

| Element | Japanese Patent Laid-Open No. 104448/1995 | Japanese Patent Laid-Open No. 77775/1995 | Japanese Patent Laid-Open No. 301895/1995 |
| --- | --- | --- | --- |
| Emulsifying/dispersing method of coupler | Column 71, line 3 to Column 72, line 11 | Column 61, line 36 to line 49 | Column 87, line 35 to line 48 |
| Color image storing improver (antistaining agent) | Column 39, line 50 to Column 70, line 9 | Column 61, line 50 to Column 62, line 49 | Column 87, line 49 to Column 88, line 48 |
| Fading inhibitor | Column 70, line 10 to Column 71, line 2 | | |
| Dye (colorant) | Column 77, line 42 to Column 78, line 41 | Column 7, line 14 to Column 19, line 42 & Column 50, line 3 to Column 51, line 14 | Column 9, line 27 to Column 18, line 10 |
| Kind of gelatin | Column 78, line 42 to line 48 | Column 51, line 15 to line 20 | Column 83, line 13 to line 19 |
| Layer constitution of photosensitive material | Column 39, line 11 to line 26 | Column 44, line 2 to line 35 | Column 31, line 38 to Column 32, line 33 |
| pH of film of photosensitive material | Column 72, line 12 to line 28 | | |
| Scanning exposure | Column 76, line 6 to Column 77, line 41 | Column 49, line 7 to Column 50, line 2 | Column 82, line 49 to Column 83, line 12 |
| Preservative in developer solution | Column 88, line 19 to Column 89, line 22 | | |

These couplers will be described below in further detail. As a cyan coupler usable in the present invention, pyrrolotriazole couplers are preferred, of which the couplers represented by formula (I) or (II) in Japanese Patent Laid-Open No. 313324/1993, the couplers represented by formula (I) in Japanese Patent Laid-Open No. 347960/1994, and the couplers exemplified in these patents are particularly preferred. Phenol-based and naphthol-based cyan couplers, for example, the cyan couplers represented by formula (ADF) in Japanese Patent Laid-Open No. 333297/1998 are preferred.

In addition, the pyrroloazole type cyan couplers as described in EP 0488248 and EP-A0491197, the 2,5-diacylaminophenol couplers as described in U.S. Pat. No. 5,888,716, and the pyrazoloazole type cyan couplers having, at the 6-position thereof, an electron attractive group and a hydrogen bonding group as described in U.S. Pat. Nos. 4,873,183 and 4,916,051, in particular, the pyrazoloazole type cyan couplers having, at the 6-position thereof, a carbamoyl group as described in Japanese Patent Laid-Open Nos. 171185/1996, 311360/1996 and 339060/1996 are also preferred.

In addition to the diphenylimidazole-based cyan couplers described in Japanese Patent Laid-Open No. 33144/1990, also usable are the 3-hydroxypyridine-based cyan couplers described in EP-A-0333185 (with Coupler (42), that is a 4-equivalent coupler rendered 2-equivalent by having a chlorine releasing group, and Couplers (6) and (9), cited as specific examples being particularly preferred), the cyclic active methylene-based cyan couplers described in Japanese Patent Laid-Open No. 32260/1989 (with Couplers 3, 8 and 34 cited as specific examples being particularly preferred), the pyrrolopyrazole type cyan couplers described in EP-A-0456226, and the pyrroloimidazole type cyan couplers disclosed in EP 0484909.

As the magenta couplers, usable in the present invention are the 5-pyrazolone-based magenta couplers and the pyrazoloazole-based magenta couplers as described in the above-described patents in the tables. Of these, preferred are the pyrazolotriazole couplers having a secondary or tertiary alkyl group directly bonded to the 2-, 3- or 6-position of the pyrazolotriazole ring as described in Japanese Patent Laid-Open No. 65245/1986, the pyrazoloazole couplers having, in the molecule thereof, a sulfonamido group as described in Japanese Patent Laid-Open No. 65246/1986, the pyrazoloazole couplers having an alkoxyphenylsulfonamido ballast group as described in Japanese Patent Laid-Open No. 147254/1986, and the pyrazoloazole couplers having, at the 6-position thereof, an alkoxy group or an aryloxy group as described in EP-A-226849 and EP-A-294785. In particular, the pyrazoloazole coupler represented by formula (M-I) in Japanese Patent Laid-Open No. 122984/1996 is preferred, and the description in paragraphs 0009 to 0026 can be applied as is to the present invention and can be used as a part of the specification of the present invention. In addition, the pyrazoloazole couplers having, at both of the 3- and 6-positions thereof, steric hindrance groups as described EP 854384 or EP 884640 are also preferably used.

As the yellow couplers, preferred are, in addition to the compounds described in the above table, the acylacetamide type yellow couplers having, in the acyl group thereof, a 3- to 5-membered cyclic structure as described in EP-A-0447969, the malondianilide type yellow couplers having a cyclic structure as described in EP-A-0482552, the acylacetamide type yellow couplers having a dioxane structure as described in U.S. Pat. No. 5,118,599. Of these, the acylacetamide type yellow coupler having, as an acyl group, a 1-alkyl-cyclopropane-1-carbonyl group and the malondianilide type yellow coupler, one anilide of which constitutes an indoline ring are particularly preferred. These couplers may be used either singly or in combination.

It is preferred to impregnate the coupler used in the present invention with a loadable latex polymer (for example, that described in U.S. Pat. No. 4,203,716) in the presence (or absence) of the high boiling point organic solvent described in the above table, or dissolve it together with a polymer which is insoluble in water but soluble in an organic solvent and then emulsify and disperse the resulting solution or the like in a aqueous solution of hydrophilic colloid. Preferred examples of polymer insoluble in water but soluble in an organic solvent include the homopolymers and copolymers described in U.S. Pat. No. 4,857,449, from columns 7 to 15, and WO 88/00723, pp. 12 to 30. In view of color image stability, more preferred are methacrylate-based or acrylamide-based polymers, with acrylamide-based polymers being especially preferred. are preferred.

In the present invention, known color mixing preventives can be used. Of these, those described in the below-described patents are particularly preferred. Examples include the high molecular weight redox compounds described in Japanese Patent Laid-Open No. 333501/1993, the phenidone and hydrazine compounds described in WO 98/33760 and U.S. Pat. No. 4,923,787, and the white couplers described in Japanese Patent Laid-Open No. 249637/1993, Japanese Patent Laid-Open No. 282615/1998 and German Patent No. 19629142A1. When the pH of a developer is increased to carry out speedy development, use of the redox compounds described in German Patent No. 19618786A1, EP-A-839623, EP-A-842975, German Patent 19806846A1 and French Patent 276046A1 are also preferred.

In the present invention, use of a compound having a triazine skeleton and having a high molar absorption coefficient as an ultraviolet absorber is preferred. For example, usable are compounds in the following patents: Japanese Patent Laid-Open Nos. 3335/1971, 152776/1980, 197074/1993, 232630/1993, 307232/1993, 211813/1994, 53427/1996, 234364/1996, 239368/1996, 31067/1998, 115898/1998, 147577/1998, and 182621/1998, German Patent 19739797A, EP-A-711804 and JP-W-501291/1996.

For the photosensitive material of the present invention, use of gelatin as a binder or a protective colloid is effective. Protective colloids other than gelatin are also usable either singly or in combination with gelatin. The content of heavy metals, such as iron, copper, zinc and manganese, contained in the gelatin as impurities are contained as impurities is preferably 5 ppm or less, more preferably 3 ppm or less. The amount of calcium contained in the photosensitive material is preferably 20 mg/m$^2$ or less, more preferably 10 mg/m$^2$ or less, and most preferably 5 mg/m$^2$ or less.

In the present invention, in order to prevent various kinds of molds or bacteria from proliferating in a hydrophilic colloid layer and deteriorating images, fungicides and biocides as described in Japanese Patent Laid-Open No. 271247/1988 are preferably added.

The pH of the film of the photosensitive material is preferably from 4.0 to 7.0, more preferably from 4.0 to 6.5.

In the present invention, a surfactant can be added to the photosensitive material for improving coating stability, preventing generation of static electricity and adjusting the quantity of electrostatic charge. The examples of the surfactant include anionic, cationic, betaine and nonionic-based surfactants, more specifically, those described in Japanese Patent Laid-Open No. 333492/1993. Fluorine-containing surfactants are especially preferred.

Although no particular limitation is imposed on the amount of the surfactant added to the photosensitive material, it is usually from $1\times10^{-5}$ to $1$ g/m$^2$, preferably from $1\times10^{-4}$ to $1\times10^{-1}$ g/m$^2$, more preferably from $1\times10^{-3}$ to $1\times10^{-2}$ g/m$^2$.

Fluorine-containing surfactants may be used either singly or in combination with other conventionally known surfactants, of which the combined use is preferred.

The photosensitive material of the present invention is also suited for a scanning exposure system using a cathode ray tube (CRT) as well as printing system using a usual negative printer. A cathode ray tube exposure apparatus is simple and compact and is therefore of low cost as compared with the apparatus using laser. It facilitates adjustment of optical axis and color.

For a cathode ray tube to be used for image exposure, various emitters showing light emission to spectral regions as needed are used. For example, any one of red emitter, green emitter and blue emitter, or a mixture of two or more of them is used. The spectral region is not limited to the above red, green or blue, and a fluorescent material emitting light in yellow, orange, violet or infrared region is also usable. A cathode ray tube which emits white light by mixing these emitters is often used.

When a photosensitive material has a plurality of photosensitive layers having different spectral sensitivity distributions and a cathode ray tube also has a fluorescent material exhibiting light emission in a plurality of spectral regions, a plurality of colors may be exposed simultaneously, in other words, image signals of a plurality of colors may be inputted to the cathode ray tube to cause light emission from the tube surface. Alternatively, it is also possible to input an image signal of each color in order, cause emission of light of each color in order and expose through a film cutting colors other than the intended color (sequential exposure). In general, sequential exposure is preferred for obtaining a high quality image because it permits use of a cathode ray tube having high resolving power.

For the photosensitive material of the present invention, preferably employed is digital scanning exposure system using monochromatic high-density light such as gas laser, light emitting diode, semiconductor laser or second harmonic generating light source (SHG) where solid laser using semiconductor laser as a light exciting source is combined with non-linear optical crystals. In order to make the system compact and less expensive, it is preferred to use semiconductor laser or second harmonic generating light source (SHG) where semiconductor laser or solid laser is combined with non-linear optical crystals. In order to design an apparatus which is compact and less expensive and has long life and high stability, use of semiconductor laser is preferred. Use of semiconductor laser as at least one of exposure light sources is preferred.

When such a scanning exposure light source is used, the spectral sensitivity maximum wavelength of the photosensitive material of the present invention can be set freely according to the wavelength of the scanning exposure light source to be used. Since the oscillation wavelength of a laser can be made half by using an SHG light source available by using, in combination, nonlinear optical crystal with a solid laser using a semiconductor laser as an excitation light source, or with a semiconductor laser, blue light and green light can be obtained. Accordingly, it is possible that the photosensitive material can have a spectral sensitivity maximum in the usual three wavelength regions of blue, green and red. When the exposure time in such scanning exposure is defined as a time for exposing a pixel size when a pixel density is made 400 dpi, the preferred exposure time is $10^{-4}$ second or less, more preferably, $10^{-6}$ second or less.

Preferred scanning exposure systems which can be applied to the present invention are described specifically in the patents described in the above table.

For processing the photosensitive material of the present invention, processing materials and processing methods as described in Japanese Patent Laid-Open No. 207250/1990, page 26, lower right column, line 1 to page 34, upper right column, line 9; and Japanese Patent Laid-Open No. 97355/1992, page 5, upper left column, line 17 to page 18, lower right column, line 20 can be preferably used. Further, as preservatives for use in the developer, compounds described in the patents described in the above table can preferably be used.

The present invention can also be preferably applied to photosensitive materials having rapid processing suitability. The term "color developing time" as used herein means the time from when a photosensitive material is dipped in a color developing solution until it is transferred to a bleaching/fixing solution in the subsequent step. For example, when the photosensitive material is processed in an automatic processor, the color developing time means the total of the time during when the photosensitive material is immersed in a color developing solution (so-called, in-the-liquid time) and the time during when it is transferred in the air toward a bleaching/fixing bath of the subsequent processing step after taken out from the color developing solution. The term "bleaching/fixing time" as used herein means the time from when the photosensitive material is dipped in the bleaching/fixing solution until it is put into the subsequent washing or stabilizing bath. The term "washing or stabilizing time" is the time during when the photosensitive material is in a washing or stabilizing solution (so-called, in-the-liquid time) until it is brought to the drying step.

Upon rapid processing in the present invention, the color developing time is preferably 60 seconds or less, more preferably from 6 to 50 seconds, and still more preferably from 6 to 30 seconds. The bleaching/fixing time is preferably 60 seconds or less, more preferably from 6 to 50 seconds, and still more preferably from 6 to 30 seconds. The washing or stabilizing time is preferably 150 seconds or less, more preferably from 6 to 130 seconds.

As the developing method of the photosensitive material of the present invention after exposure, usable are a wet system such as a conventional developing method using a developing solution containing an alkali agent and a developing agent, and a developing method where a developing agent is incorporated in a photosensitive material and development is conducted by an activator such as an alkali solution free of a developing agent; and a heat developing system without using a processing solution. The method using an activator is preferred, because a processing solution free of a developing agent facilitates management and handling of the solution. In addition, the load of waste solution disposal is less so that this method is preferred also from the standpoint of the environmental protection. In an activator processing system, preferred as the developing agent or the precursor thereof incorporated in a photosensitive material are the hydrazine compounds described in Japanese Patent Laid-Open Nos. 234388/1996, 152686/1997, 152693/1997, 211814/1997 and 160193/1997.

A developing method of image amplification (intensification processing) while reducing the amount of silver coated to the photosensitive material and hydrogen peroxide is used is also preferably employed. Application of this method to the above-described activator processing system is especially preferred. Image forming methods using an activator containing hydrogen peroxide as described in Japanese Patent Laid-Open Nos. 297354/1996 and 152695/1997 are preferred. In an activator processing method, a photosensitive material is ordinarily subjected to desilvering treatment after being processed with an activator, but in the image amplifying processing using a low silver content photosensitive material, simple processing of performing washing or stabilization without desilvering process can be effected after processing with an activator. Further, in a system of reading out image data of a photosensitive material through a scanner, a processing mode which necessitates no desilvering processing can be adopted even when a high silver content photosensitive material such as a photographic photosensitive is used.

Well-known materials and processing methods can be used as the materials of the processing solutions such as activator solution, desilvering solution (bleaching/fixing solution), washing solution and stabilizing solution for use in the present invention and processing methods. For example, those disclosed in Research Disclosure, Item 36544, pp. 536 to 541 (September, 1994) and Japanese Patent Laid-Open No. 234388/1996 are preferably used.

When the photosensitive material of the present invention is subjected to an exposure by printer, the band stop filter as described in U.S. Pat. No. 4,880,726 is preferred. Use of this filter makes it possible to remove color mixing of light and to markedly improve color reproducibility.

The photosensitive material of the present invention may be subjected to pre-exposure of yellow micro dot pattern to restrict printing before image data are given as described in EP-A-0789270 and EP-A-0789480.

EXAMPLE

The present invention will hereinafter be described by Examples in further detail. It should however be borne in mind that the present invention is not limited to or by them.

Example I-1
<Emulsion I-1; Preparation of Cubic Silver Chloride Sample (1)> (Comparative Example)

To a 5% aqueous solution of lime-processed gelatin was added 5.6 g of sodium chloride, followed by the addition of 42.8 mL of 1N sulfuric acid and 1.1 mL of a 1% aqueous solution of N,N'-dimethylimidazolidine-2-thione. An aqueous solution (241.2 mL) containing 0.21 mol of silver nitrate and an aqueous solution (241.2 mL) containing 0.21 mol of sodium chloride were added and mixed at 61° C. over 24 minutes while stirring. To the reaction mixture were added an aqueous solution (720 mL) containing 1.91 mol of silver nitrate and an aqueous solution (720 mL) containing 1.91 mol of sodium chloride over 40 minutes at a temperature maintained at 61° C., whereby cubic grains having an average grain size of 0.62 μm (variation coefficient: 10%) were obtained. The grains were then precipitated and desalted by washing at 40° C. Further, 168.0 g of lime-processed gelatin was added to the emulsion to adjust its pH and pAg to 7.3 and 5.6, respectively. To the emulsion thus obtained were added a gold sensitizer (gold (I) tetrafluoroborate bis (1,4,5-trimethyl-1,2,4-triazolium-3-thiolato)) in an amount of $1.5 \times 10^{-5}$ mol per mol of silver and a sulfur sensitizer (sodium thiosulfate) in an amount of $6 \times 10^{-7}$ mol per mol of silver. Further, blue-sensitive spectral sensitizing dyes (A and B) were added in amounts of $2.3 \times 10^{-4}$ mol and $1.5 \times 10^{-4}$ mol. each per mol of silver, respectively to chemically and spectrally sensitize the emulsion optimally at 60° C. Further, 1-(5-methylureidophenyl)-5-mercaptotetrazole was added in an amount of $4.4 \times 10^{-4}$ mol per mol of silver, whereby Emulsion 1-1 was prepared.

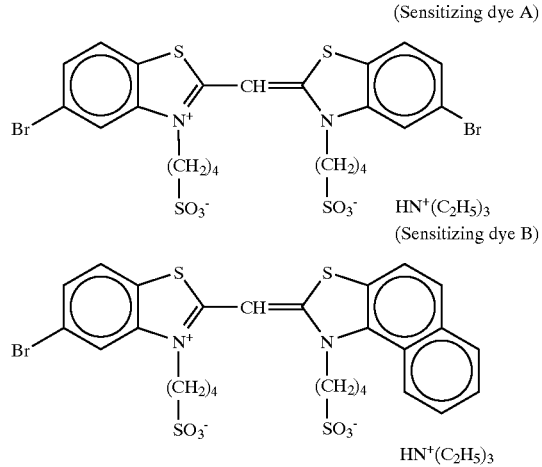

(Sensitizing dye A)

(Sensitizing dye B)

<Emulsion 1-2; Preparation of Cubic Silver Chloride Sample Doped with $[IrCl_6]^{3-}$> (Comparative Example)

In a similar manner to that employed for Emulsion 1-1 except that $[IrCl_6]^{3-}$ was added to the 90 to 95% portion, in grain volume, from the center of the grain of Emulsion 1-1 in an amount of $3 \times 10^{-8}$ mol based on the amount of silver added to the emulsion, Emulsion 1-2 was prepared.

<Emulsion 1-3; Preparation of Cubic Silver Chloride Sample Doped with $[IrCl_6]^{3-}$ and $[Ru(CN)_6]^{4-}$> (Comparative Example)

In a similar manner to that employed for Emulsion 1-1 except that $[IrCl_6]^{3-}$ was added to the 90 to 95% portion, in grain volume, from the center of the grain of Emulsion 1-1 in an amount of $3 \times 10^{-8}$ mol based on the amount of silver added to the emulsion, and $[Ru(CN)_6]^{4-}$ was added to the 80 to 97% portion, in terms of grain volume, from the center of the grain of Emulsion 1-1 in an amount of $5 \times 10^{-5}$ mol based on the amount of silver added to the emulsion, Emulsion 1-3 was prepared.

<Emulsion 1-4; Preparation of Cubic Silver Chloride Sample Doped with $[IrCl_5(thiazole)]^{2-}$> (Comparative Example)

In a similar manner to that employed for Emulsion 1-1 except that $[IrCl_5(thiazole)]^{2-}$ was added to the 90 to 95% layer of Emulsion 1-1 in an amount of $3 \times 10^{-8}$ mol based on the amount of silver added to the emulsion, Emulsion 1-4 was prepared.

<Emulsions 1-5 to 1-15: Preparation of Cubic Silver Chloride Samples Doped with $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(NH_2SO_2NH_2)]^{2-}$, $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ respectively> (Invention Products)

In a similar manner to that employed for Emulsion 1-1 except that $[IrCl_5(NH_3)]^{2-}$, $[IrCl_5(NH_2OH)]^{3-}$, $[IrCl_5(NCO)]^{3-}$, $[IrCl_5(NH_2SO_3)]^{2-}$, $[IrCl_5(NH_2SO_2NH_2)]^{2-}$, $[IrCl_5(N(CN)_2)]^{3-}$ $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ were added to the 90 to 95% portion, in terms of grain volume, from the center of the grain of Emulsion 1-1 in an amount of $3 \times 10^{-8}$ mol based on the amount of silver added to the emulsion, Emulsions 1-5 to 1-15 were prepared, respectively.

<Emulsions 1-16 to 1-26: Preparation of Cubic Silver Chloride Samples Doped with $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(N(CN)_2)]^{3-}$, $[IrCl_5(S(CN)_2)]^{2-}$, $[IrCl_5(NH_2SO_2NH_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$, respectively and $[Ru(CN)_6]^{4-}$> (Invention Products)

In a similar manner to that employed for Emulsion 1-1 except that $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(N(CN)_2)]^{3-}$, $[IrCl_5(S(CN)_2)]^{2-}$, $[IrCl_5(NH_2SO_2NH_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ were added to the 90 to 95% portion, in terms of grain volume, from the center of the grain of Emulsion 1-1 in an amount of $3\times10^{-8}$ mol based on the amount of silver added to the emulsion, and $[Ru(CN)_6]^{4-}$ was added to the 80 to 97% portion, in terms of grain volume, from the center of the grain of Emulsion 1-1 in an amount of $5\times10^{-5}$ mol based on the amount of silver added to the emulsion, Emulsions 1-16 to 1-26 were prepared, respectively.

After corona discharge treatment was given to the surface of a paper support covered on both sides with a polyethylene resin, a gelatin undercoat layer containing sodium dodecylbenzenesulfonate was formed thereon. First to seventh photographic constituent layers were then successively formed by coating on the undercoat layer to prepare silver halide color photosensitive material samples (101) to (126) having the following layer constitution. The coating solution of each photographic constituent layer was prepared as described below.

Preparation of Coating Solution for First Layer:

A yellow coupler (ExY) (57 g), 7 g of a color image stabilizer (Cpd-1), 4 g of a color image stabilizer (Cpd-2) 7 g of a color image stabilizer (Cpd-3), and 2 g of a color image stabilizer (Cpd-8) were dissolved in 21 g of a solvent (Solv-1) and 80 ml of ethyl acetate. The resulting solution was emulsified and dispersed by a high-speed stirring emulsifier (dissolver) in 220 g of a 23.5 wt % aqueous gelatin solution containing 4 g of sodium dodecylbenzenesulfonate, and water was added thereto to obtain 900 g of Emulsified dispersion A.

The resulting emulsified dispersion A and Emulsion 1-1 were mixed and dissolved to prepare a coating solution for first layer having the composition as shown below. The coating amount of the emulsion means that in terms of silver.

The coating solutions for second to seventh layers were prepared in a similar manner to that employed for the coating solution for first layer. As gelatin hardener for each layer, 1-oxy-3,5-dichloro-s-triazine sodium salt (H-1), (H-2) or (H-3) was used. In addition, an antiseptic Ab-1, Ab-2, Ab-3 and Ab-4 were added to each layer to give a total amount of 15.0 mg/m², 60.0 mg/m², 5.0 mg/m² and 10.0 mg/m², respectively.

(H-1) Hardener

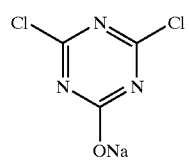

(used in an amount of 1.4% by mass based on gelatin)

(H-2) Hardener

-continued

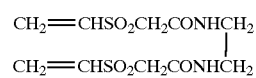

(H-3) Hardener

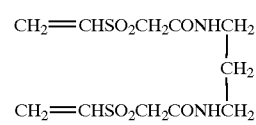

(Ab-1) Antiseptic      (Ab-2) Antiseptic

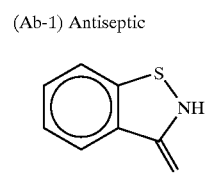 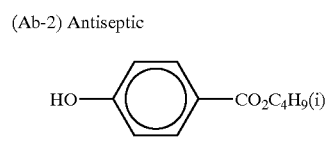

(Ab-3) Antiseptic)

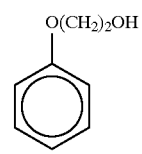

(Ab-4) Antiseptic)
A 1:1:1:1 mixture (molar ratio) of a, b, c and d

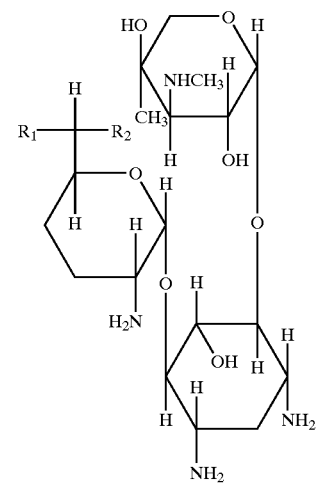

| | $R_1$ | $R_2$ |
|---|---|---|
| a | —$CH_3$ | —$NHCH_3$ |
| b | —$CH_3$ | —$NH_2$ |
| c | —H | —$NH_2$ |
| d | —H | —$NHCH_3$ |

The following spectral sensitizing dyes were respectively added to the silver chlorobromide emulsions of the green-sensitive and red-sensitive emulsion layers.

Green-sensitive Emulsion Layer:

Green-sensitive Emulsion Layer:

Sensitizing dye D

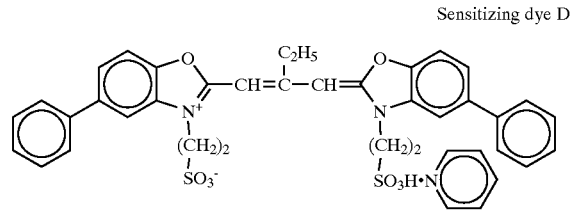

Sensitizing dye E

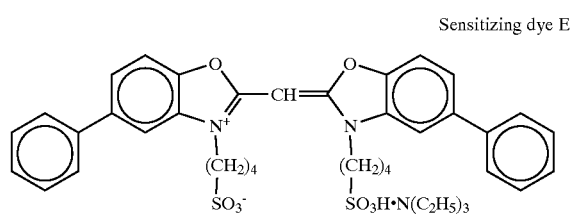

Sensitizing dye F

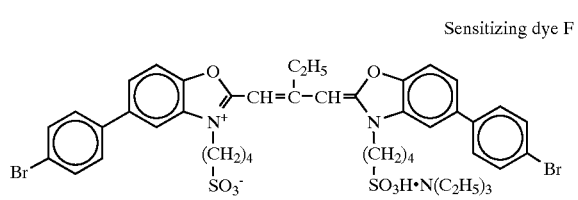

(Sensitizing dye D was added in an amount of $3.0 \times 10^{-4}$ Mol to a large grain size emulsion, and in an amount of $3.6 \times 10^{-4}$ mol to a small grain size emulsion, each per mol of silver halide. Sensitizing dye E was added in an amount of $4.0 \times 10^{-5}$ mol to a large grain size emulsion, and in an amount of $7.0 \times 10^{-5}$ mol to a small grain size emulsion, each per mol of silver halide. Sensitizing dye F was added in an amount of $2.0 \times 10^{-4}$ mol to a large grain size emulsion, and in an amount of $2.8 \times 10^{-4}$ mol to a small grain size emulsion, each per mol of silver halide)

Red-sensitive Emulsion Layer:

Sensitizing dye G

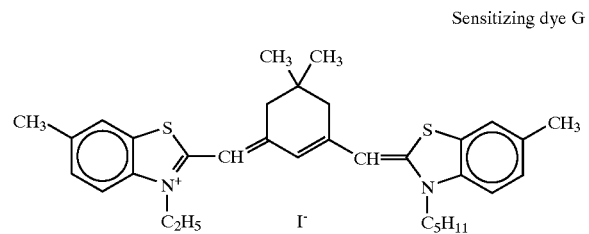

Sensitizing dye H

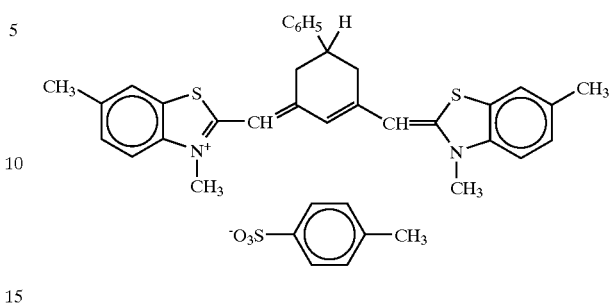

(Sensitizing dye G and Sensitizing dye H were each added in an amount of $8.0 \times 10^{-5}$ mol to a large grain size emulsion, and $10.7 \times 10^{-5}$ mol to a small grain size emulsion, each per mol of silver halide)

Further, the below-described Compound I was added to the red-sensitive emulsion layer in an amount of $3.0 \times 10^{-3}$ mol per mol of silver halide.

Compound I

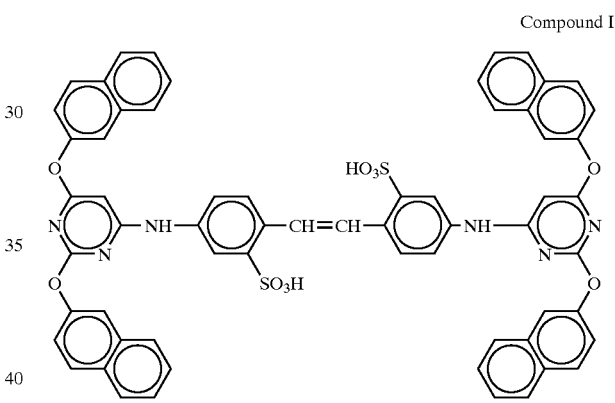

Further, 1-(3-methylureidophenyl)-5-mercaptotetrazole was added to the green-sensitive emulsion layer and the red-sensitive emulsion layer in an amount of $3.3 \times 10^{-4}$ mol, $1.0 \times 10^{-3}$ mol and $5.9 \times 10^4$ mol per mol of silver halide. It was also added to the second, fourth, sixth and seventh layers in an amount of $0.2$ mg/m$^2$, $0.2$ mg/m$^2$, $0.6$ mg/m$^2$ and $0.1$ mg/m$^2$, respectively.

To the blue-sensitive emulsion layer and the green-sensitive emulsion layer was added 4-hydroxy-6-methyl-1,3,3a,7-tetrazaindene in an amount of $1 \times 10^{-4}$ mol and $2 \times 10^{-4}$ mol, respectively, per mol of silver halide.

To the red-sensitive emulsion layer was added $0.05$ g/m$^2$ of a copolymer latex of methacrylic acid and butyl acrylate (weight ratio: 1:1, average molecular weight: 200,000 to 400,000).

To the second, fourth and sixth layers was added disodium catechol-3,5-disulfonate in an amount of 6 mg/m$^2$, 6 mg/m$^2$ and 18 mg/m$^2$, respectively.

The below-described dyes were added in order to prevent irradiation (the numerals in parentheses represent the coating amount).

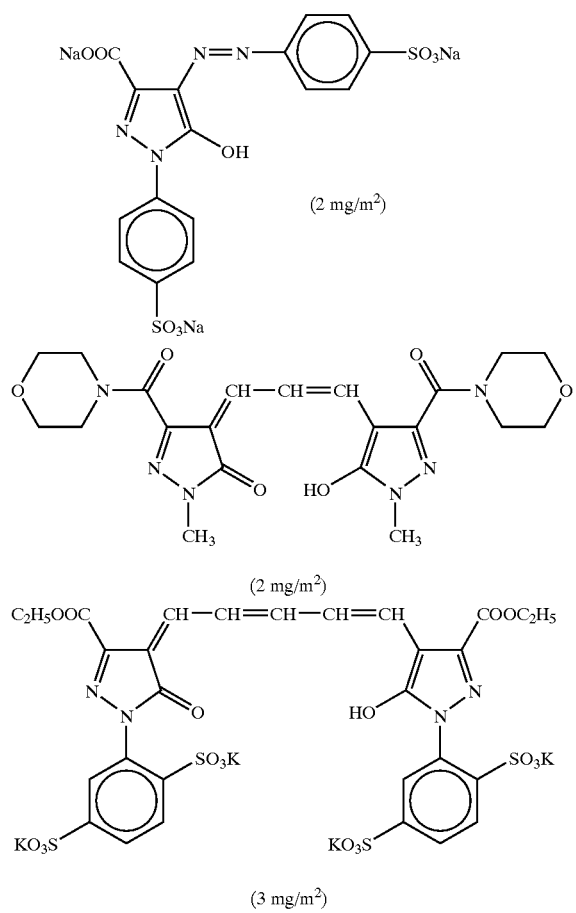

(2 mg/m²)

(2 mg/m²)

(3 mg/m²)

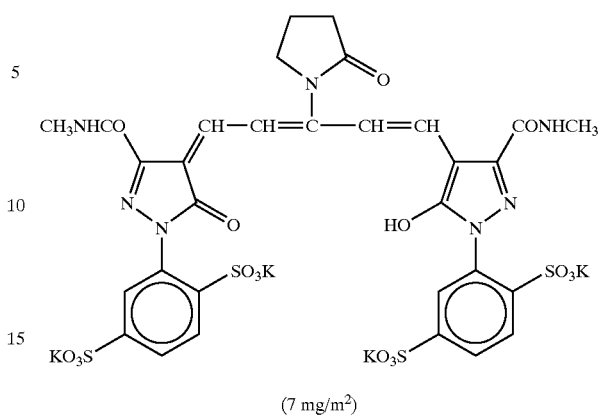

(7 mg/m²)

The constitution of each layer is shown below. The numeral represents the coating amount (g/m²). The numeral for silver halide emulsion means the coating amount in terms of silver.

Support

Paper laminated with polyethylene resin [a polyethylene resin on the first layer side contains a white pigment (TiO$_2$ content: 16% by mass, ZnO content: 4% by mass), fluorescent brightener (4,4'-bis(5-methylbenzoxazolyl)stilbene content: 0.03 wt %), and a bluish dye (ultramarine)).

| First layer (blue-sensitive emulsion layer) | |
|---|---|
| Emulsion 1-1 | 0.24 |
| Gelatin | 1.25 |
| Yellow Coupler (ExY) | 0.57 |
| Color image stabilizer (Cpd-1) | 0.07 |
| Color image stabilizer (Cpd-2) | 0.04 |
| Color image stabilizer (Cpd-3) | 0.07 |
| Color image stabilizer (Cpd-8) | 0.02 |
| Solvent (Solv-1) | 0.21 |
| Second layer (color mixing preventive layer) | |
| Gelatin | 0.99 |
| Color mixing preventive (Cpd-4) | 0.09 |
| Color image stabilizer (Cpd-5) | 0.018 |
| Color image stabilizer (Cpd-6) | 0.13 |
| Color image stabilizer (Cpd-6) | 0.13 |
| Color image stabilizer (Cpd-7) | 0.01 |
| Solvent (Solv-1) | 0.06 |
| Solvent (Solv-2) | 0.22 |
| Third layer (green-sensitive emulsion layer) | |
| Silver bromide chloride emulsion Em-1 (a cubic emulsion sensitized with gold sulfur, a 1:3 mixture (silver molar ratio) of a large grain size emulsion having an average grain size of 0.45 μm and a small grain size emulsion having an average grain size of 0.35 μm. Variation coefficients of the grain size distribution were 0.10 and 0.08, respectively. Emulsions of both size each contained 0.15 mol % of silver iodide in the vicinity of the grain surface, and 0.4 mol % of silver bromide localized on the grain surface) | 10.14 |

|  | -continued |  |
| --- | --- | --- |
|  | Gelatin | 1.36 |
|  | Magenta coupler (ExM) | 0.15 |
|  | Ultraviolet absorber (UV-A) | 0.14 |
|  | Color image stabilizer (Cpd-2) | 0.02 |
|  | Color image stabilizer (Cpd-4) | 0.002 |
|  | Color image stabilizer (Cpd-6) | 0.09 |
|  | Color image stabilizer (Cpd-8) | 0.02 |
|  | Color image stabilizer (Cpd-9) | 0.03 |
|  | Color image stabilizer (Cpd-10) | 0.01 |
|  | Color image stabilizer (Cpd-11) | 0.0001 |
|  | Solvent (Solv-3) | 0.11 |
|  | Solvent (Solv-4) | 0.22 |
|  | Solvent (Solv-5) | 0.20 |
| Fourth layer (color mixing preventive layer) | | |
|  | Gelatin | 0.71 |
|  | Color mixing preventive (Cpd-4) | 0.06 |
|  | Color image stabilizer (Cpd-5) | 0.013 |
|  | Color image stabilizer (Cpd-6) | 0.10 |
|  | Color image stabilizer (Cpd-7) | 0.007 |
|  | Solvent (Solv-1) | 0.04 |
|  | Solvent (Solv-2) | 0.16 |
| Fifth layer (red-sensitive emulsion layer) | | |
|  | Silver bromide chloride emulsion Em-2 (a cubic emulsion sensitized with gold sulfur; a 5:5 mixture (silver molar ratio) of a large grain size emulsion having an average grain size of 0.40 μm and a small grain size emulsion having an average grain size of 0.30 μm; variation coefficients of the grain size distribution were 0.09 and 0.11 respectively; each emulsion contained 0.1 mol % of silver iodide in the vicinity of the grain surface, and 0.8 mol % of silver bromide localized on the grain surface) | 0.12 |
|  | Gelatin | 1.11 |
|  | Cyan coupler (ExC-2) | 0.13 |
|  | Cyan coupler (ExC-3) | 0.03 |
|  | Color image stabilizer (Cpd-1) | 0.05 |
|  | Color image stabilizer (Cpd-6) | 0.06 |
|  | Color image stabilizer (Cpd-7) | 0.02 |
|  | Color image stabilizer (Cpd-9) | 0.04 |
|  | Color image stabilizer (Cpd-10) | 0.01 |
|  | Color image stabilizer (Cpd-14) | 0.01 |
|  | Color image stabilizer (Cpd-15) | 0.12 |
|  | Color image stabilizer (Cpd-16) | 0.03 |
|  | Color image stabilizer (Cpd-17) | 0.09 |
|  | Color image stabilizer (Cpd-18) | 0.07 |
|  | Solvent (Solv-5) | 0.15 |
|  | Solvent (Solv-8) | 0.05 |
| Sixth layer (ultraviolet absorbing layer) | | |
|  | Gelatin | 0.46 |
|  | Ultraviolet Absorber (UV-B) | 0.45 |
|  | Compound (S1-4) | 0.0015 |
|  | Solvent (Solv-7) | 0.25 |
| Seventh Layer (protective layer) | | |
|  | Gelatin | 1.00 |
|  | Acrylic modified copolymer of polyvinyl alcohol (modification degree: 17%) | 0.04 |
|  | Liquid paraffin | 0.02 |
|  | Surfactant (Cpd-13) | 0.01 |

(ExY) Yellow coupler
A 70:30 mixture (molar ratio) of

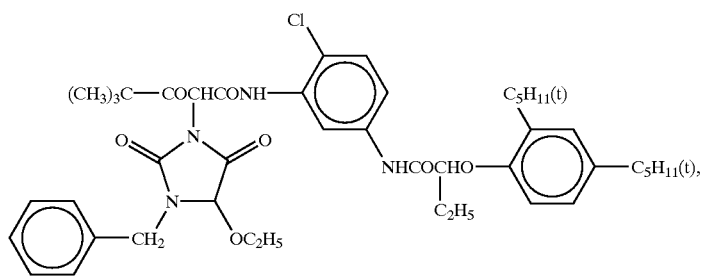

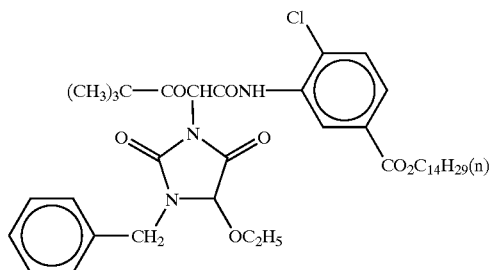
(ExM) Magenta coupler
A 40:40:20 mixture (molar ratio) of
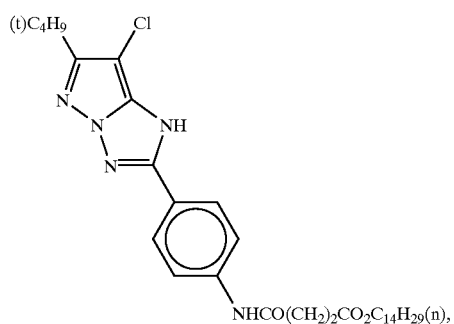
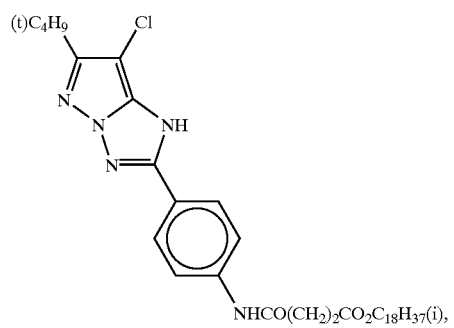
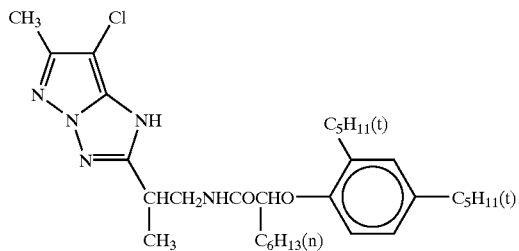

-continued
(ExC-2) Cyan coupler
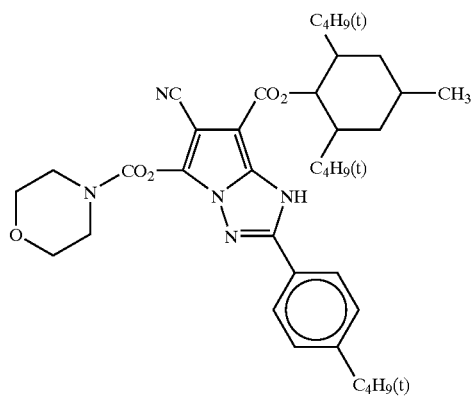
(ExC-3) Cyan coupler
A 50:25:25 mixture (molar ratio) of
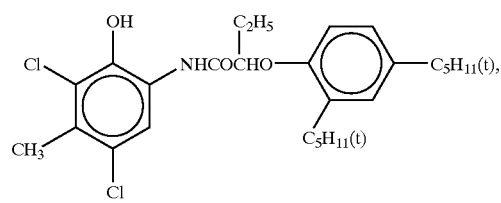
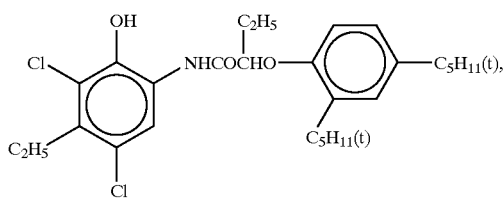
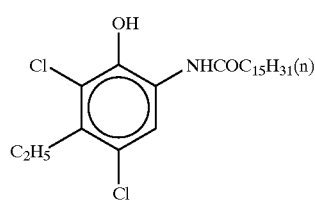
(Cpd-1) Color image stabilizer
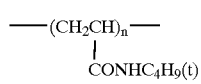
number average molecular weight: 60,000
(Cpd-2) Color image stabilizer
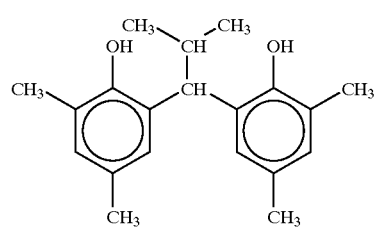

-continued
(Cpd-3) Color image stabilizer
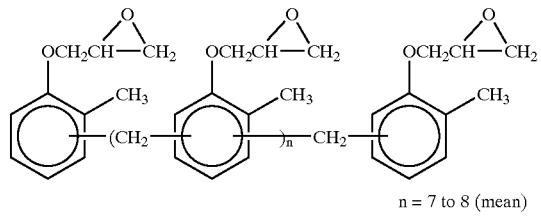
n = 7 to 8 (mean)
(Cpd-4) Color mixing preventive
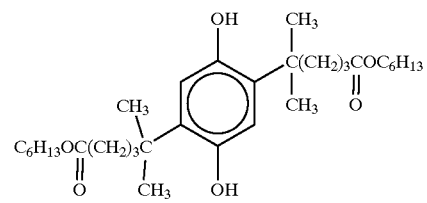
(Cpd-5) Color image stabilizer
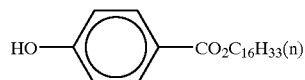
(Cpd-6) Color image stabilizer
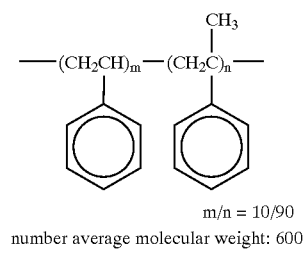
m/n = 10/90
number average molecular weight: 600
(Cpd-7) Color image stabilizer
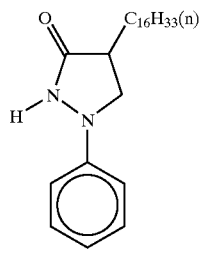
(Cpd-8) Color image stabilizer
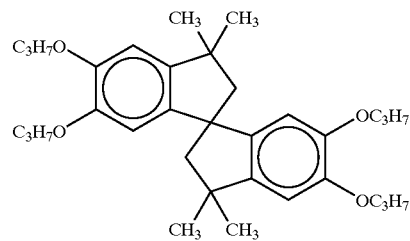

-continued
(Cpd-9) Color image stabilizer
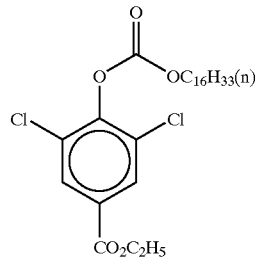
(Cpd-10) Color image stabilizer
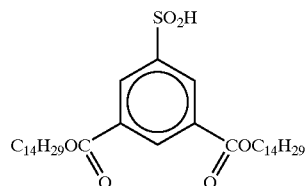
(Cpd-11)
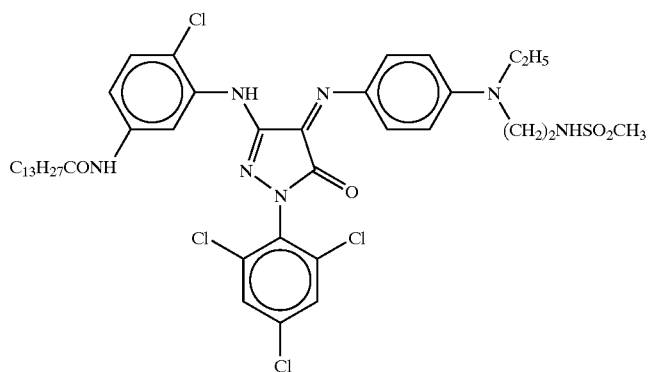
(Cpd-13) Surfactant
A 7:3 mixture (molar ratio) of
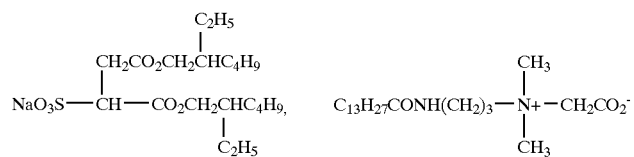
(Cpd-14)
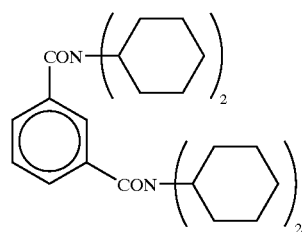
(Cpd-15)
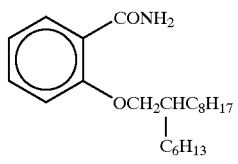

-continued
(Cpd-16) 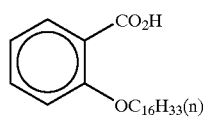
(Cpd-17) 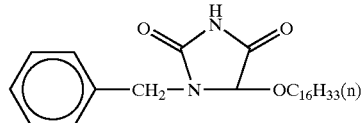
(Cpd-18)
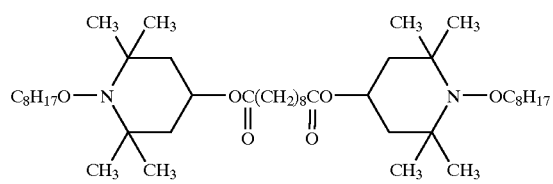
(Cpd-19) Color mixing preventative
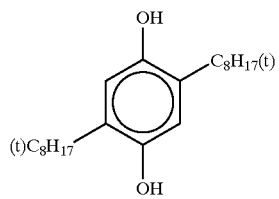
(UV-1) Ultraviolet absorber 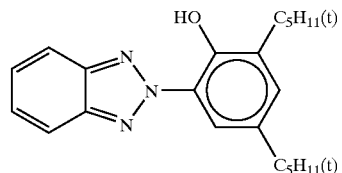
(UV-2) Ultraviolet absorber 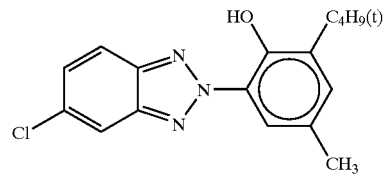
(UV-3) Ultraviolet absorber 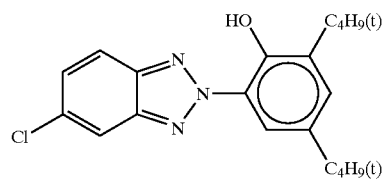
(UV-4) Ultraviolet absorber 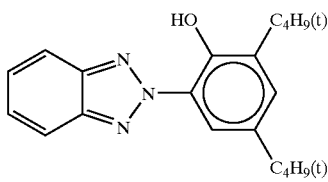
(UV-5) Ultraviolet absorber 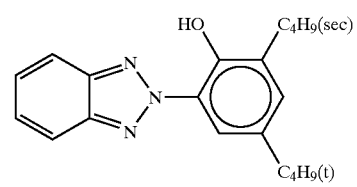
(UV-6) Ultraviolet absorber 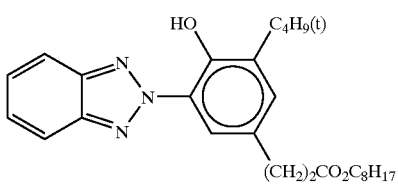

(UV-7) Ultraviolet absorber

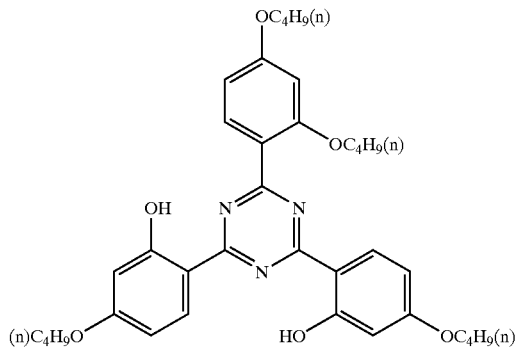

UV-A: a 4:2:2:3 mixture (weight ratio) of UV-1, UV-2, UV-3 and UV-4
UV-B: a 9:3:3:4:5:3 mixture (weight ratio) of UV-1, UV-2, UV-3, UV-4, UV-5 and UV-6
UV-C: a 1:1:1:2 mixture (weight ratio) of UV-2, UV-3, UV-6 and UV-7

(Solv-1)

(Solv-2)

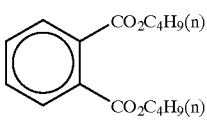

(Solv-3)

(Solv-4)

$O{=}P(OC_6H_{13}(n))_3$ (Solv-5)

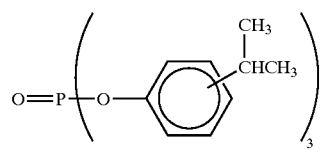

(Solv-7)

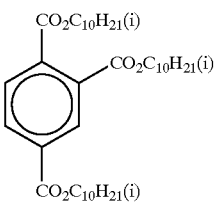

(Solv-8)

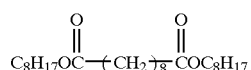

(S1-4)

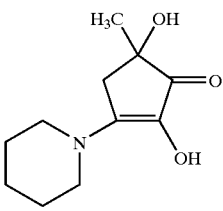

Samples (102) to (126) were prepared in a similar manner to that employed for Sample (101) except that Emulsions 1-2 to 1-26 were used instead of Emulsion 1-1, respectively.

Tests as described below were performed in order to study photographic characteristics of these samples.

Test 1: Sensitometry

Each sample was subjected to gradation exposure for sensitometry using a sensitometer ("Model FWH" product of Fuji Photo Film Co., Ltd.). An SP-1 filter was attached to the sensitometer and exposure to low illuminance was conducted for 10 seconds.

Each sample was subjected to gradation exposure for sensitometry by using a sensitometer for high intensity exposure ("Model HIE" product of Yamashita Denso Corporation). An SP-1 filter was attached to the sensitometer and exposure to high illuminance was conducted for $10^{-4}$ seconds.

After exposure, each sample was subjected to the following chromogenic development processing A.

The processing step was as follows.

[Processing A]

The above-described photosensitive material 101 was processed into a roll of 127 mm wide. After imagewise exposure by using a mini-labo printer processor "PP1258AR" (product of Fuji Photo Film Co., Ltd.), continuous processing (running test) was conducted by the below-described processing step until the color developing replenisher became two times the amount of the color developing tank capacity. The processing using this running solution was designated as processing A.

| Processing step | Temp. | Time | Replenished amount* |
|---|---|---|---|
| Color development | 38.5° C. | 45 sec | 45 mL |
| Bleaching and fixing | 38.0° C. | 45 sec | 35 mL |
| Rinse (1) | 38.0° C. | 20 sec | — |
| Rinse (2) | 38.0° C. | 20 sec | — |
| Rinse (3)** | 38.0° C. | 20 sec | — |
| Rinse (4)** | 38.0° C. | 30 sec | 121 mL |

*Replenished amount per m² of the photosensitive material
**Rinse cleaning system "RC50D" (reverse osmosis membrane module, a product of Fuji Photo Film Co., Ltd.) was installed to Rinse (3). The rinsing solution in Rinse (3) was taken out, and supplied to RC50D by a pump. The solution thus permeated through the membrane in the tank was supplied to Rinse (4) and the concentrated solution was returned back to Rinse (3).

The pressure of the pump was adjusted to keep the feeding rate of the solution to the reverse osmosis membrane module at from 50 to 300 ml/min, and the system was circulated for 10 hours a day at a controlled temperature.

(Rinsing was Conducted in a Tank Countercurrent System from (1) to (4)).

Each processing solution has the following composition:

|  | [Tank solution] | [Replenisher solution] |
|---|---|---|
| [Color developer solution] | | |
| Water | 800 mL | 800 mL |
| Dimethylpolysiloxane surfactant ("Silicone KF351A", product of Shin-etsu Chemical) | 0.1 g | 0.1 g |
| Tri(isopropanol)amine | 8.8 g | 8.8 g |
| Ethylenediaminetetraacetic acid | 4.0 g | 4.0 g |
| Polyethylene glycol (molecular weight: 300) | 10.0 g | 10.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene fluorescent brightner ("Hakkol FWA-SF", product of Showa Chemical) | 2.5 g | 5.0 g |
| Sodium sulfite | 0.1 g | 0.1 g |
| Disodium-N,N-bis(sulfonatoethyl) hydroxylamine | 8.5 g | 11.1 g |
| N-ethyl-N-(b-methanesulfonamidoethyl)-3-methyl-4-amikno-4-amiknoaniline.3/2 sulfuric monohydrate | 5.0 g | 15.7 g |
| Potassium carbonate | 26.3 g | 26.3 g |
| Water (added to make) | 1000 mL | 1000 mL |
| PH (at 25° C./adjusted with potassium hydroxide or sulfuric acid) | 10.15 | 12.50 |
| [Bleaching and fixing solution] | | |
| Water | 700 mL | 600 mL |
| Ammonium ethylenediaminetetraacetoferrate (III) | 47.0 g | 94.0 g |
| Ethylenediaminetetraacetic acid | 1.4 g | 2.8 g |
| m-Carboxybenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/L) | 107.0 mL | 214.0 mL |
| Ammonium sulfite | 16.0 g | 32.0 g |
| Ammonium bisulfite | 23.1 g | 46.2 g |
| Water (added to make) | 1000 mL | 1000 mL |
| PH (at 25° C./adjusted with acetic acid or ammonia) | 6.0 | 6.0 |
| [Rinsing solution] | | |
| Sodium chlorinated isocyanurate | 0.02 g | 0.02 g |
| Deionized water (conductivity: 5 µs/cm or less) | 1000 mL | 1000 mL |
| PH | 6.5 | 6.5 |

The yellow color-forming density for the thus development-processed Samples (101) to (126) were measured. Fog was determined from the minimum color density of the sample. The sensitivity was prescribed as a reciprocal of the exposure amount necessary for obtaining the density of fog+1.0, and the relative sensitivities for each the obtained samples to the sensitivity of development-processed Samples (101) taken as 100 are shown in Table 3, below.

TABLE 3

| Sample No. | Emulsion No. | Dopant | Relative sensitivity *1 | | Maximum density |
|---|---|---|---|---|---|
| | | | Exposure for 10 sec | Exposure for $10^{-4}$ sec | Exposure for $10^{-4}$ sec |
| 101 (Comp. Ex.) | 1-1 | — | 100 | 100 | 2.11 |
| 102 (Comp. Ex.) | 1-2 | $[IrCl_6]^{3-}$ | 93 | 205 | 2.35 |
| 103 (Comp. Ex.) | 1-3 | $[IrCl_6]^{3-} + [Ru(CN)_6]^{4-}$ | 98 | 211 | 2.35 |
| 104 (Comp. Ex.) | 1-4 | $[IrCl_5(thiazole)]^{2-}$ | 95 | 215 | 2.52 |
| 105 (Invention) | 1-5 | $[IrCl_5(NH_3)]^{2-}$ | 102 | 223 | 2.61 |
| 106 (Invention) | 1-6 | $[IrCl_5(NH_2OH)]^{2-}$ | 98 | 219 | 2.59 |

TABLE 3-continued

| Sample No. | Emulsion No. | Dopant | Relative sensitivity *1 Exposure for 10 sec | Exposure for $10^{-4}$ sec | Maximum density Exposure for $10^{-4}$ sec |
|---|---|---|---|---|---|
| 107 (Invention) | 1-7 | $[IrCl_5(NCO)]^{3-}$ | 102 | 222 | 2.62 |
| 108 (Invention) | 1-8 | $[IrCl_5(NH_2SO_3)]^{2-}$ | 99 | 217 | 2.55 |
| 109 (Invention) | 1-9 | $[IrCl_5(NH_2SO_2NH_2)]^{2-}$ | 100 | 220 | 2.58 |
| 110 (Invention) | 1-10 | $[IrCl_5(N(CN)_2)]^{3-}$ | 103 | 225 | 2.63 |
| 111 (Invention) | 1-11 | $[IrCl_5(S(CN)_2)]^{2-}$ | 101 | 221 | 2.58 |
| 112 (Invention) | 1-12 | $[IrCl_5(NH_2C(=S)NH_2)]^{2-}$ | 99 | 218 | 2.60 |
| 113 (Invention) | 1-13 | $[IrCl_5(NH_2C(SCH_3)NH)]^{2-}$ | 102 | 222 | 2.61 |
| 114 (Invention) | 1-14 | $[IrCl_5(1,3,4\text{-thiadiazole})]^{2-}$ | 101 | 223 | 2.59 |
| 115 (Invention) | 1-15 | $[IrCl_5(1,2,4\text{-thiadiazole})]^{2-}$ | 100 | 219 | 2.61 |
| 116 (Invention) | 1-16 | $[IrCl_5(NH_3)]^{2-} + [Ru(CN)_6]^{4-}$ | 110 | 230 | 2.63 |
| 117 (Invention) | 1-17 | $[IrCl_5(NH_2OH)]^{2-} + [Ru(CN)_6]^{4-}$ | 107 | 226 | 2.61 |
| 118 (Invention) | 1-18 | $[IrCl_5(NCO)]^{3-} + [Ru(CN)_6]^{4-}$ | 111 | 229 | 2.64 |
| 119 (Invention) | 1-19 | $[IrCl_5(NH_2SO_3)]^{3-} + [Ru(CN)_6]^{4-}$ | 106 | 225 | 2.58 |
| 120 (Invention) | 1-20 | $[IrCl_5(N(CN)_2)]^{3-} + [Ru(CN)_6]^{4-}$ | 112 | 231 | 2.65 |
| 121 (Invention) | 1-21 | $[IrCl_5(S(CN)_2)]^{2-} + [Ru(CN)_6]^{4-}$ | 109 | 227 | 2.59 |
| 122 (Invention) | 1-22 | $[IrCl_5(NH_2SO_2NH_2)]^{2-} + [Ru(CN)_6]^{4-}$ | 108 | 227 | 2.60 |
| 123 (Invention) | 1-23 | $[IrCl_5(NH_2C(=S)NH_2)]^{2-} + [Ru(CN)_6]^{4-}$ | 107 | 227 | 2.62 |
| 124 (Invention) | 1-24 | $[IrCl_5(NH_2C(SCH_3)NH)]^{2-} + [Ru(CN)_6]^{4-}$ | 109 | 229 | 2.62 |
| 125 (Invention) | 1-25 | $[IrCl_5(1,3,4\text{-thiadiazole})]^{2-} + [Ru(CN)_6]^{4-}$ | 110 | 230 | 2.61 |
| 126 (Invention) | 1-26 | $[IrCl_5(1,2,4\text{-thiadiazole})]^{2-} + [Ru(CN)_6]^{4-}$ | 109 | 228 | 2.63 |

*expressed as relative humidity under the respective conditions when the sensitivity of Sample 1-1 was taken as 100.

From Table 3, it has been found that the emulsion using the dopant of the present invention is less in desensitization upon exposure for 10 seconds, improved in high intensity reciprocity law failure, and higher in the maximum density than the emulsion using a known dopant.

Example I-2
<Emulsion 2-1: Preparation of Cubic Silver Chloride Sample (2)> (Comparative Example)

Grain formation was conducted in a similar manner to that employed for Emulsion 1-1 in Example 1 except that N,N'-dimethylimidazolidine-2-thione (1% aqueous solution) was omitted and the reaction temperature was adjusted to 55° C., whereby a cubic silver chloride emulsion having an average grain size of 0.38 μm (variation coefficient: 8%) was obtained. The resulting emulsion was optimally subjected to chemical sensitization and spectral sensitization at 60° C. by adding a gold sensitizer (gold (I) tetrafluoroborate bis(1,4,5-trimethyl-1,2,4-triazolium-3-thiolato)) in an amount of $2.4 \times 10^{-5}$ mol/mol-Ag, a sulfur sensitizer (sodium thiosulfate) in an amount of $1 \times 10^{-7}$ mol/mol-Ag, and green-sensitive spectral sensitizing dyes (D, E and F) in amounts of $3.6 \times 10^{-4}$ mol/mol-Ag, $7 \times 10^{-5}$ mol/mol-Ag and $2.8 \times 10^{-4}$ mol/mol-Ag, respectively. Further, 1-(5-methylureidophenyl)-5-mercaptotetrazole was added to the emulsion in an amount of $4.4 \times 10^{-4}$ mol/mol-Ag, whereby Emulsion 2-1 was obtained.

<Emulsion 2-2; Preparation of Cubic Silver Chloride Sample Doped with $[IrCl_6]^{3-}$> (Comparative Example)

In a similar manner to that employed for Emulsion 2-1 except that $[IrCl_6]^{3-}$ was added to the 90 to 95% portion, in terms of grain volume, from the center of the grain of Emulsion 2-1 in an amount of $1 \times 10^{-7}$ mol based on the amount of silver added to the emulsion, Emulsion 2-2 was prepared.

<Emulsion 2-3; Preparation of Cubic Silver Chloride Sample Doped with $[IrCl_6]^{3-}$ and $[Os(NO)Cl_5]^{2-}$> (Comparative Example)

In a similar manner to that employed for Emulsion 2-1 except that $[IrCl_6]^{3-}$ was added to the 90 to 95% portion, in terms of grain volume, from the center of the grain of Emulsion 2-1 in an amount of $3 \times 10^{-8}$ mol based on the amount of silver added to the emulsion, and $[Os(NO)Cl_5]^{2-}$ was added to the 10 to 50% portion, in terms of grain volume, from the center of the grain of Emulsion 2-1 in an amount of $1 \times 10^{-9}$ mol based on the amount of silver added to the emulsion, Emulsion 2-3 was prepared.

<Emulsion 2-4; Preparation of Cubic Silver Chloride Sample Doped with $[IrCl_5(\text{thiazole})]^{2-}$> (Comparative Example)

In a similar manner to that employed for Emulsion 2-1 except that $[IrCl_5(\text{thiazole})]^{2-}$ was added to the 90 to 95% portion, in terms of grain volume, from the center of the grain of Emulsion 2-1 in an amount of $1 \times 10^{-7}$ mol based on the amount of silver added to the emulsion, Emulsion 2-4 was prepared.

<Emulsions 2-5 to 2-15: Preparation of Cubic Silver Chloride Samples Doped with $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(NH_2SO_2NH_2)]^{2-}$, $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$, respectively> (Invention Products)

In a similar manner to that employed for Emulsion 2-1 except that $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(NH_2SO_2NH_2)]^{2-}$, $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ were added to the 90 to 95% portion, in terms of grain volume, from the center of the grain of Emulsion 2-1 in an amount of $1×10^{-7}$ mol based on the amount of silver added to the emulsion, Emulsions 2-5 to 2-15 were prepared, respectively.

<Emulsions 2-16 to 2-26: Preparation of Cubic Silver Chloride Samples Doped with $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(NH_2SO_2NH_2)]^{2-}$, $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ and also $[Os(NO)Cl_5]^{2-}$> (Invention Products)

In a similar manner to that employed for Emulsion 2-1 except that $[IrCl_5(NH_3)]^{2-}$, $[IrCl_5(NH_2OH)]^{2-}$, $[IrCl_5(NCO)]^{3-}$, $[IrCl_5(NH_2SO_3)]^{3-}$, $[IrCl_5(NH_2SO_2NH_2)]^{2-}$, $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ were added to the 90 to 95% portion, in terms of grain volume, from the center of the grain of Emulsion 2-1 in an amount of $3×10^{-8}$ mol based on the amount of silver added to the emulsion, and $[Os(NO)Cl_5]^{2-}$ was added to the 10 to 50% portion, in terms of grain volume, from the center of the grain of Emulsion 2-1 in an amount of $1×10^{-9}$ mol based on the amount of silver added to the emulsion, Emulsions 2-16 to 2-26 were prepared, respectively.

Samples (201) to (226) having a similar layer constitution to that employed in Example I-1 except that the emulsion of the first layer was replaced with Emulsions 2-1 to 2-26 were prepared, respectively. Test 1 in Example 1 and the below-described Test 2 were conducted for these samples.

Test 2: Latent Image Stability After Exposure

Each of the samples was measured for sensitometry while changing the time from exposure for 1/10 second to processing A. Sensitivities when processing was conducted 7 seconds after exposure and 30 minutes after exposure were determined.

The results of these tests are shown in Table 4.

TABLE 4

| Sample No. | Emulsion No. | Dopant | Relative sensitivity *1 | | Difference in sensitivity caused by change in time from exposure to processing *2 |
|---|---|---|---|---|---|
| | | | Exposure for 10 sec | Exposure for $10^{-4}$ sec | |
| 201 (Comp. Ex.) | 2-1 | — | 100 | 100 | 1 |
| 202 (Comp. Ex.) | 2-2 | $[IrCl_6]^{3-}$ | 82 | 161 | 55 |
| 203 (Comp. Ex.) | 2-3 | $[IrCl_6]^{3-} + [Os(NO)Cl_5]^{2-}$ | 80 | 163 | 51 |
| 204 (Comp. Ex.) | 2-4 | $[IrCl_5(\text{thiazole})]^{2-}$ | 95 | 220 | 6 |
| 205 (Invention) | 2-5 | $[IrCl_5(NH_3)]^{2-}$ | 102 | 229 | 2 |
| 206 (Invention) | 2-6 | $[IrCl_5(NH_2OH)]^{2-}$ | 98 | 226 | 3 |
| 207 (Invention) | 2-7 | $[IrCl_5(NCO)]^{3-}$ | 102 | 230 | 1 |
| 208 (Invention) | 2-8 | $[IrCl_5(NH_2SO_3)]^{3-}$ | 99 | 223 | 3 |
| 209 (Invention) | 2-9 | $[IrCl_5(NH_2SO_2NH_2)]^{2-}$ | 100 | 227 | 3 |
| 210 (Invention) | 2-10 | $[IrCl_5(N(CN)_2)]^{3-}$ | 102 | 230 | 1 |
| 211 (Invention) | 2-11 | $[IrCl_5(S(CN)_2)]^{2-}$ | 101 | 232 | 1 |
| 212 (Invention) | 2-12 | $[IrCl_5(NH_2C(=S)NH_2)]^{2-}$ | 99 | 229 | 2 |
| 213 (Invention) | 2-13 | $[IrCl_5(NH_2C(SCH_3)NH)]^{2-}$ | 102 | 230 | 2 |
| 214 (Invention) | 2-14 | $[IrCl_5(1,3,4\text{-thiadiazole})]^{2-}$ | 101 | 229 | 3 |
| 215 (Invention) | 2-15 | $[IrCl_5(1,2,4\text{-thiadiazole})]^{2-}$ | 100 | 230 | 3 |
| 216 (Invention) | 2-16 | $[IrCl_5(NH_3)]^{2-} + [Os(NO)Cl_5]^{2-}$ | 100 | 234 | 1 |
| 217 (Invention) | 2-17 | $[IrCl_5(NH_2OH)]^{2-} + [Os(NO)Cl_5]^{2-}$ | 97 | 231 | 2 |
| 218 (Invention) | 2-18 | $[IrCl_5(NCO)]^{3-} + [Os(NO)Cl_5]^{2-}$ | 101 | 236 | 1 |
| 219 (Invention) | 2-19 | $[IrCl_5(NH_2SO_3)]^{3-} + [Os(NO)Cl_5]^{2-}$ | 96 | 227 | 2 |
| 220 (Invention) | 2-20 | $[IrCl_5(NH_2SO_2NH_2)]^{2-} + [Os(NO)Cl_5]^{2-}$ | 98 | 233 | 2 |
| 221 (Invention) | 2-21 | $[IrCl_5(N(CN)_2)]^{3-} + [Os(NO)Cl_5]^{2-}$ | 101 | 237 | 1 |
| 222 (Invention) | 2-22 | $[IrCl_5(S(CN)_2)]^{2-} + [Os(NO)Cl_5]^{2-}$ | 100 | 234 | 1 |
| 223 (Invention) | 2-23 | $[IrCl_5(NH_2C(=S)NH_2)]^{2-} + [Os(NO)Cl_5]^{2-}$ | 97 | 234 | 1 |
| 224 (Invention) | 2-24 | $[IrCl_5(NH_2C(SCH_3)NH)]^{2-} + [Os(NO)Cl_5]^{2-}$ | 101 | 236 | 1 |
| 225 (Invention) | 2-25 | $[IrCl_5(1,3,4\text{-thiadiazole})]^{2-} + [Os(NO)Cl_5]^{2-}$ | 99 | 235 | 1 |
| 226 (Invention) | 2-26 | $[IrCl_5(1,2,4\text{-thiadiazole})]^{2-} + [Os(NO)Cl_5]^{2-}$ | 100 | 236 | 2 |

*expressed as humidity under the respective conditions based on the sensitivity of Sample 2-1 taken as 100.
*2 expressed by a difference in relative sensitivity caused by a change in time from exposure to processing.

It has been found that the emulsions of the present invention were free from high intensity reciprocity failure between exposure for 10 seconds to exposure for $10^{-4}$ second and at the same time, sensitivity available from each of them is stable even if the time from exposure to processing varies (excellent in latent-image stability).

Example I-3

Thin-layer samples (301) to (326) were prepared by changing, as described below, the layer constitution of the samples obtained in Example I-2. These samples were tested for Test 1 of Example I-1 and Test 2 of Example I-2. Even after super-speedy processing, these thin layer samples exhibited good effects of the present invention similar to the samples of Example I-2. As one example of the layer constitution, that of Sample (301) will be shown below. Samples (302) to (326) are prepared using, instead of Emulsion 2-1, Emulsions 2-2 to 2-26, respectively.

Preparation of Sample 301:

| First layer (blue-sensitive emulsion layer) | |
|---|---|
| Emulsion 1-1 | 0.24 |
| Gelatin | 1.25 |
| Yellow coupler (ExY) | 0.57 |
| Color image stabilizer (Cpd-1) | 0.07 |
| Color image stabilizer (Cpd-2) | 0.04 |
| Color image stabilizer (Cpd-3) | 0.07 |
| Color image stabilizer (Cpd-8) | 0.02 |
| Solvent (Solv-1) | 0.21 |
| Second layer (color mixing preventive layer) | |
| Gelatin | 0.60 |
| Color mixing preventive (Cpd-19) | 0.09 |
| Color image stabilizer (Cpd-5) | 0.007 |
| Color image stabilizer (Cpd-7) | 0.007 |
| Ultraviolet absorber (UV-C) | 0.05 |
| Solvent (Solv-5) | 0.11 |
| Third layer (green-sensitive emulsion layer) | |
| Emulsion 2-1 | 0.14 |
| Gelatin | 0.73 |
| Magenta coupler (ExM) | 0.15 |
| Ultraviolet absorber (UV-A) | 0.05 |
| Color image stabilizer (Cpd-2) | 0.02 |
| Color image stabilizer (Cpd-7) | 0.008 |
| Color image stabilizer (Cpd-8) | 0.07 |
| Color image stabilizer (Cpd-9) | 0.03 |
| Color image stabilizer (Cpd-10) | 0.009 |
| Color image stabilizer (Cpd-11) | 0.0001 |
| Solvent (Solv-3) | 0.06 |
| Solvent (Solv-4) | 0.11 |
| Solvent (Solv-5) | 0.06 |
| Fourth layer (color mixing preventive layer) | |
| Gelatin | 0.48 |
| Color mixing preventive (Cpd-4) | 0.07 |
| Color image stabilizer (Cpd-5) | 0.006 |
| Color image stabilizer (Cpd-7) | 0.006 |
| Ultraviolet absorber (UV-C) | 0.04 |
| Solvent (Solv-5) | 0.09 |
| Fifth layer (red-sensitive emulsion layer) | |
| Emulsion 2-1 | 0.12 |
| Gelatin | 0.59 |
| Cyan coupler (ExC-2) | 0.13 |
| Cyan coupler (ExC-3) | 0.03 |
| Color image stabilizer (Cpd-7) | 0.01 |
| Color image stabilizer (Cpd-9) | 0.04 |
| Color image stabilizer (Cpd-15) | 0.19 |
| Color image stabilizer (Cpd-18) | 0.04 |
| Ultraviolet absorber (UV-7) | 0.02 |
| Solvent (Solv-5) | 0.09 |

| -continued | |
|---|---|
| Sixth layer (ultraviolet absorbing layer) | |
| Gelatin | 0.32 |
| Ultraviolet absorber (UV-C) | 0.42 |
| Solvent (Solv-7) | 0.08 |
| Seventh layer (protective layer) | |
| Gelatin | 0.70 |
| Acrylic modified copolymer of polyvinyl alcohol (modification degree: 17%) | 0.04 |
| Liquid paraffin | 0.01 |
| Surfactant (Cpd-13) | 0.01 |
| Polydimethylsiloxane | 0.01 |
| Silicon dioxide | 0.003 |

Each of the samples thus prepared was exposed in a similar manner to Test 1 of Example 1 and its color development processing was conducted in a super rapid processing in accordance with the below-described development processing B.

[Processing B]

Each of the photosensitive materials was processed into a roll of 127 mm wide. By using a remodel of a mini-labo printer processor "PP350" (product of Fuji Photo Film Co., Ltd.) capable of changing processing time and processing temperature, imagewise exposure of a negative film having an average density to the photosensitive material sample was conducted. Continuous processing (running test) was conducted by the below-described processing step until the color developing replenisher became 0.5 time the amount of the color developing tank capacity.

| Processing step | Temp. | Time | Replenished amount* |
|---|---|---|---|
| Color development | 45.0° C. | 15 sec | 45 mL |
| Bleaching and fixing | 40.0° C. | 15 sec | 35 mL |
| Rinse (1) | 40.0° C. | 8 sec | — |
| Rinse (2) | 40.0° C. | 8 sec | — |
| Rinse (3)** | 40.0° C. | 8 sec | — |
| Rinse (4)** | 38.0° C. | 8 sec | 21 mL |
| Drying | 80° C. | 15 sec | |

Note)
*Replenished amount per m² of the photosensitive material
**Rinse cleaning system "RC50D" (reverse osmosis membrane module, a product of Fuji Photo Film Co., Ltd.) was installed in Rinse (3). The rinsing solution in Rinse (3) was taken out, and supplied to RC50D by a pump. The solution thus permeated in the tank was supplied to Rinse (4) and the concentrated solution was returned back to Rinse (3). The pressure of the pump was adjusted to keep the feeding rate of the solution to the reverse osmosis membrane module at from 50 to 300 mL/min, and the system was circulated for 10 hours a day at a controlled temperature. Rinsing was conducted in a 4-tank countercurrent system from (1) to (4).

Each processing solution has the following composition:

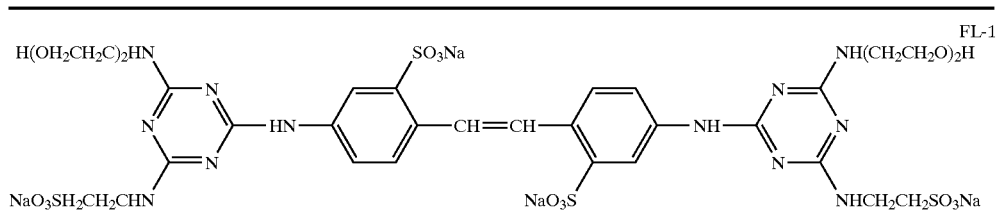

FL-1

| | [Tank solution] | [Replenisher solution] |
|---|---|---|
| [Color developer solution] | | |
| Water | 800 mL | 600 mL |
| Fluorescent brightener (FL-1) | 5.0 g | 8.5 g |
| Triisopropanolamine | 8.8 g | 8.8 g |
| Sodium p-toluenesulfonate | 20.0 g | 20.0 g |
| Ethylenediaminetetraacetic acid | 4.0 g | 4.0 g |
| Sodium sulfite | 0.10 g | 0.50 g |
| Potassium chloride | 10.0 g | — |
| Sodium 4,5-dihydroxybenzene-1,3-disulfonate | 0.50 g | 0.50 g |
| Disodium-N,N-bis(sulfonatoethyl)hydroxylamine | 8.5 g | 14.5 g |
| 4-Amino-3-methyl-N-ethyl-N-(β-methane-sulfonamidoethyl)aniline.3/2 sulfate.monohydrate | 10.0 g | 22.0 g |
| Potassium carbonate | 26.3 g | 26.3 g |
| Water (total amount when water is added) | 1000 ml | 1000 ml |
| PH (at 25° C./adjusted with sulfuric acid or KOH) | 10.35 | 12.6 |
| [Bleaching and fixing solution] | | |
| Water | 800 mL | 800 mL |
| Ammonium thiosulfate (750 g/mL) | 107 mL | 214 mL |
| Succinic acid | 29.5 g | 59.0 g |
| Ammonium ethylenediaminetetraacetoferrate (III) | 47.0 g | 94.0 g |
| Ethylenediaminetetraacetic acid | 1.4 g | 2.8 g |
| Nitric acid (67%) | 17.5 g | 35.0 g |
| Imidazole | 14.6 g | 29.2 g |
| Ammonium sulfite | 16.0 g | 32.0 g |
| Potassium metabisulfite | 23.1 g | 46.2 g |
| Water (total amount when water is added) | 1000 mL | 1000 mL |
| PH (at 25° C./adjusted with nitric acid or aqueous ammonia) | 6.00 | 6.00 |
| [Rinsing solution] | | |
| Chlorinated sodium isocyanurate | 0.02 g | 0.02 g |
| Deionized water (conductivity: 5 μs/cm or less) | 1000 mL | 1000 mL |
| pH (25° C.) | 6.5 | 6.5 |

By using Samples (301) to (326), an image was formed by laser scanning exposure. As laser light sources, employed were 473 nm obtained by converting the wavelength of an YAG solid state laser (oscillation wavelength: 946 nm), which uses a semiconductor laser GaAlAs (oscillation wavelength: 808.5 nm) as the excitation light source, with SHG crystal of $LiNbO_3$ having a reversal domain structure, 532 nm obtained by converting the wavelength of an $YVO_4$ solid state laser (oscillation wavelength: 1,064 nm), which uses a semiconductor laser GaAlAs (oscillation wavelength: 808.7 nm) as the excitation light source, with SHG crystal of $LiNbO_3$ having a reversal domain structure, and AlGaInP (oscillation wavelength: about 680 nm, "Type No. LN9R20; product of Matsushita Electric Industrial Co., Ltd.). Each of three color laser beams was permitted to transfer vertically based on the scanning direction by a polygonal mirror and carry out successive scanning exposure on the sample. Since the temperature of the semiconductor laser was maintained constant by utilizing a Peltier element, fluctuations in light amount depending on the temperature of the semiconductor laser are suppressed. The effective beam diameter was 80 μm, the scanning pitch was 42.3 μm (600 dpi) and the average exposure time per pixel was $1.7 \times 10^{-7}$ seconds.

After exposure, the samples were subjected to Color development Processing B. The samples of this Example exhibited high sensitivity similar to those of Example 2 in high intensity exposure, suggesting that they are suited also for the image formation by using laser scanning exposure.

According to the present invention, emulsions which are high in gradation while minimized in desensitization and latent-image sensitization are available. In addition, by the present invention, high intensity reciprocity law failure can be improved, whereby a photosensitive material having high maximum density can be provided.

The present invention will hereinafter be described in further detail by synthesis examples of novel metal complexes and application examples of them to a photosensitive material.

Example II-1

Synthesis of $K_3[IrCl_5(N(NC)_2)]$ (1)

(Present Invention)

In 4.5 mL of water were dissolved 300 mg (0.64 mmol) of $K_2[IrCl_5H_2O]$ and 170 mg (1.91 mmol) of $NaN(CN)_2$. The resulting solution was stirred at room temperature in a dark place for 6 days, followed by the addition of ethanol. The solid thus precipitated was collected by filtration. After washing with water and EtOH, the solid was air dried, whereby 360 mg of crude crystals of the target product were obtained. The crude crystals were dissolved in water. Ethanol was added to the resulting solution, whereby 240 mg (0.45 mmol) of $K_3[IrCl_5(N(NC)_2]$ was obtained as a purified product (yield: 69%).

Elementary analysis for $C_2N_3Cl_5IrK_3=552.82$; Calculated: C; 4.3, N; 8.6, Cl; 32.1 (%). Found: C; 4.4, N; 7.7, Cl; 32.4 (%).

(Referential Example)

In 4.5 mL of water were dissolved 334 mg (0.64 mmol) of $K_2[IrCl_6]$ and 170 mg (1.91 mmol) of $NaN(CN)_2$. The resulting solution was stirred at room temperature in a dark place for 6 days, followed by the addition of ethanol. The solid thus precipitated was collected by filtration. After washing with water and EtOH, the solid was air dried, whereby 373 mg of crude crystals of the target product were obtained. The crude crystals were dissolved in water. Ethanol was added to crystallize the resulting solution, whereby 251 mg of $K_3[IrCl_5(N(NC)_2]$ was obtained. As a result of analysis by HPLC, however, it was proved that at least 5% of the raw material $IrCl_6^{3-}$ remained. Since this $IrCl_6^{3-}$ was not desired from the viewpoint of photographic performance (it presumably causes desensitization), purification by crystallization was repeated until the purity of the crystals became the same level with that of the sample obtained by the invention process by using $K_2[IrCl_5(H_2O)]$. As a result, 25 mg of the target product was obtained (yield: 7%).

The sample synthesized by the preparation process of the present invention was utterly free of $IrCl_6^{3-}$, which was harmful for the photographic performance, and proved to be preferable compared with that obtained in Referential Example.

Example II-2

Synthesis of $K_3[IrCl_5(N(NC)_2)]$ (2)

In 4.5 mL of water were dissolved 300 mg (0.64 mmol) of $K_2[IrCl_5(H_2O)]$ and 580 mg (6.50 mmol) of $NaN(CN)_2$. The resulting solution was stirred at room temperature in a dark place for 5 days, followed by the addition of ethanol. The solid thus precipitated was collected by filtration. After washing with water and EtOH, the solid was air dried, whereby 371 mg of crude crystals of the target product were obtained. The crude crystals were dissolved in water. Ethanol was added to the resulting solution, whereby 259 mg (0.49 mmol) of $K_3[IrCl_5(N(NC)_2]$ was obtained as a purified product (yield: 74%).

Elementary analysis for $C_2N_3Cl_5IrK_3=552.82$;

Calculated: C; 4.3, N; 8.6, Cl; 32.1 (%).

Found: C; 4.5, N; 7.8, Cl; 32.2 (%).

It has been proved that in the synthesis process of the present invention, reaction proceeded speedily, and effectively in a good yield by the addition of a ligand in large excess (compared with the invention product of Example II-1).

Example II-3

Synthesis of $Cs_3[IrCl_5(N(NC)_2)]$

In 4.5 mL of water were dissolved 300 mg (0.64 mmol) of $K_2[IrCl_5(H_2O)]$ and 580 mg (6.50 mmol) of $NaN(CN)_2$. The resulting solution was stirred at room temperature in a dark place for 6 days, followed by the addition of ethanol. The solid thus precipitated was collected by filtration. After washing with water and EtOH, the solid was air dried, whereby 371 mg of crude crystals of the target product were obtained. The crude crystals were dissolved in water. To the resulting solution were added 270 mg (1.61 mmol) of CsCl and ethanol, whereby 266 mg (0.50 mmol) of $Cs_3[IrCl_5(N(NC)_2]$ was obtained as a purified product (yield: 76%).

Elementary analysis for $C_2N_3Cl_5Cs_3Ir=834.25$; Calculated: C; 2.9, N; 5.0, Cl; 21.2 (%). Found: C; 2.8, N; 5.0, Cl; 21.0 (%).

Use of $Cs^+$ as a counter cation heightened the yield compared with the use of $K^+$.

Example II-4

Synthesis of $K_2[IrCl_5(2,5\text{-dichloro-}1,3,4\text{-thiadiazole})]$

In 9 mL of water and 1 mL of dimethylacetamide were dissolved 300 mg (0.64 mmol) of $K_2[IrCl_5(H_2O)]$ and 300 mg (1.94 mmol) of 2,5-dichloro-1,3,4-thiadiazole. The resulting solution was stirred at room temperature in a dark place for 3 days, followed by the addition of ethanol. The solid thus precipitated was collected by filtration. After washing with water and EtOH, the solid was air dried, whereby 253 mg of crude crystals of the target product were obtained. The crude crystals were dissolved in water. Ethanol was added to the resulting solution, whereby 229 mg (0.39 mmol) of $K_2[IrCl_5(2,5\text{-dichloro-}1,3,4\text{-thiadiazole})]$ was obtained as a purified product (yield: 59%).

Elementary analysis for $C_2N_2Cl_7IrK_3S=602.69$; Calculated: C; 4.0, N; 4.6, Cl; 41.2 (%). Found: C; 3.8, N; 4.5, Cl; 41.3 (%).

Example II-5

Synthesis of $K_2[IrCl_5(3,5\text{-dichloro-}1,2,4\text{-thiadiazole})]$

In 4.5 mL of water and 0.5 mL of dimethylacetamide were dissolved 300 mg (0.64 mmol) of $K_2[IrCl_5(H_2O)]$ and 300 mg (1.94 mmol) of 3,5-dichloro-1,2,4-thiadiazole. The resulting solution was stirred at room temperature in a dark place for 3 days, followed by the addition of ethanol. The solid thus precipitated was collected by filtration. After washing with water and EtOH, the solid was air dried, whereby 270 mg of crude crystals of the target product were obtained. The crude crystals were dissolved in water. Ethanol was added to the resulting solution, whereby 230 mg (0.38 mmol) of $K_2[IrCl_5(3,5\text{-dichloro-}1,2,4\text{-thiadiazole})]$ was obtained as purified product (yield: 60%).

Elementary analysis for $C_2N_2Cl_7IrK_2S=602.69$; Calculated: C; 4.0, N; 4.6, Cl; 41.2 (%). Found: C; 3.9, N; 4.5, Cl; 41.3 (%).

Example II-6

Synthesis of $K_2[IrCl_5(2\text{-bromo-5-chloro-1,3,4-thiadiazole})]$

In 9 mL of water and 1 mL of dimethylacetamide were dissolved 300 mg (0.64 mmol) of $K_2[IrCl_5(H_2O)]$ and 380 mg (1.91 mmol) of 2-bromo-5-chloro-1,3,4-thiadiazole. The resulting solution was stirred at room temperature in a dark place for 6 days, followed by the addition of ethanol. The solid thus precipitated was collected by filtration. After washing with water and EtOH, the solid was air dried, whereby 275 mg of crude crystals of the target product were obtained. The crude crystals were dissolved in water. Ethanol was added to the resulting solution, whereby 226 mg (0.36 mmol) of $K_2[IrCl_5(2\text{-bromo-5-chloro-1,3,4-thiadiazole})]$ was obtained as a purified product (yield: 55%).

Elementary analysis for $C_2N_2BrCl_6IrK_2S=647.14$; Calculated: C; 3.7, N; 4.3, Cl; 32.9 (%). Found: C; 3.4, N; 3.9, Cl; 32.5 (%).

Example II-7

Synthesis of $K_2[IrCl_5(2\text{-chloro-5-fluoro-1,3,4-thiadiazole})]$

In 9 mL of water and 1 mL of dimethylacetamide were dissolved 300 mg (0.64 mmol) of $K_2[IrCl_5(H_2O)]$ and 267 mg (1.92 mmol) of 2-chloro-5-fluoro-1,3,4-thiadiazole. The resulting solution was stirred at room temperature in a dark place for 5 days, followed by the addition of ethanol. The solid thus precipitated was collected by filtration. After washing with water and EtOH, the solid was air dried, whereby 280 mg of crude crystals of the target product were obtained. The crude crystals were dissolved in water. Ethanol was added to the resulting solution, whereby 220 mg (0.38 mmol) of $K_2[IrCl_5(2\text{-chloro-5-fluoro-1,3,4-thiadiazole})]$ was obtained as a purified product (yield: 60%).

Elementary analysis for $C_2N_2Cl_6FIrK_2S=586.24$; Calculated: C; 4.1, N; 4.8, Cl; 36.3 (%). Found: C; 3.9, N; 4.6, Cl; 36.2 (%).

Example II-8

Synthesis of $K_2[IrCl_5(2,5\text{-difluoro-1,3,4-thiadiazole})]$

In 9 mL of water and 1 mL of dimethylacetamide were dissolved 300 mg (0.64 mmol) of $K_2[IrCl_5(H_2O)]$ and 240 mg (1.97 mmol) of 2,5-difluoro-1,3,4-thiadiazole. The resulting solution was stirred at room temperature in a dark place for 5 days, followed by the addition of ethanol. The solid thus precipitated was collected by filtration. After washing with water and EtOH, the solid was air dried, whereby 281 mg of crude crystals of the target product were obtained. The crude crystals were dissolved in water. Ethanol was added to the resulting solution, whereby 211 mg (0.37 mmol) of $K_2[IrCl_5(2,5\text{-difluoro-1,3,4-thiadiazole})]$ was obtained (yield: 58%).

Elementary analysis for $C_2N_2Cl_5F_2IrK_2S=569.78$; Calculated: C; 4.2, N; 4.9, Cl; 31.1 (%). Found: C; 4.3, N; 5.1, Cl; 31.4 (%).

Example II-9

Synthesis of $K_2[IrCl_5(2\text{-bromo-5-fluoro-1,3,4-thiadiazole})]$

In 9 mL of water and 1 mL of dimethylacetamide were dissolved 300 mg (0.64 mmol) of $K_2[IrCl_5(H_2O)]$ and 350 mg (1.91 mmol) of 2-bromo-5-fluoro-1,3,4-thiadiazole. The resulting solution was stirred at room temperature in a dark place for 5 days, followed by the addition of ethanol. The solid thus precipitated was collected by filtration. After washing with water and EtOH, the solid was air dried, whereby 306 mg of crude crystals of the target product were obtained. The crude crystals were dissolved in water. Ethanol was added to the resulting solution, whereby 204 mg (0.32 mmol) of $K_2[IrCl_5(2\text{-bromo-5-fluoro-1,3,4-thiadiazole})]$ was obtained as a purified product (yield: 51%).

Elementary analysis for $C_2N_2BrCl_5FIrK_2S=630.69$; Calculated: C; 3.8, N; 4.4, Cl; 28.1 (%). Found: C; 3.6, N; 4.3, Cl; 28.3 (%).

Example II-10

Synthesis of $K_2[IrCl_5(NH_2C(=S)NH_2)]$

In 4.5 mL of water were dissolved 300 mg (0.64 mmol) of $K_2[IrCl_5(H_2O)]$ and 146 mg (1.91 mmol) of thiourea. The resulting solution was stirred at 80° C. for 1 hour, followed by the addition of ethanol. The solid thus precipitated was collected by filtration. After washing with water and EtOH, the solid was air dried, whereby 270 mg (0.52 mmol) of $K_2[IrCl_5(NH_2C(=S)NH_2)]$ was obtained (yield: 81%).

Elementary analysis for $CH_4N_2Cl_5IrK_2S=523.81$; Calculated: C; 2.3, N; 5.3, Cl; 33.8 (%). Found: C; 2.5, N; 5.4, Cl; 32.9 (%).

Example II-11

Synthesis of $K_2[IrCl_5(NH_2C(=NH)SCH_3)]$

In 4.5 mL of water were dissolved 300 mg (0.64 mmol) of $K_2[IrCl_5(H_2O)]$ and 270 mg (0.97 mmol) of S-methylthiourea sulfate. The resulting solution was stirred at 80° C. for 1 hour, followed by the addition of ethanol. The solid thus precipitated was collected by filtration. After washing with water and EtOH, the solid was air dried, whereby 281 mg of crude crystals of the target product were obtained. The resulting crude crystals were dissolved in water. Ethanol was added to the resulting solution to crystallize the same, whereby 214 mg (0.40 mmol) of $K_2[IrCl_5(NH_2C(=NH)SCH_3)]$ was obtained as a purified product (yield: 61%).

Elementary analysis for $C_2H_6N_2Cl_5IrK_2S=537.83$; Calculated: C; 4.5, N; 5.2, Cl; 33.0 (%). Found: C; 4.3, N; 4.8, Cl; 32.4 (%).

Example II-12

Synthesis of $K_2[IrCl_5(CH_3NHC(=S)NH_2)]$

In 4.5 mL of water were dissolved 300 mg (0.64 mmol) of $K_2[IrCl_5(H_2O)]$ and 170 mg (1.93 mmol) of N-methyl thiourea. The resulting solution was stirred at 80° C. for 1 hour, followed by the addition of ethanol. The solid thus precipitated was collected by filtration. After washing with water and EtOH, the solid was air dried, whereby 220 mg (0.41 mmol) of $K_2[IrCl_5(NHC(=S)NH_2)]$ was obtained (yield: 64%).

Elementary analysis for $C_2H_6N_2Cl_5IrK_2S=567.83$; Calculated: C; 4.5, N; 5.2, Cl; 33.0 (%). Found: C; 4.4, N; 5.0, Cl; 32.9 (%).

Example II-13

Synthesis of $Cs_2[IrCl_5(S=P(NH_2)_3)]$

In 3.0 mL of water were dissolved 200 mg (0.43 mmol) of $K_2[IrCl_5(H_2O)]$ and 150 mg (1.35 mmol) of $S=P(NH_2)_3$. After the resulting solution was stirred at room temperature for 2 days in a dark place, CsCl and ethanol were added to the reaction mixture. The solid thus precipitated was collected by filtration. After washing with water and EtOH, the solid was air dried. The resulting crude crystals were recrystallized from water, whereby 182 mg (0.24 mmol) of $Cs_2[IrCl_5(S=P(NH_2)_3]$ was obtained (yield: 57%).

Elementary analysis for $H_6N_2Cl_5Cs_2IrPS=746.41$; Calculated: N; 5.6, Cl; 23.7 (%). Found: N; 5.6, Cl; 23.8 (%).

Example II-14

Synthesis of $K_2[IrCl_5(S=P(NH_2)_2(OH))]$

In 3.0 mL of water were dissolved 200 mg (0.43 mmol) of $K_2[IrCl_5(H_2O)]$ and 150 mg (1.35 mmol) of $S=P(NH_2)_3$. After the resulting solution was stirred at room temperature for 3 days in a dark place, ethanol was added to the reaction mixture. The solid thus precipitated was collected by filtration. After washing with water and EtOH, the solid was air dried, whereby 158 mg (0.28 mmol) of $K_2[IrCl_5(S=P(NH_2)_2(OH))]$ was obtained (yield: 65%).

Elementary analysis for $H_5N_2Cl_5K_2IrOPS=559.78$; Calculated: N; 5.0, Cl; 31.7 (%). Found: N; 4.9, Cl; 31.6 (%).

Example II-15
<Emulsion 1-1; Preparation of Cubic Silver Chloride Sample (1)> (Comparative Example)

To a 5% aqueous solution of lime-processed gelatin was added 5.6 g of sodium chloride, followed by the addition of 42.8 mL of 1N sulfuric acid and 1.1 mL of a 1% aqueous solution of N,N'-dimethylimidazolidine-2-thione. An aqueous solution (241.2 mL) containing 0.21 mol of silver nitrate and an aqueous solution (241.2 mL) containing 0.21 mol of sodium chloride were added to the resulting mixture and they were mixed at 61° C. over 24 minutes under stirring. To the reaction mixture were added an aqueous solution (720 mL) containing 1.91 mol of silver nitrate and an aqueous solution (720 mL) containing 1.91 mol of sodium chloride over 40 minutes, whereby cubic grains having an average grain size of 0.62 μm (variation coefficient: 10%) were obtained. The grains were then precipitated and desalted by washing at 40° C. Further, 168.0 g of lime-processed gelatin was added to the emulsion to adjust its pH and pAg to 7.3 and 5.6, respectively. To the emulsion thus obtained were added a gold sensitizer (gold (I) tetrafluoroborate bis (1,4,5-trimethyl-1,2,4-triazolium-3-thiolato)) in an amount of $1.5×10^{-5}$ mol per mol of silver and a sulfur sensitizer (sodium thiosulfate) in an amount of $6×10^{-7}$ mol per mol of silver. Further, blue-sensitive spectral sensitizing dyes (A and B) were added in amounts of $2.3×10^{-4}$ mol and $1.5×10^{-4}$ mol, each per mole of silver, respectively, whereby the emulsion was optimally subjected to chemical sensitization and spectral sensitization at 60° C. Further, 1-(5-methylureidophenyl)-5-mercaptotetrazole was added in an amount of $4.4×10^{-4}$ mol per mol of silver, whereby Emulsion 1-1 was prepared.

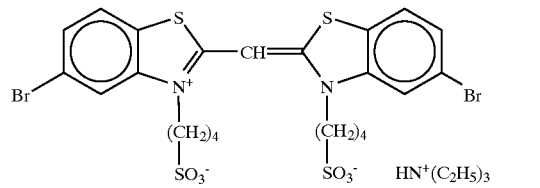
(Sensitizing dye A)

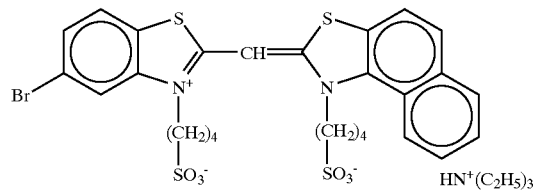
(Sensitizing dye B)

<Emulsion 1-2; Preparation of Cubic Silver Chloride Sample Doped with $[IrCl_6]^{3-}$> (Comparative Example)

In a similar manner to that employed for Emulsion 1-1 except that $[IrCl_6]^{3-}$ was added to the 90 to 95% portion, in terms of grain volume, from the center of the grain of Emulsion 1-1 in an amount of $3×10^{-8}$ mol based on the amount of silver added to the emulsion, Emulsion 1-2 was prepared.

<Emulsion 1-3; Preparation of Cubic Silver Chloride Sample Doped with $[IrCl_6]^{3-}$ and $[Ru(CN)_6]^{4-}$> (Comparative Example)

In a similar manner to that employed for Emulsion 1-except that $[IrCl_6]^{3-}$ was added to the 90 to 95% portion, in terms of grain volume, from the center of the grain of Emulsion 1-1 in an amount of $3×10^{-8}$ mol based on the amount of silver added to the emulsion and $[Ru(CN)_6]^{4-}$ was added to the 80 to 97% portion, in terms of grain volume, from the center of the grain of Emulsion 1-1 in an amount of $5×10^{-5}$ mol based on the amount of silver added to the emulsion, Emulsion 1-3 was prepared.

<Emulsion 1-4; Preparation of Cubic Silver Chloride Sample Doped with $[IrCl_5(thiazole)]^{2-}$> (Comparative Example)

In a similar manner to that employed for Emulsion 1-1 except that $[IrCl_5(thiazole)]^{2-}$ was added to the 90 to 95% layer of Emulsion 1-1 in an amount of $3×10^{-8}$ mol based on the amount of silver added to the emulsion, Emulsion 1-4 was prepared.

<Emulsions 1-5 to 1-15: Preparation of Cubic Silver Chloride Samples Doped with $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$, respectively> (Invention Products)

In a similar manner to that employed for Emulsion 1-1 except that each of $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ was added to the 90 to 95% portion, in terms of grain volume, from the center of the grain of Emulsion 1-1 in an amount of 3×10⁻⁸ mol based on the amount of silver added to the emulsion, each of Emulsions 1-5 to 1-15 was prepared, respectively.

<Emulsions 1-16 to 1-26: Preparation of Cubic Silver Chloride Samples Doped with $[IrCl_5(N(CN)_2)]^{3-}$, $[IrCl_5(S(CN)_2)]^{2-}$, $[Ircl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5(1,2,4]\text{-thiadiazole})]^{2-}$, and $[Ru(CN)_6]^{4-}$, respectively> (Invention Products)

In a similar manner to that employed for Emulsion 1-1 except that each of $[IrCl_5(N(CN)_2)]^{3-}$, $[IrCl_5(S(CN)_2)]^{2-}$, $[IrCl_5(NH_2C(=S)NH_2)]^{2-}$, $[IrCl_5(NH_2C(SCH_3)NH)]^{2-}$, $[IrCl_5([1,3,4]\text{-thiadiazole})]^{2-}$ and $[IrCl_5([1,2,4]\text{-thiadiazole})]^{2-}$ was added to the 90 to 95% portion, in terms of grain volume, from the center of the grain of Emulsion 1-1 in an amount of 3×10⁻⁸ mol based on the amount of silver added to the emulsion; and $[Ru(CN)_6]^{4-}$ was added to the 80 to 97% portion, in terms of grain volume, from the center of the grain of Emulsion 1-1 in an amount of 5×10⁻⁵ mol based on the amount of silver added to the emulsion, each of Emulsions 1-16 to 1-26 were prepared, respectively.

After corona discharge treatment was given to the surface of a paper support laminated on both sides with a polyethylene resin, a gelatin undercoat layer containing sodium dodecylbenzenesulfonate was formed thereon. Then, first to seventh photographic constituent layers were coated successively on the undercoat layer to prepare silver halide color photosensitive material samples (101) to (126) having the following layer composition. The coating solution of each constituent layer was prepared as described below.

Preparation of Coating Solution for First Layer:

A yellow coupler (ExY) (57 g), 7 g of a color image stabilizer (Cpd-1), 4 g of a color image stabilizer (Cpd-2) 7 g of a color image stabilizer (Cpd-3), and 2 g of a color image stabilizer (Cpd-8) were dissolved in 21 g of a solvent (Solv-1) and 80 ml of ethyl acetate. The resulting solution was emulsified and dispersed by a high-speed stirring emulsifier (dissolver) in 220 g of a 23.5 wt % aqueous gelatin solution containing 4 g of sodium dodecylbenzenesulfonate, and water was added thereto to obtain 900 g of Emulsified Dispersion A.

Emulsified Dispersion A thus obtained and Emulsion 1-1 were mixed and dissolved to prepare a coating solution for first layer having the composition as shown below. The coating amount of the emulsion is in terms of silver.

The coating solutions for the second to seventh layers were prepared in a similar manner to that employed for the coating solution for first layer. As a gelatin hardener for each layer, 1-oxy-3,5-dichloro-s-triazine sodium salt (H-1), (H-2) or (H-3) was used. Further, Antiseptic Ab-1, Ab-2, Ab-3 and Ab-4 were added to each layer so that the total amount would be 15.0 mg/m², 60.0 mg/m², 5.0 mg/m² and 10.0 mg/m², respectively.

(H-1) Hardener

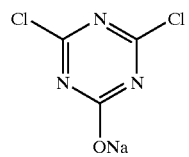

(used in an amount of 1.4% by mass based on gelatin)

(H-2) Hardener

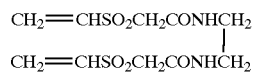

(H-3) Hardener

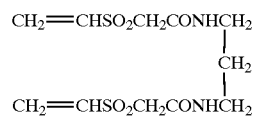

(Ab-1) Antiseptic    (Ab-2) Antiseptic

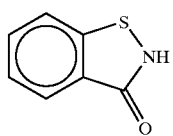 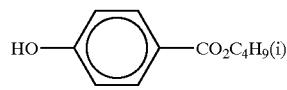

(Ab-3) Antiseptic)

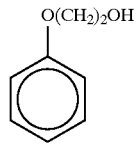

(Ab-4) Antiseptic)
A 1:1:1:1 mixture of a, b, c and d (molar ratio)

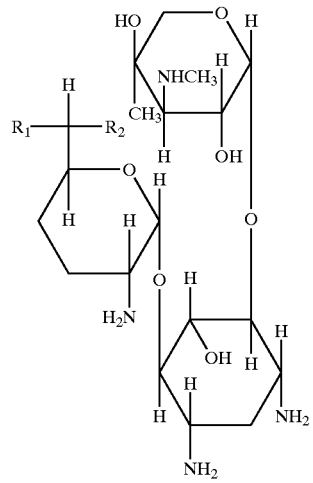

| | $R_1$ | $R_2$ |
|---|---|---|
| a | —CH₃ | —NHCH₃ |
| b | —CH₃ | —NH₂ |
| c | —H | —NH₂ |
| d | —H | —NHCH₃ |

The below-described spectral sensitizing dyes were added to the silver chlorobromide emulsions of the green-sensitive and red-sensitive emulsion layers, respectively. Green-sensitive emulsion layer Sensitizing dye D

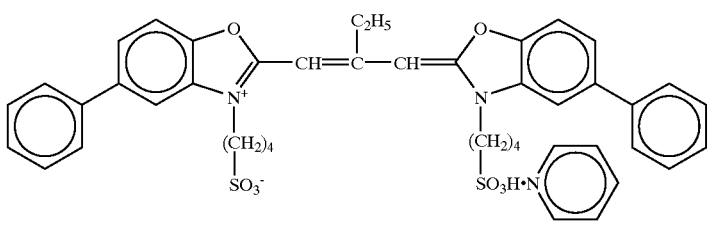

Sensitizing dye E

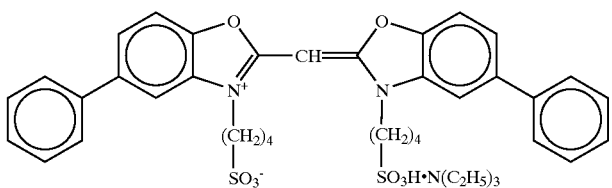

Sensitizing dye F

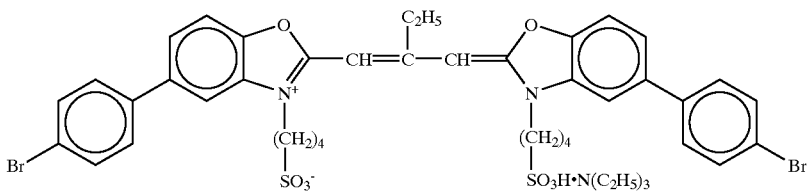

(Sensitizing dye D was added in an amount of $3.0 \times 10^{-4}$ Mol to a large grain size emulsion, and $3.6 \times 10^{-4}$ Mol to a small grain size emulsion, each per mol of silver halide. Sensitizing dye E was added in an amount of $4.0 \times 10^{-5}$ mol to a large grain size emulsion, and $7.0 \times 10^{-5}$ mol to a small grain size emulsion, each per mol of silver halide. Sensitizing dye F was added in an amount of $2.0 \times 10^{-4}$ Mol to a large grain size emulsion, and in an amount of $2.8 \times 10^{-4}$ mol to a small grain size emulsion, each per mol of silver halide)

Red-Sensitive Emulsion Layer

Sensitizing dye G

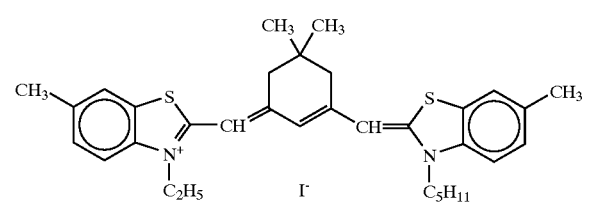

Sensitizing dye H

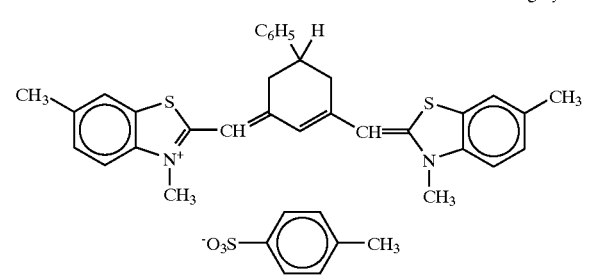

(Sensitizing dye G and Sensitizing dye H were each added in an amount of $8.0 \times 10^{-5}$ mol to a large grain size emulsion, and $10.7 \times 10^{-5}$ mol to a small grain size emulsion, each per mol of silver halide).

Further, the below-described Compound I was added to the red-sensitive emulsion layer in an amount of $3.0 \times 10^{-3}$ mol per mol of silver halide.

Compound I

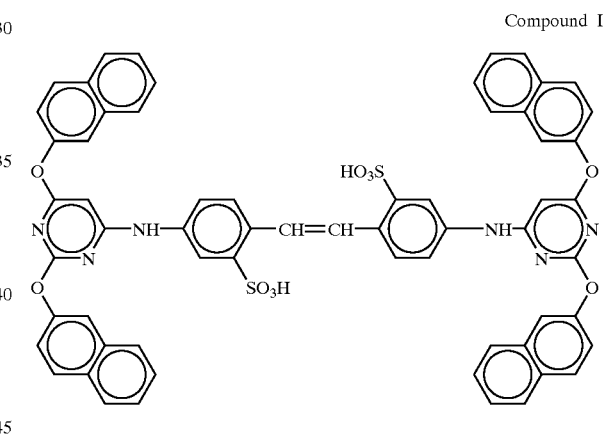

Further, 1-(3-methylureidophenyl)-5-mercaptotetrazole was added to the green-sensitive emulsion layer and the red-sensitive emulsion layer in amounts of $3.3 \times 10^{-4}$ mol, $1.0 \times 10^{-3}$ mol and $5.9 \times 10^{-4}$ mol, respectively, per mol of silver halide. It was also added to the second, fourth, sixth and seventh layers in amounts of 0.2 mg/m$^2$, 0.2 mg/m$^2$, 0.6 mg/m$^2$ and 0.1 mg/m$^2$, respectively.

To the blue-sensitive emulsion layer and the green-sensitive emulsion layer was added 4-hydroxy-6-methyl-1,3,3a,7-tetrazaindene in amounts of $1 \times 10^{-4}$ mol and $2 \times 10^{-4}$ mol, respectively, per mol of silver halide.

To the red-sensitive emulsion layer was added 0.05 g/m$^2$ of a copolymer latex of methacrylic acid and butyl acrylate (weight ratio: 1:1, average molecular weight: 200,000 to 400,000).

To the second, fourth and sixth layers was added disodium catechol-3,5-disulfonate in amounts of 6 mg/m$^2$, 6 mg/m$^2$ and 18 mg/m$^2$, respectively.

The below-described dyes were added in order to prevent irradiation (the numerals in parentheses represent the coating amount).

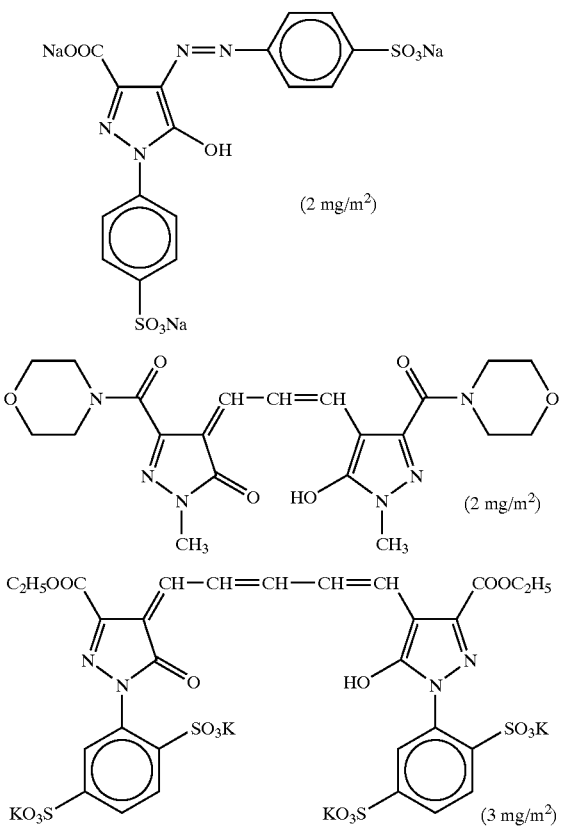

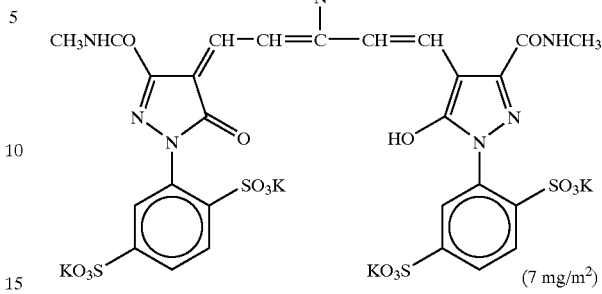

(Layer Constitution)

The constitution of each layer is described below. The numeral represents the coating amount (g/m$^2$). The numeral for silver halide emulsion represents the coating amount in terms of silver.

Support

Polyethylene-resin-laminated paper [a polyethylene resin on the first layer side contains a white pigment (TiO$_2$ content: 16% by mass, ZnO content: 4% by mass), a fluorescent brightener (4,4'-bis(5-methylbenzoxazolyl)stilbene content: 0.03 wt %), and a bluish dye (ultramarine)).

First Layer (blue-sensitive emulsion layer)

| | |
|---|---|
| Emulsion 1-1 | 0.24 |
| Gelatin | 1.25 |
| Yellow coupler (ExY) | 0.57 |
| Color image stabilizer (Cpd-1) | 0.07 |
| Color image stabilizer (Cpd-2) | 0.04 |
| Color image stabilizer (Cpd-3) | 0.07 |
| Color image stabilizer (Cpd-8) | 0.02 |
| Solvent (Solv-1) | 0.21 |

Second layer (color mixing preventive layer)

| | |
|---|---|
| Gelatin | 0.99 |
| Color mixing preventive (Cpd-4) | 0.09 |
| Color image stabilizer (Cpd-5) | 0.018 |
| Color image stabilizer (Cpd-6) | 0.13 |
| Color image stabilizer (Cpd-7) | 0.01 |
| Solvent (Solv-1) | 0.06 |
| Solvent (Solv-2) | 0.22 |

Third layer (green-sensitive emulsion layer)

| | |
|---|---|
| Silver bromide chloride emulsion Em-1 (cubic emulsion sensitized with gold sulfur, a 1:3 mixture (silver molar ratio) of a large grain size emulsion having an average grain size of 0.45 μm and a small grain size emulsion having an average grain size of 0.35 μm. Variation coefficients of the grain size distribution were 0.10 and 0.08, respectively. Emulsions of both size each contained 0.15 mol % of silver iodide in the vicinity of the grain surface, and 0.4 mol % of silver bromide localized on the grain surface) | 0.14 |
| Gelatin | 1.36 |
| Magenta coupler (ExM) | 0.15 |
| Ultraviolet absorber (UV-A) | 0.14 |

-continued

| | |
|---|---|
| Color image stabilizer (Cpd-2) | 0.02 |
| Color image stabilizer (Cpd-4) | 0.002 |
| Color image stabilizer (Cpd-6) | 0.09 |
| Color image stabilizer (Cpd-8) | 0.02 |
| Color image stabilizer (Cpd-9) | 0.03 |
| Color image stabilizer (Cpd-10) | 0.01 |
| Color image stabilizer (Cpd-11) | 0.0001 |
| Solvent (Solv-3) | 0.11 |
| Solvent (Solv-4) | 0.22 |
| Solvent (Solv-5) | 0.20 |
| Fourth layer (color mixing preventive layer) | |
| Gelatin | 0.71 |
| Color mixing preventive (Cpd-4) | 0.06 |
| Color image stabilizer (Cpd-5) | 0.013 |
| Color image stabilizer (Cpd-6) | 0.10 |
| Color image stabilizer (Cpd-7) | 0.007 |
| Solvent (Solv-1) | 0.04 |
| Solvent (Solv-2) | 0.16 |
| Fifth layer (red-sensitive emulsion layer) | |
| Silver bromide chloride emulsion Em-2 (a cubic emulsion sensitized with gold sulfur; a 5:5 mixture (silver molar ratio) of a large grain size emulsion having an average grain size of 0.40 μm and a small grain size emulsion having an average grain size of 0.30 μm; variation coefficients of the grain size distribution were 0.09 and 0.11 respectively; each emulsion contained 0.1 mol % of silver iodide in the vicinity of the grain surface, and 0.8 mol % of silver bromide localized on the grain surface) | 0.12 |
| Gelatin | 1.11 |
| Cyan coupler (ExC-2) | 0.13 |
| Cyan coupler (ExC-3) | 0.03 |
| Color image stabilizer (Cpd-1) | 0.05 |
| Color image stabilizer (Cpd-6) | 0.06 |
| Color image stabilizer (Cpd-7) | 0.02 |
| Color image stabilizer (Cpd-9) | 0.04 |
| Color image stabilizer (Cpd-10) | 0.01 |
| Color image stabilizer (Cpd-14) | 0.01 |
| Color image stabilizer (Cpd-15) | 0.12 |
| Color image stabilizer (Cpd-16) | 0.03 |
| Color image stabilizer (Cpd-17) | 0.09 |
| Color image stabilizer (Cpd-18) | 0.07 |
| Solvent (Solv-5) | 0.15 |
| Solvent (Solv-8) | 0.05 |
| Sixth layer (ultraviolet absorbing layer) | |
| Gelatin | 0.46 |
| Ultraviolet absorber (UV-B) | 0.45 |
| Compound (S1-4) | 0.0015 |
| Solvent (Solv-7) | 0.25 |
| Seventh layer (protective layer) | |
| Gelatin | 1.00 |
| Acrylic modified copolymer of polyvinyl alcohol (modification degree: 17%) | 0.04 |
| Liquid paraffin | 0.02 |
| Surfactant (Cpd-13) | 0.01 |

(ExY) Yellow coupler
A 70:30 mixture (molar ratio) of

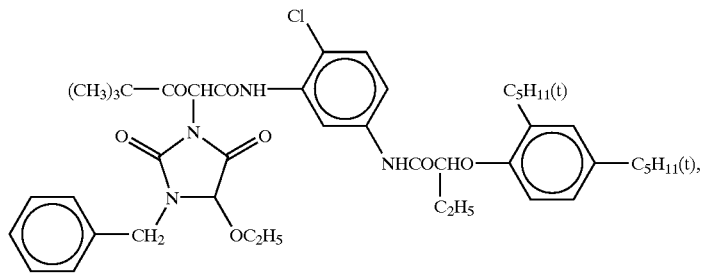

-continued
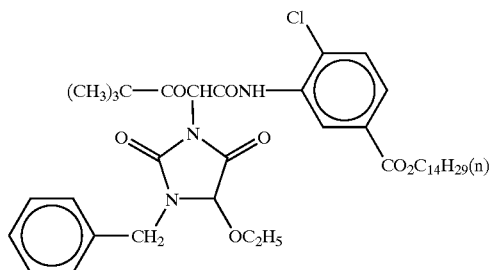
(ExM) Magenta coupler
A 40:40:20 mixture (molar ratio) of
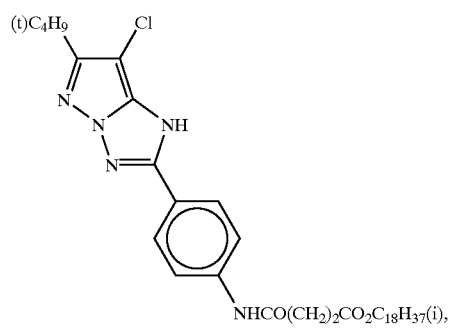
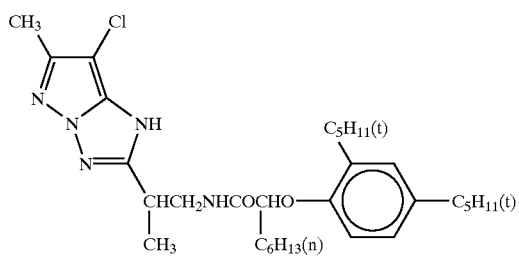

(ExC-2) Cyan coupler
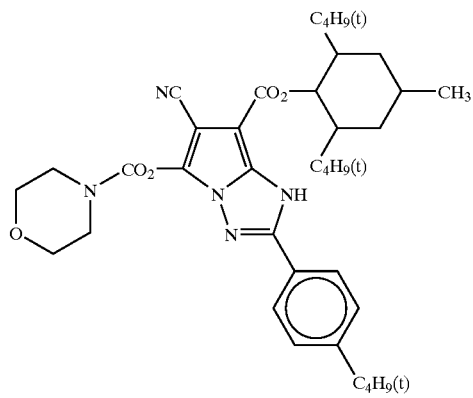
(ExC-3) Cyan coupler
A 50:25:25 mixture (molar ratio) of
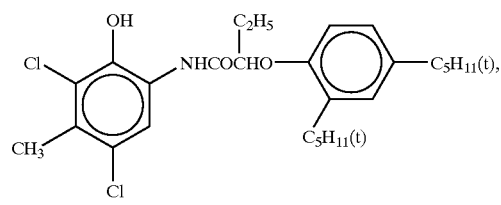
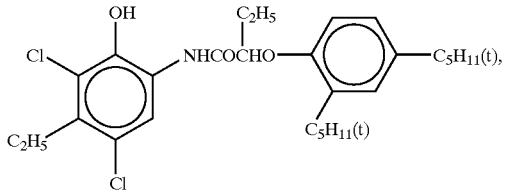
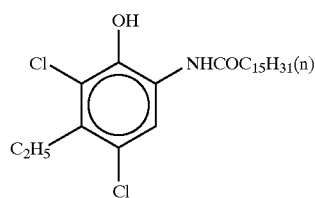
(Cpd-1) Color image stabilizer
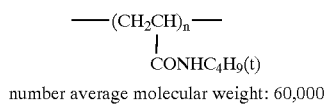
number average molecular weight: 60,000
(Cpd-2) Color image stabilizer
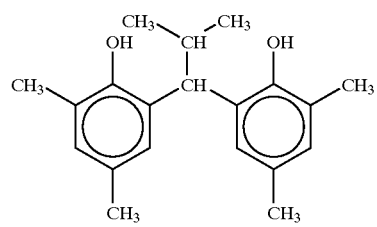

(Cpd-3) Color image stabilizer
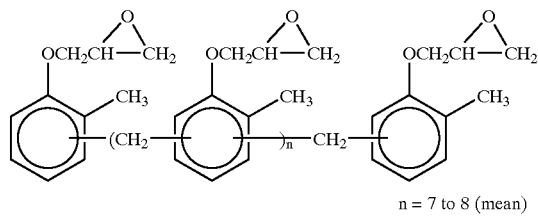
n = 7 to 8 (mean)
(Cpd-4) Color mixing preventive
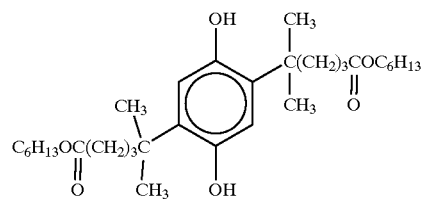
(Cpd-5) Color image stabilizer
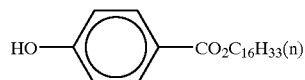
(Cpd-6) Color image stabilizer
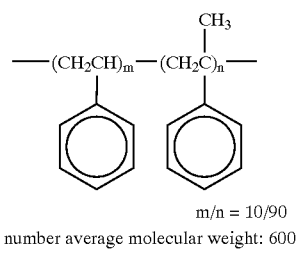
m/n = 10/90
number average molecular weight: 600
(Cpd-7) Color image stabilizer
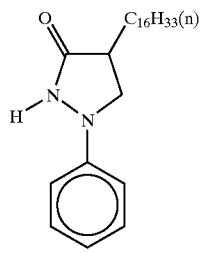
(Cpd-8) Color image stabilizer
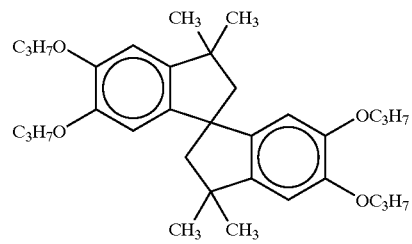

-continued
(Cpd-9) Color image stabilizer
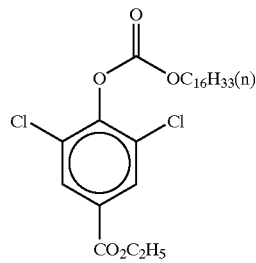
(Cpd-10) Color image stabilizer
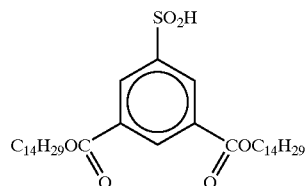
(Cpd-11)
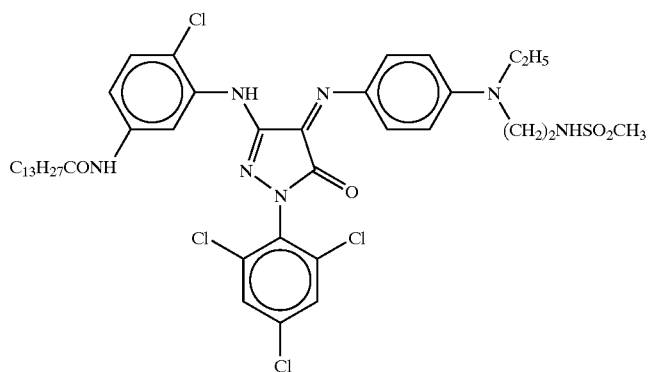
(Cpd-13) Surfactant
A 7:3 mixture (molar ratio) of
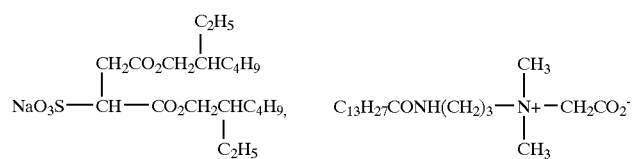
(Cpd-14)
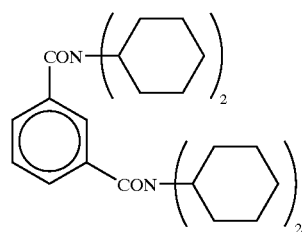
(Cpd-15)
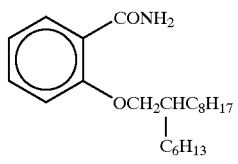

-continued
(Cpd-16)
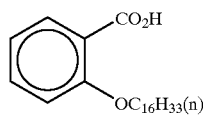
(Cpd-17)
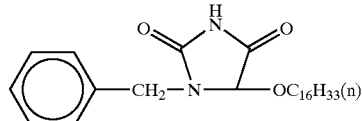
(Cpd-18)
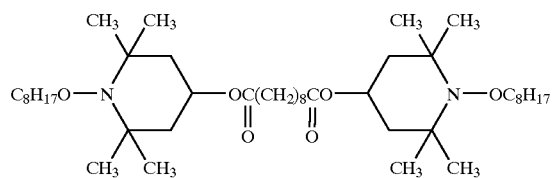
(Cpd-19) Color mixing preventative
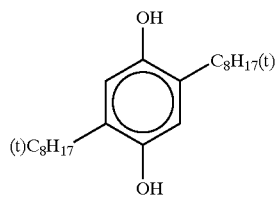
(UV-1) Ultraviolet absorber
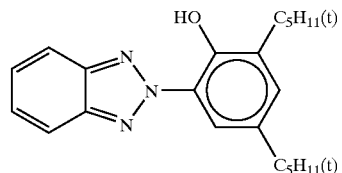
(UV-2) Ultraviolet absorber
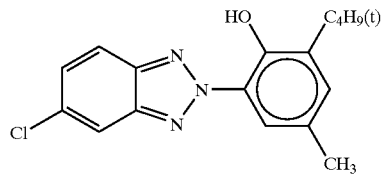
(UV-3) Ultraviolet absorber
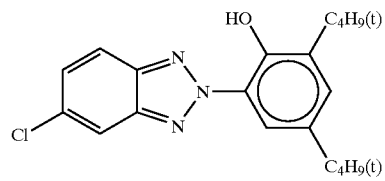
(UV-4) Ultraviolet absorber
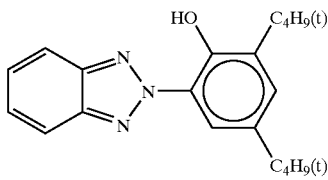
(UV-5) Ultraviolet absorber
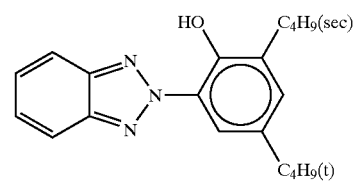
(UV-6) Ultraviolet absorber
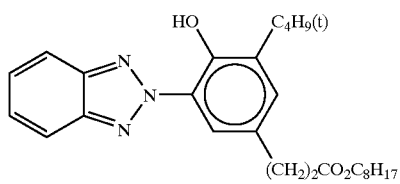

(UV-7) Ultraviolet absorber

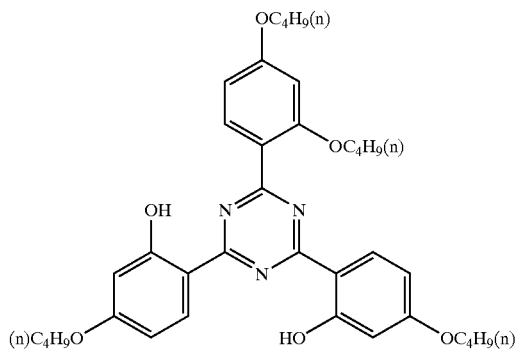

UV-A: a 4:2:2:3 mixture (weight ratio) of UV-1, UV-2, UV-3 and UV-4
UV-B: a 9:3:3:4:5:3 mixture (weight ratio) of UV-1, UV-2, UV-3, UV-4, UV-5 and UV-6
UV-C: a 1:1:1:2 mixture (weight ratio) of UV-2, UV-3, UV-6 and UV-7

(Solv-1)

(Solv-2)

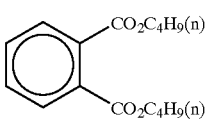

(Solv-3)

(Solv-4)

(Solv-5)

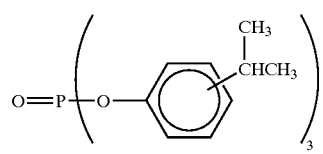

(Solv-7)

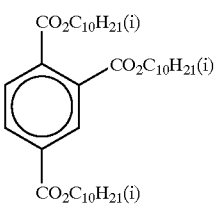

(Solv-8)

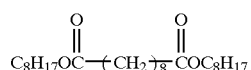

(S1-4)

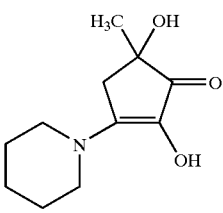

Samples (102) to (126) were prepared in a similar manner to that employed for Sample (101) except that Emulsions 1-2 to 1-26 were used instead of Emulsion 1-1, respectively.

Tests as described below were performed in order to study photographic characteristics of these samples.

Test 1: Sensitometry

Each sample was subjected to gradation exposure for sensitometry by using a sensitometer ("Model FWH" product of Fuji Photo Film Co., Ltd.). An SP-1 filter was attached to the sensitometer and exposure to low illuminance was conducted for 10 seconds.

Each sample was subjected to gradation exposure for sensitometry by using a sensitometer for high intensity exposure ("Model HIE" product of Yamashita Denso Corporation). An SP-1 filter was attached to the sensitometer and exposure to high illuminance was conducted for $10^{-4}$ seconds.

After exposure, each sample was subjected to the following color development processing A.

The processing step was as follows.

[Processing A]

The above-described photosensitive material 101 was processed into a roll of 127 mm wide. After imagewise exposure by using a mini-labo printer processor "PP1258AR" (product of Fuji Photo Film Co., Ltd.), continuous processing (running test) was conducted by the below-described processing step until the color developing replenisher became two times the amount of the color developing tank capacity. The processing using this running solution was designated as processing A.

| Processing step | Temp. | Time | Replenished amount* |
|---|---|---|---|
| Color development | 38.5° C. | 45 sec | 45 mL |
| Bleaching and fixing | 38.0° C. | 45 sec | 35 mL |
| Rinse (1) | 38.0° C. | 20 sec | — |
| Rinse (2) | 38.0° C. | 20 sec | — |
| Rinse (3)** | 38.0° C. | 20 sec | — |
| Rinse (4)** | 38.0° C. | 30 sec | 121 mL |

*Replenished amount per m² of the photosensitive material
**Rinse cleaning system "RC50D" (reverse osmosis membrane module, product of Fuji Photo Film Co., Ltd.) was installed in Rinse (3). The rinsing solution in Rinse (3) was taken out, and supplied to RC50D by a pump. The solution thus permeated through the membrane in the tank was supplied to Rinse (4) and the concentrated solution was returned back to Rinse (3).

The pressure of the pump was adjusted to keep the feeding rate of the solution to the reverse osmosis membrane module at from 50 to 300 ml/min, and the system was circulated for 10 hours a day at a controlled temperature.

(Rinsing was Conducted in a Tank Countercurrent System from (1) to (4)).

Each processing solution has the following composition:

|  | [Tank solution] | [Replenisher solution] |
|---|---|---|
| [Color developer solution] | | |
| Water | 800 mL | 800 mL |
| Dimethylpolysiloxane surfactant ("Silicone KF351A", product of Shin-etsu Chemical) | 0.1 g | 0.1 g |
| Tri(isopropanol)amine | 8.8 g | 8.8 g |
| Ethylenediaminetetraacetic acid | 4.0 g | 4.0 g |
| Polyethylene glycol (molecular weight: 300) | 10.0 g | 10.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene fluorescent brightener ("Hakkol FWA-SF", product of Showa Chemical) | 2.5 g | 5.0 g |
| Sodium sulfite | 0.1 g | 0.1 g |
| Disodium-N,N-bis(sulfonatoethyl)-hydroxylamine | 8.5 g | 11.1 g |
| N-ethyl-N-(methanesulfonamidoethyl)-3-methyl-4-amikno-4-aminoaniline.3/2 sulfuric monohydrate | 5.0 g | 15.7 g |
| Potassium carbonate | 26.3 g | 26.3 g |
| Water (added to make) | 1000 mL | 1000 mL |
| PH (at 25° C./adjusted with potassium hydroxide or sulfuric acid) | 10.15 | 12.50 |
| [Bleaching and fixing solution] | | |
| Water | 700 mL | 600 mL |
| Ammonium ethylenediaminetetraacetoferrate (III) | 47.0 g | 94.0 g |
| Ethylenediaminetetraacetic acid | 1.4 g | 2.8 g |
| m-Carboxybenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/L) | 107.0 mL | 214.0 mL |
| Ammonium sulfite | 16.0 g | 32.0 g |
| Ammonium bisulfite | 23.1 g | 46.2 g |
| Water (added to make) | 1000 mL | 1000 mL |
| PH (at 25° C./adjusted with acetic acid or ammonia) | 6.0 | 6.0 |
| [Rinsing solution] | | |
| Chlorinated sodium isocyanurate | 0.02 g | 0.02 g |
| Deionized water (conductivity: 5 μs/cm or less) | 1000 mL | 1000 mL |
| PH | 6.5 | 6.5 |

After the above-described processing, the yellow color-forming density for Samples (101) to (126) were measured. Fog was determined from the minimum color density of the sample. The sensitivity was prescribed as a reciprocal of the exposure amount necessary for obtaining the color density of fog+1.0 and the relative sensitivity for each the obtained samples to the sensitivity of the development-processed Sample (101) taken as 100 are shown in Table 5, below.

TABLE 5

| | | | Relative sensitivity *1 | |
|---|---|---|---|---|
| Sample No. | Emulsion No. | Dopant | Exposure for 10 sec | Exposure for $10^{-4}$ sec |
| 101 (Comp. Ex.) | 1-1 | — | 100 | 100 |
| 102 (Comp. Ex.) | 1-2 | $[IrCl_6]^{3-}$ | 93 | 205 |
| 103 (Comp. Ex.) | 1-3 | $[IrCl_6]^{3-} + [Ru(CN)_6]^{4-}$ | 98 | 211 |
| 104 (Comp. Ex.) | 1-4 | $[IrCl_5(thiazole)]^{2-}$ | 95 | 215 |
| 105 (Invention) | 1-5 | $[IrCl_5(NH_3)]^{2-}$ | 102 | 223 |
| 106 (Invention) | 1-6 | $[IrCl_5(NH_2OH)]^{2-}$ | 98 | 219 |
| 107 (Invention) | 1-7 | $[IrCl_5(NCO)]^{3-}$ | 102 | 222 |
| 108 (Invention) | 1-8 | $[IrCl_5(NH_2SO_3)]^{3-}$ | 99 | 217 |

TABLE 5-continued

| | | | Relative sensitivity *1 | |
|---|---|---|---|---|
| Sample No. | Emulsion No. | Dopant | Exposure for 10 sec | Exposure for $10^{-4}$ sec |
| 109 (Invention) | 1-9 | [IrCl$_5$(NH$_2$SO$_2$NH$_2$)]$^{2-}$ | 100 | 220 |
| 110 (Invention) | 1-10 | [IrCl$_5$(N(CN)$_2$)]$^{3-}$ | 103 | 225 |
| 111 (Invention) | 1-11 | [IrCl$_5$(S(CN)$_2$)]$^{2-}$ | 101 | 221 |
| 112 (Invention) | 1-12 | [IrCl$_5$(NH$_2$C(=S)NH$_2$)]$^{2-}$ | 99 | 218 |
| 113 (Invention) | 1-13 | [IrCl$_5$(NH$_2$C(=NH)SCH$_3$)]$^{2-}$ | 102 | 222 |
| 114 (Invention) | 1-14 | [IrCl$_5$(1,3,4-thiadiazole)]$^{2-}$ | 101 | 223 |
| 115 (Invention) | 1-15 | [IrCl$_5$(1,2,4-thiadiazole)]$^{2-}$ | 100 | 219 |
| 116 (Invention) | 1-16 | [IrCl$_5$(NH$_3$)]$^{2-}$ + [Ru(CN)$_6$]$^{4-}$ | 110 | 230 |
| 117 (Invention) | 1-17 | [IrCl$_5$(NH$_2$OH)]$^{2-}$ + [Ru(CN)$_6$]$^{4-}$ | 107 | 226 |
| 118 (Invention) | 1-18 | [IrCl$_5$(NCO)]$^{3-}$ + [Ru(CN)$_6$]$^{4-}$ | 111 | 229 |
| 119 (Invention) | 1-19 | [IrCl$_5$(NH$_2$SO$_3$)]$^{3-}$ + [Ru(CN)$_6$]$^{4-}$ | 106 | 225 |
| 120 (Invention) | 1-20 | [IrCl$_5$(N(CN)$_2$)]$^{3-}$ + [Ru(CN)$_6$]$^{4-}$ | 112 | 231 |
| 121 (Invention) | 1-21 | [IrCl$_5$(S(CN)$_2$)]$^{2-}$ + [Ru(CN)$_6$]$^{4-}$ | 109 | 227 |
| 122 (Invention) | 1-22 | [IrCl$_5$(NH$_2$SO$_2$NH$_2$)]$^{2-}$ + [Ru(CN)$_6$]$^{4-}$ | 108 | 227 |
| 123 (Invention) | 1-23 | [IrCl$_5$(NH$_2$C(=S)NH$_2$)]$^{2-}$ + [Ru(CN)$_6$]$^{4-}$ | 107 | 227 |
| 124 (Invention) | 1-24 | [IrCl$_5$(NH$_2$C(SCH$_3$)NH)]$^{2-}$ + [Ru(CN)$_6$]$^{4-}$ | 109 | 229 |
| 125 (Invention) | 1-25 | [IrCl$_5$(1,3,4-thiadiazole)]$^{2-}$ + [Ru(CN)$_6$]$^{4-}$ | 110 | 230 |
| 126 (Invention) | 1-26 | [IrCl$_5$(1,2,4-thiadiazole)]$^{2-}$ + [Ru(CN)$_6$]$^{4-}$ | 109 | 228 |

*expressed as relative humidity under the respective conditions when the sensitivity of Sample 101 was designated as 100.

From Table 5, it has been found that the emulsions sing the dopants of the present invention are less in desensitization upon exposure for 10 seconds and markedly improved in high intensity reciprocity law failure.

Example II-16

<Emulsion 2-1: Preparation of Cubic Silver Chloride Sample (2)> (Comparative Example)

Grain formation was conducted in a similar manner to that employed for Emulsion 1-1 in Example 1 except that N,N'-dimethylimidazolidine-2-thione (1% aqueous solution) was omitted and the reaction temperature was adjusted to 55° C., whereby a cubic silver chloride emulsion having an average grain size of 0.38 μm (variation coefficient: 8%) was obtained. The resulting emulsion was chemically and spectrally sensitized optimally at 60° C. by adding a gold sensitizer (gold (I) tetrafluoroborate bis(1,4,5-trimethyl-1,2,4-triazolium-3-thiolato)) in an amount of $2.4 \times 10^{-5}$ mol/mol-Ag, a sulfur sensitizer (sodium thiosulfate) in an amount of $1 \times 10^{-7}$ mol/mol-Ag, and green-sensitive spectral sensitizing dyes (Sensitizing dyes D, E and F) in amounts of $3.6 \times 10^{-4}$ mol/mol-Ag, $7.0 \times 10^{-5}$ mol/mol-Ag and $2.8 \times 10^{-4}$ mol/mol-Ag respectively. Further, 1-(5-methylureidophenyl)-5-mercaptotetrazole was added in an amount of $4.4 \times 10^{-4}$ mol/mol-Ag, whereby Emulsion 2-1 was obtained.

<Emulsion 2-2; Preparation of Cubic Silver Chloride Sample Doped with [IrCl$_6$]$^{3-}$> (Comparative Example)

In a similar manner to that employed for Emulsion 2-1 except that [IrCl$_6$]$^{3-}$ was added to the 90 to 95% layer of Emulsion 2-1 in an amount of $1 \times 10^{-7}$ mol based on the amount of silver added to the emulsion, Emulsion 2-2 was prepared.

<Emulsion 2-3; Preparation of Cubic Silver Chloride Sample Doped with [IrCl$_6$]$^{3-}$ and [Os(NO)Cl$_5$]$^{2-}$> (Comparative Example)

In a similar manner to that employed for Emulsion 2-1 except that [IrCl$_6$]$^{3-}$ was added to the 90 to 95% portion, in terms of grain volume, from the center of the grain of Emulsion 2-1 in an amount of $3 \times 10^{-8}$ mol based on the amount of silver added to the emulsion, and [Os(NO)Cl$_5$]$^{2-}$ was added to the 10 to 50% portion, in terms of grain volume, from the center of the grain of Emulsion 2-1 in an amount of $1 \times 10^{-9}$ mol based on the amount of silver added to the emulsion, Emulsion 2-3 was prepared.

<Emulsion 2-4; Preparation of Cubic Silver Chloride Sample Doped with [IrCl$_5$(thiazole)]$^{2-}$> (Comparative Example)

In a similar manner to that employed for Emulsion 2-1 except that [IrCl$_5$(thiazole)]$^{2-}$ was added to the 90 to 95% layer of Emulsion 2-1 in an amount of $1 \times 10^{-7}$ mol based on the amount of silver added to the emulsion, Emulsion 2-4 was prepared.

<Emulsions 2-5 to 2-15: Preparation of Cubic Silver Chloride Samples Doped with [IrCl$_5$(N(CN)$_2$)]$^{3-}$, [IrCl$_5$(S(CN)$_2$)]$^{2-}$, [IrCl$_5$(NH$_2$C(=S)NH$_2$)]$^{2-}$, [IrCl$_5$(NH$_2$C(SCH$_3$)NH)]$^{2-}$, [IrCl$_5$([1,3,4]-thiadiazole)]$^{2-}$ and [IrCl$_5$([1,2,4]-thiadiazole)]$^{2-}$, respectively> (Invention Products)

In a similar manner to that employed for Emulsion 2-1 except that [IrCl$_5$(N(CN)$_2$)]$^{3-}$, [IrCl$_5$(S(CN)$_2$)]$^{2-}$, [IrCl$_5$(NH$_2$C(=S)NH$_2$)]$^{2-}$, [IrCl$_5$(NH$_2$C(SCH$_3$)NH)]$^{2-}$, [IrCl$_5$([1,3,4]-thiadiazole)]$^{2-}$ and [IrCl$_5$([1,2,4]-thiadiazole)]$^{2-}$ were added to the 90 to 95% portion, in terms of grain volume, from the center of the grain of Emulsion 2-1 in an amount of $1 \times 10^{-7}$ mol based on the amount of silver added to the emulsion, Emulsions 2-5 to 2-15 were prepared, respectively.

<Emulsions 2-16 to 2-26: Preparation of Cubic Silver Chloride Samples Doped with [IrCl$_5$(N(CN)$_2$)]$^{3-}$, [IrCl$_5$(S(CN)$_2$)]$^{2-}$, [IrCl$_5$(NH$_2$C(=S)NH$_2$)]$^{2-}$, [IrCl$_5$(NH$_2$C(SCH$_3$)NH)]$^{2-}$, [IrCl$_5$([1,3,4]-thiadiazole)]$^{2-}$ and [IrCl$_5$([1,2,4]-thiadiazole)]$^{2-}$, and [Os(NO)Cl$_5$]$^{2-}$ respectively> (Invention Products)

In a similar manner to that employed for Emulsion 2-1 except that [IrCl$_5$(N(CN)$_2$)]$^{3-}$, [IrCl$_5$(S(CN)$_2$)]$^{2-}$, [IrCl$_5$(NH$_2$C(=S)NH$_2$)]$^{2-}$, [IrCl$_5$(NH$_2$C(SCH$_3$)NH)]$^{2-}$, [IrCl$_5$([1,3,4]-thiadiazole)]$^{2-}$ and [IrCl$_5$([1,2,4]-thiadiazole)]$^{2-}$ were added to the 90 to 95% portion, in terms of grain volume, from the center of the grain of Emulsion 2-1 in an amount of $3 \times 10^{-8}$ mol based on the amount of silver added to the emulsion; and [Os(NO)Cl$_5$]$^{2-}$ was added to the 10 to 50% portion, in terms of grain volume, from the center of the grain of Emulsion 2-1 in an amount of 1×10$^{-9}$ mol based on the amount of silver added to the emulsion, Emulsions 2-16 to 2-26 were prepared, respectively.

With a similar constitution to that employed in Example 15 except that the emulsion of the first layer was replaced with Emulsions 2-1 to 2-26,, Samples (201) to (226) were prepared, respectively. These samples were tested for a similar test to that conducted in Example 1 and the below-described Test 2.

Test 2: Latent Image Stability After Exposure

Each of the samples was measured for sensitometry while changing the time from exposure for 1/10 second to processing A. Sensitivities when processing were conducted after 7 seconds and after 30 minutes were determined.

The results of these tests are shown in Table 6.

tography (e.g., developer, bleaching solution), and liquid crystals, particularly photography. Emulsions which have hard gradation while being minimized in desensitization and latent-image sensitization are available by using these metal complexes of the formula (IV). Moreover, photosensitive materials being improved in high intensity reciprocity law failure and having high maximum density can be provided.

The preparation process according to the present invention is excellent because it permits synthesis of metal complexes of the formula (IV) in a high purity and high yield. The metal complexes synthesized by the process of the present invention are excellent, because they do not adversely affect the photographic performance.

The entitle disclosure of each and every foreign patent application from which the benefit of foreign priority has been claimed in the present application is incorporated herein by reference, as if fully set forth herein.

TABLE 6

| Sample No. | Emulsion No. | Dopant | Relative sensitivity *1 | | Difference in sensitivity caused by change in time from exposure to processing*2 |
| --- | --- | --- | --- | --- | --- |
| | | | Exposure for 10 sec | Exposure for 10$^{-4}$ sec | |
| 201 (Comp. Ex.) | 2-1 | — | 100 | 100 | 1 |
| 202 (Comp. Ex.) | 2-2 | [IrCl$_6$]$^{3-}$ | 82 | 161 | 55 |
| 203 (Comp. Ex.) | 2-3 | [IrCl$_6$]$^{3-}$ + [Os(NO)Cl$_5$]$^{2-}$ | 80 | 163 | 51 |
| 204 (Comp. Ex.) | 2-4 | [IrCl$_5$(thiazole)]$^{2-}$ | 95 | 220 | 6 |
| 205 (Invention) | 2-5 | [IrCl$_5$(NH$_3$)]$^{2-}$ | 102 | 229 | 2 |
| 206 (Invention) | 2-6 | [IrCl$_5$(NH$_2$OH)]$^{2-}$ | 98 | 226 | 3 |
| 207 (Invention) | 2-7 | [IrCl$_5$(NCO)]$^{3-}$ | 102 | 230 | 1 |
| 208 (Invention) | 2-8 | [IrCl$_5$(NH$_2$SO$_3$)]$^{3-}$ | 99 | 223 | 3 |
| 209 (Invention) | 2-9 | [IrCl$_5$(NH$_2$SO$_2$NH$_2$)]$^{2-}$ | 100 | 227 | 3 |
| 210 (Invention) | 2-10 | [IrCl$_5$(N(CN)$_2$)]$^{3-}$ | 102 | 232 | 1 |
| 211 (Invention) | 2-11 | [IrCl$_5$(S(CN)$_2$)]$^{2-}$ | 101 | 229 | 1 |
| 212 (Invention) | 2-12 | [IrCl$_5$(NH$_2$C(=S)NH$_2$)]$^{2-}$ | 99 | 229 | 2 |
| 213 (Invention) | 2-13 | [IrCl$_5$(NH$_2$C(SCH$_3$)NH)]$^{2-}$ | 102 | 230 | 2 |
| 214 (Invention) | 2-14 | [IrCl$_5$(1,3,4-thiadiazole)]$^{2-}$ | 101 | 229 | 3 |
| 215 (Invention) | 2-15 | [IrCl$_5$(1,2,4-thiadiazole)]$^{2-}$ | 100 | 230 | 3 |
| 216 (Invention) | 2-16 | [IrCl$_5$(NH$_3$)]$^{2-}$ + [Os(NO)Cl$_5$]$^{2-}$ | 100 | 234 | 1 |
| 217 (Invention) | 2-17 | [IrCl$_5$(NH$_2$OH)]$^{2-}$ + [Os(NO)Cl$_5$]$^{2-}$ | 97 | 231 | 2 |
| 218 (Invention) | 2-18 | [IrCl$_5$(NCO)]$^{3-}$ + [Os(NO)Cl$_5$]$^{2-}$ | 101 | 236 | 1 |
| 219 (Invention) | 2-19 | [IrCl$_5$(NH$_2$SO$_3$)]$^{3-}$ + [Os(NO)Cl$_5$]$^{2-}$ | 96 | 227 | 2 |
| 220 (Invention) | 2-20 | [IrCl$_5$(NH$_2$SO$_2$NH$_2$)]$^{2-}$ + [Os(NO)Cl$_5$]$^{2-}$ | 98 | 233 | 2 |
| 221 (Invention) | 2-21 | [IrCl$_5$(N(CN)$_2$)]$^{3-}$ + [Os(NO)Cl$_5$]$^{2-}$ | 101 | 237 | 1 |
| 222 (Invention) | 2-22 | [IrCl$_5$(S(CN)$_2$)]$^{2-}$ + [Os(NO)Cl$_5$]$^{2-}$ | 100 | 234 | 1 |
| 223 (Invention) | 2-23 | [IrCl$_5$(NH$_2$C(=S)NH$_2$)]$^{2-}$ + [Os(NO)Cl$_5$]$^{2-}$ | 97 | 234 | 1 |
| 224 (Invention) | 2-24 | [IrCl$_5$(NH$_2$C(SCH$_3$)NH)]$^{2-}$ + [Os(NO)Cl$_5$]$^{2-}$ | 101 | 236 | 1 |
| 225 (Invention) | 2-25 | [IrCl$_5$(1,3,4-thiadiazole)]$^{2-}$ + [Os(NO)Cl$_5$]$^{2-}$ | 99 | 235 | 1 |
| 226 (Invention) | 2-26 | [IrCl$_5$(1,2,4-thiadiazole)]$^{2-}$ + [Os(NO)Cl$_5$]$^{2-}$ | 100 | 236 | 2 |

*expressed as relative humidity under the respective conditions when the sensitivity of Sample 201 was designated as 100.
*2: expressed by a difference in sensitivity caused by a change in time from exposure to processing.

It has been found that the emulsions of the present invention are free from high intensity reciprocity law failure between exposure for 10 seconds and exposure for 10$^{-4}$ second and their sensitivity does not change and is stable even if the time from exposure to processing varied (excellent in latent-image stability).

The metal complexes of the present invention represented by the formula (IV) are useful in various fields such as medical field, cosmetic preparations, soaps, detergents, cleaning compositions, analysis of materials, film coating to a metal material, plating, catalyst, colloid chemistry, pho- While the invention has been described in detail and with reference to specific embodiments thereof, it will be apparent to one skilled in the art that various changes and modifications can be made therein without departing from the spirit and scope thereof.

We claim:

1. A silver halide photographic emulsion comprising a metal complex represented by the following formula (I):

$$M_m[IrCl_n(L_1)_k(L_2)_{6-n-k}] \tag{I}$$

wherein, M represents a cation or anion, m represents an integer of 0 to 4, n represents an integer of 3 to 5, k represents an integer of 0 to 3, $L_1$ represents a ligand selected from the group consisting of heterocycles having at least 3 hetero atoms and ureas, $L_2$ represents an inorganic ligand other than Cl, with the proviso that when k represents 0, $L_2$ represents none of F, Br, I, NO, $H_2O$, CO and $C_2O_4$.

2. The silver halide photographic emulsion as in claim 1, wherein $L_1$ represents a ligand selected from heterocycles having at least 3 hetero atoms, n is 5 and k is 1.

3. The silver halide photographic emulsion as in claim 1, wherein n is 5 and k is 0.

4. The silver halide photographic emulsion as in claim 1, further comprising a complex represented by the following formula (II):

$$[Ma(CN)_{6-x}(La)_x]^p \tag{II}$$

wherein, Ma represents a transition metal of the group VII to IX in the Periodic Table, La represents a ligand, La may be the same or different when x represents 2 or more, x represents 0, 1, 2 or 3 and p represents 1-, 2-, 3- or 4-.

5. The silver halide photographic emulsion as in claim 1, further comprising a complex represented by the following formula (III):

$$[Mb(NO)(Lb)_5]^q \tag{III}$$

wherein, Mb represents a transition metal of the group VII to IX in the Periodic Table, 5 pieces of Lbs may be the same or different and each represents a ligand, and q represents 1-, 2- or 3-.

6. The silver halide photographic emulsion as in claim 1, wherein the silver halide grain contained therein is silver chloroiodide, silver chlorobromide or silver chlorobromo iodide having a silver chloride content of 95 mol % or more and is a tabular grain having an average aspect ratio of 3 or more.

7. A silver halide photosensitive material comprising a silver halide photographic emulsion of claim 1.

8. A metal complex represented by the following formula (IV):

$$N_k[IrX_{6-n'}Q_{n'}] \tag{IV}$$

wherein, N represents a counter cation; X represents a halogen ion; Q represents a compound which contains at least three atoms selected from nitrogen and sulfur atoms, and 5 or less carbon atoms, may contain another atom, and exhibits a ratio of (the number of carbon atoms)/(the total number of nitrogen atoms+oxygen atoms+sulfur atoms) of less than 0.5; n' represents an integer of 1 or 2; and k' represents the number of counter cations necessary for neutralizing the charge of a complex salt.

9. A process for preparing a metal complex of claim 8, which comprises using a metal complex represented by the following formula (B):

$$N_k[IrX_{6-m'}(H_2O)_{m'}] \tag{B}$$

wherein, N, X and k' have the same meanings as defined in the formula (IV), and m' represents an integer of 1 or 2.

10. The silver halide photographic emulsion as in claim 1, wherein $L_2$ is a ligand selected from the group consisting of $CNO^-$, $NCO^-$, $NCS^-$, $NH_2NH_2$, $NH_2OH$, $NH_2OSO_3H$, $NH_2SO_2NH_2$, $NH_2SO_3H$, $NH_3$, NSO, $OCN^{31}$, $SNC^-$, $(CN)_2N^-$, $(CN)_2S$, $(CN)_2S$, $(CN)_3P$, $P(S)(CN)_3$, $(CF_3SO_2)_2N^-$ and $(CF_3SO_2)(CN)N^-$.

11. The silver halide photographic emulsion as in claim 1, wherein $L_2$ is a lingand selected from the group consisting of $NH_2OH$, $NH_2OSO_3H$, $NH_3$, $(CN)_2N^-$ and $(CN)_2S$.

* * * * *